US009810690B2

(12) United States Patent
Patricelli et al.

(10) Patent No.: US 9,810,690 B2
(45) Date of Patent: Nov. 7, 2017

(54) METHOD FOR SCREENING INHIBITORS OF RAS

(71) Applicant: Araxes Pharma LLC, La Jolla, CA (US)

(72) Inventors: Matthew P. Patricelli, San Diego, CA (US); Ulf Peters, San Diego, CA (US); Liansheng Li, San Diego, CA (US); Pingda Ren, San Diego, CA (US); Yi Liu, San Diego, CA (US)

(73) Assignee: ARAXES PHARMA LLC, San Diego, CA (US)

( * ) Notice: Subject to any disclaimer, the term of this patent is extended or adjusted under 35 U.S.C. 154(b) by 0 days.

(21) Appl. No.: 15/342,100

(22) Filed: Nov. 2, 2016

(65) Prior Publication Data

US 2017/0131278 A1     May 11, 2017

Related U.S. Application Data

(63) Continuation-in-part of application No. PCT/US2016/057774, filed on Oct. 19, 2016.

(60) Provisional application No. 62/243,439, filed on Oct. 19, 2015.

(51) Int. Cl.
| | |
|---|---|
| *C12N 9/14* | (2006.01) |
| *G01N 33/573* | (2006.01) |
| *C12N 9/00* | (2006.01) |
| *C12N 15/70* | (2006.01) |

(52) U.S. Cl.
CPC .............. *G01N 33/573* (2013.01); *C12N 9/14* (2013.01); *C12Y 306/05002* (2013.01); *G01N 2500/04* (2013.01); *G01N 2500/20* (2013.01)

(58) Field of Classification Search
CPC C12N 9/14; C12Y 306/05002; G01N 33/573; G01N 2500/04
USPC .......... 435/7.23, 252.3; 536/23.2; 424/139.1, 424/143.1
See application file for complete search history.

(56) References Cited

U.S. PATENT DOCUMENTS

| | | |
|---|---|---|
| 3,702,849 A | 11/1972 | Timothy et al. |
| 3,752,660 A | 8/1973 | Little |
| 4,649,219 A | 3/1987 | Itoh et al. |
| 4,861,760 A | 8/1989 | Mazuel et al. |
| 4,911,920 A | 3/1990 | Jani et al. |
| 5,010,175 A | 4/1991 | Rutter et al. |
| 5,033,252 A | 7/1991 | Carter |
| 5,052,558 A | 10/1991 | Carter |
| 5,212,162 A | 5/1993 | Missel et al. |
| 5,288,514 A | 2/1994 | Ellman |
| 5,323,907 A | 6/1994 | Kalvelage |
| 5,403,841 A | 4/1995 | Lang et al. |
| 5,538,848 A | 7/1996 | Livak et al. |
| 5,539,083 A | 7/1996 | Cook et al. |
| 5,593,853 A | 1/1997 | Chen et al. |
| 5,605,798 A | 2/1997 | Koester |
| 5,731,352 A | 3/1998 | Lesieur et al. |
| 5,777,324 A | 7/1998 | Hillenkamp |
| 5,858,659 A | 1/1999 | Sapolsky et al. |
| 5,861,510 A | 1/1999 | Piscopio et al. |
| 5,863,949 A | 1/1999 | Robinson et al. |
| 5,919,626 A | 7/1999 | Shi et al. |
| 5,925,525 A | 7/1999 | Fodor et al. |
| 5,952,174 A | 9/1999 | Nikiforov et al. |
| 6,017,696 A | 1/2000 | Heller |
| 6,043,031 A | 3/2000 | Koester et al. |
| 6,045,996 A | 4/2000 | Cronin et al. |
| 6,051,380 A | 4/2000 | Sosnowski et al. |
| 6,068,818 A | 5/2000 | Ackley et al. |
| 6,214,872 B1 | 4/2001 | Robinson |
| 6,251,639 B1 | 6/2001 | Kurn |
| 6,903,118 B1 | 6/2005 | Biedermann et al. |
| 7,595,397 B2 | 9/2009 | Zindell et al. |
| 8,399,454 B2 | 3/2013 | Bian et al. |
| 8,426,401 B2 | 4/2013 | Bian et al. |
| 8,604,017 B2 | 12/2013 | Bian et al. |
| 8,697,684 B2 | 4/2014 | Bian et al. |
| 8,741,887 B2 | 6/2014 | Bian et al. |
| 8,759,333 B2 | 6/2014 | Connolly et al. |
| 9,227,978 B2 | 1/2016 | Ren et al. |
| 9,376,559 B2 | 6/2016 | Holtcamp et al. |
| 2002/0169300 A1 | 11/2002 | Waterman et al. |
| 2003/0022344 A1 | 1/2003 | Williams et al. |
| 2003/0166620 A1 | 9/2003 | Lee et al. |
| 2005/0012070 A1 | 1/2005 | Inoue et al. |
| 2005/0227997 A1 | 10/2005 | Noe et al. |
| 2008/0004348 A1 | 1/2008 | Yous et al. |
| 2008/0039450 A1 | 2/2008 | Jensen et al. |
| 2009/0054402 A1 | 2/2009 | Wang et al. |
| 2009/0124636 A1 | 5/2009 | Barber et al. |
| 2009/0298075 A1 | 12/2009 | Travers et al. |

(Continued)

FOREIGN PATENT DOCUMENTS

| | | |
|---|---|---|
| CN | 1267291 A | 9/2000 |
| EP | 0606046 A1 | 7/1994 |

(Continued)

OTHER PUBLICATIONS

US 5,962,233, 10/1999, Livak et al. (withdrawn)
Adibekian, A., et al., Optimization and characterization of a triazole urea dual inhibitor for lysophospholipase 1 (LYPLA1) and lysophospholipase 2 (LYPLA2), in Probe Reports from the NIH Molecular Libraries Program. 2010: Bethesda (MD).
"Allen, Lloyd. The art, science, and technology of pharmaceutical compounding. American Pharmacists Association, 1997."
Al-Muhammed, et al. In-vivo studies on dexamethasone sodium phosphate liposomes. J Microencapsul. May-Jun. 1996;13(3):293-306.
"Sambrook, et al. (1989) Molecular Cloning—A Laboratory Manual (2nd ed.) vol. 1-3, Cold Spring Harbor Laboratory, Cold Spring Harbor Press, N.Y.,"

(Continued)

*Primary Examiner* — Robert Mondesi
*Assistant Examiner* — Md. Younus Meah
(74) *Attorney, Agent, or Firm* — Wilson Sonsini Goodrich & Rosati

(57) ABSTRACT

Provided herein are compositions, reactions mixtures, mutant Ras proteins, kits, substrates, and systems for selecting a Ras antagonist, as well as methods of using the same.

30 Claims, 6 Drawing Sheets

(56) References Cited

U.S. PATENT DOCUMENTS

| | | |
|---|---|---|
| 2010/0331300 A1 | 12/2010 | Bian et al. |
| 2011/0230476 A1 | 9/2011 | Niu et al. |
| 2011/0269244 A1 | 11/2011 | Petter et al. |
| 2011/0311447 A1 | 12/2011 | Tu et al. |
| 2011/0319290 A1 | 12/2011 | Raymond et al. |
| 2013/0012489 A1 | 1/2013 | Mederski et al. |
| 2013/0274252 A1 | 10/2013 | Pandey et al. |
| 2013/0302407 A1 | 11/2013 | Rao et al. |
| 2014/0288045 A1 | 9/2014 | Ren et al. |
| 2015/0087628 A1 | 3/2015 | Ostrem et al. |
| 2015/0239900 A1 | 8/2015 | Li et al. |
| 2016/0031898 A1 | 2/2016 | Ren et al. |
| 2016/0108019 A1 | 4/2016 | Li et al. |
| 2016/0159738 A1 | 6/2016 | Ren et al. |
| 2016/0166571 A1 | 6/2016 | Janes et al. |
| 2016/0297774 A1 | 10/2016 | Li et al. |
| 2016/0368930 A1 | 12/2016 | Ostrem et al. |
| 2017/0022184 A1 | 1/2017 | Li et al. |

FOREIGN PATENT DOCUMENTS

| | | |
|---|---|---|
| EP | 0780386 A1 | 6/1997 |
| EP | 0818442 A2 | 1/1998 |
| EP | 0931788 A2 | 7/1999 |
| EP | 1004578 A2 | 5/2000 |
| GB | 939516 A | 10/1963 |
| JP | S59163372 A | 9/1984 |
| JP | 2005502623 A | 1/2005 |
| JP | 2008524154 A | 7/2008 |
| WO | WO-9005719 A1 | 5/1990 |
| WO | WO-9119735 A1 | 12/1991 |
| WO | WO-9200091 A1 | 1/1992 |
| WO | WO-9320242 A1 | 10/1993 |
| WO | WO-9605309 A2 | 2/1996 |
| WO | WO-9627583 A1 | 9/1996 |
| WO | WO-9633172 A1 | 10/1996 |
| WO | WO-9700271 A1 | 1/1997 |
| WO | WO-9803516 A1 | 1/1998 |
| WO | WO-9807697 A1 | 2/1998 |
| WO | WO-9830566 A1 | 7/1998 |
| WO | WO-9833496 A1 | 8/1998 |
| WO | WO-9833768 A1 | 8/1998 |
| WO | WO-9834915 A1 | 8/1998 |
| WO | WO-9834918 A1 | 8/1998 |
| WO | WO-9857948 A1 | 12/1998 |
| WO | WO-9907675 A1 | 2/1999 |
| WO | WO-9929667 A1 | 6/1999 |
| WO | WO-9952889 A1 | 10/1999 |
| WO | WO-9952910 A1 | 10/1999 |
| WO | WO-9967641 A2 | 12/1999 |
| WO | WO-0039587 A1 | 7/2000 |
| WO | WO-03004480 A2 | 1/2003 |
| WO | WO-2004074283 A1 | 9/2004 |
| WO | WO-2005070891 A2 | 8/2005 |
| WO | WO-2005082892 A2 | 9/2005 |
| WO | WO-2006066948 A1 | 6/2006 |
| WO | WO-2007144394 A2 | 12/2007 |
| WO | WO-2008009078 A2 | 1/2008 |
| WO | WO-2010087399 A1 | 8/2010 |
| WO | WO-2010121918 A1 | 10/2010 |
| WO | WO-2011031896 A2 | 3/2011 |
| WO | WO-2011093524 A1 | 8/2011 |
| WO | WO-2012016082 A1 | 2/2012 |
| WO | WO-2012054716 A1 | 4/2012 |
| WO | WO-2012174489 A2 | 12/2012 |
| WO | WO-2013064068 A1 | 5/2013 |
| WO | WO-2013140148 A1 | 9/2013 |
| WO | WO-2013155223 A1 | 10/2013 |
| WO | WO-2014143659 A1 | 9/2014 |
| WO | WO-2014152588 A1 | 9/2014 |
| WO | WO-2014159837 A1 | 10/2014 |
| WO | WO-2014201435 A1 | 12/2014 |
| WO | WO-2015054572 A1 | 4/2015 |
| WO | WO-2015144001 A1 | 10/2015 |
| WO | WO-2015184349 A2 | 12/2015 |
| WO | WO-2016044772 A1 | 3/2016 |
| WO | WO-2016049524 A1 | 3/2016 |
| WO | WO-2016049565 A1 | 3/2016 |
| WO | WO-2016049568 A1 | 3/2016 |
| WO | WO-2016164675 A1 | 10/2016 |
| WO | WO-2016168540 A1 | 10/2016 |
| WO | WO-2017015562 A1 | 1/2017 |

OTHER PUBLICATIONS

"Appel et al., "Supramolecular Cross-Linked Networks via Host-Guest Complexation with Cucurbit[8]uril," 1 Am. Chem. Soc. 132(40):14251-14260, Jul. 2010."

Arkin, et al. Binding of small molecules to an adaptive protein-protein interface. Proc Natl Acad Sci U S A. Feb. 18, 2003;100(4):1603-8. Epub Feb. 11, 2003.

"Sasaki, et al. "Selective Formation of Stable Triplexes Including a TA or a CG Interrupting Site with New Bicyclic Nucleoside Analogues (WNA)," J. Am. Chem. Soc. 126(2):516-528, Jan. 2004."

"Ausubel et al. Current Protocols in Molecular Biology. 1987."

Bachovchin, D.A., et al., Identification of selective inhibitors of uncharacterized enzymes by high-throughput screening with fluorescent activity-based probes. Nat Biotechnol, 2009. 27(4): p. 387-94.

"Banker et al. (eds.), Modern Pharmaceutics, New York, Marcel Dekker, Inc., 1996, pp. 451 and 596. (3 pages)".

"Barbe et al., "Highly Chemoselective Metal-Free Reduction of Tertiary Amides," I Am. Chem. Soc. 130:18-19, 2008."

"Begue et al., "Ions a-Cetocarbenium. Influence De La Structure Sur L'Evolution Des Ions a-Cetocyclohexylcarbenium," Tetrahedron 31(20):2505-2511, 1975. (English Abstract Only)".

Berge, et al. Pharmaceutical salts. J Pharm Sci. Jan. 1977;66(1):1-19.

Campbell, et al. Phosphonate Ester Synthesis Using a Modified Mitsunobu Condensation. J. Org. Chem., 1994, 59 (3), pp. 658-660.

"Chemocare.com "Taxol." (c) 2016. Available from:<http://www.chemocare.com/chemotherapy/drug-info/taxol.aspx>."

Chen, et al. "Analogous" Organic Synthesis of Small-Compound Libraries: Validation of Combinatorial Chemistry in Small-Molecule Synthesis. J. Am. Chem. Soc., 1994, 116 (6), pp. 2661-2662.

Cho, et al. An unnatural biopolymer. Science. Sep. 3, 1993;261(5126):1303-5.

Chonn, et al. Recent advances in liposomal drug-delivery systems. Curr Opin Biotechnol. Dec. 1995;6(6):698-708.

Choong, et al. Identification of potent and selective small-molecule inhibitors of caspase-3 through the use of extended tethering and structure-based drug design. J Med Chem. Nov. 7, 2002;45(23):5005-22.

Cox, A.D., et al., Drugging the undruggable RAS: Mission Possible? Nat Rev Drug Discov, 2014. 13(11): p. 828-51.

"Database Pubchem Substance [Online] NCBI. Database accession No. SID22405303. Mar. 5, 2007."

Dewitt, et al. "Diversomers": an approach to nonpeptide, nonoligomeric chemical diversity. Proc Natl Acad Sci U S A. Aug. 1, 1993;90(15):6909-13.

Dillon, M.B., et al., Novel inhibitors for PRMT1 discovered by high-throughput screening using activity-based fluorescence polarization. ACS Chem Biol, 2012. 7(7): p. 1198-204.

"Duncan et al., "N-Dialkylaminoalkybiphenylamines as Antimalarial and Antischistosomal Agents," Journal of Medicinal Chemistry 12:25-29, Jan. 1969."

Erlanson, et al. Site-directed ligand discovery. Proc Natl Acad Sci U S A. Aug. 15, 2000;97(17):9367-72.

Eyles, et al. Oral delivery and fate of poly(lactic acid) microsphere-encapsulated interferon in rats. J Pharm Pharmacol. Jul. 1997;49(7):669-74.

Fingl, et al. In: The Pharmacological basis of therapeutics, Ch. 1, p. 1. 1975.

"Forbes et al., "COSMIC 2005," British Journal of Cancer 94:318-322, 2006."

Furka, et al. General method for rapid synthesis of multicomponent peptide mixtures. Int J Pept Protein Res. Jun. 1991;37(6):487-93.

(56) References Cited

OTHER PUBLICATIONS

Gao, et al. Controlled release of a contraceptive steroid from biodegradable and injectable gel formulations: in vitro evaluation. Pharm Res. Jun. 1995;12(6):857-63.
Gorfe, et al. Mapping the nucleotide and isoform-dependent structural and dynamical features of Ras proteins. Structure. Jun. 2008;16(6):885-96. doi: 10.1016/j.str.2008.03.009.
Hagihara, et al. Vinylogous polypeptides : an alternative peptide backbone. J. Amer. Chem. Soc. 1992, 114:6568-70.
Hall, et al. The effect of Mg2+ on the guanine nucleotide exchange rate of p21 N-ras. J Biol Chem. Aug. 25, 1986;261(24):10963-5.
Hall, et al. The structural basis for the transition from Ras-GTP to Ras-GDP. Proc Natl Acad Sci U S A. Sep. 17, 2002;99(19):12138-42. Epub Sep. 4, 2002.
Hara, et al. Guanine nucleotide binding properties of purified v-Ki-ras p21 protein produced in *Escherichia coli*. Oncogene Res. May 1988;2(4):325-33.
Hardy, et al. Discovery of an allosteric site in the caspases. Proc Natl Acad Sci U S A. Aug. 24, 2004;101(34):12461-6. Epub Aug. 16, 2004.
"Hattori et al., "Neutralizing Monoclonal Antibody Against ras Oncogene Product p21 Which Impairs Guanine Nucleotide Exchange," Mol. Cell. Biol. 7(5):1999-2002, May 1987.".
Hirschmann, et al. Nonpeptidal peptidomimetics with .beta.-D-glucose scaffolding. A partial somatostatin agonist bearing a close structural relationship to a potent, selective substance P antagonist. J. Am. Chem. Soc., 1992, 114 (23), pp. 9217-9218.
Houghton, et al. Generation and use of synthetic peptide combinatorial libraries for basic research and drug discovery. Nature. Nov. 7, 1991;354(6348):84-6.
"Singh et al., "A Gene Expression Signature Associated with "K-Ras Addiction" Reveals Regulators of EMT and Tumor Cell Survival," Cancer Cell 15:489-500, Jun. 2009."
"International search report and written opinion dated Jul. 22, 2013 for PCT/US2013/036031."
"International search report with written opinion dated Feb. 2, 2016 for PCT/US2015/052437".
"International search report with written opinion dated Feb. 6, 2014 for PCT/US2014/027454".
"International search report with written opinion dated Feb. 18, 2016 for PCT/US2015/051030".
"International search report with written opinion dated Mar. 2, 2016 for PCT/US2015/052427".
"International search report with written opinion dated May 30, 2016 for PCT/US2016/027673".
"International search report with written opinion dated Jul. 8, 2016 for PCT/US2016/026573".
"International search report with written opinion dated Jul. 25, 2014 for PCT/US2014/027504".
"International search report with written opinion dated Dec. 9, 2015 for PCT/US2015/052349".
"International search report with written opinion dated Dec. 17, 2014 for PCT/US2014/060036".
"Ito et al., "Regional Polysterism in the GTP-Bound Form of the Human c-Ha-Ras Protein," Biochemistry 36(30):9109-1919, Jul. 1997."
"Johnson et al., "The Chemistry of fl-Bromopropionyl Isocyanate. I. Synthesis of 1-Aryldihydrouracils," The Journal of Organic Chemistry 24(9):1391-1392, Sep. 1959."
Jones, et al. Increased frequency of the k-ras G12C mutation in MYH polyposis colorectal adenomas. Br J Cancer. Apr. 19, 2004;90(8):1591-3.
"Jordan, "Tamoxifen: A Most Unlikely Pioneering Medicine," Nature Reviews 2:205-213, Mar. 2003."
"Kelly et al., "Synthesis of Isomeric 3-Piperidinyl and 3-Pyrrolidinyl Benzo[5,6]cyclohepta[1,2-blpyridines: Sulfonamido Derivatives as Inhibitors of Ras Prenylation," Bioorganic & Medicinial Chemistry 6:673-686, 1998."
"Kimmel, et al. Preparation of cDNA and the Generation of cDNA Libraries: Overview. Methods Enzymol. 1987;152:307-16."

Kraulis, et al. Solution structure and dynamics of ras p21.GDP determined by heteronuclear three- and four-dimensional NMR spectroscopy. Biochemistry. Mar. 29, 1994;33(12):3515-31.
"Kumar et al., "Synthesis of 3-Sulfonylamino Quinolines form 1-(2-Aminophenyl) Propargyl Alcohols through a Ag(I)-Catalyzed Hydroamination, (2 + 3) Cycloaddition, and an Unusual Strain-Driven Ring Expansion," Organic Letters 17(9):2226-2229, Apr. 2015."
Lachman, et al. Pharmaceutical dosage forms. vol. 1-3. Marcel Dekker, 1992.
"Le Picard et al., "Design and Synthesis of Naphthalenic Derivatives as Potential Inhibitors of Hydroxyindole-0-methyltransferase," Pharm. Pharmacol. Commun. 5:183-188, 1999."
Lee, et al. The mutation spectrum revealed by paired genome sequences from a lung cancer patient. Nature. May 27, 2010;465(7297):473-7. doi: 10.1038/nature09004.
Lenzen, et al. Analysis of intrinsic and CDC25-stimulated guanine nucleotide exchange of p21ras-nucleotide complexes by fluorescence measurements. Methods Enzymol. 1995;255:95-109.
Liang, et al. Parallel synthesis and screening of a solid phase carbohydrate library. Science. Nov. 29, 1996;274(5292):1520-2.
"Liu et al., "Polygonatum cyrtonema lectin induces murine fibrosarcoma L929 cell apoptosis and autophagy via blocking Ras-Raf and PI3K-Akt signaling pathways," Biochimie 92:1934-1938, 2010."
"Loboda et al., "A gene expression signature of RAS pathway dependence predicts response to PI3K and RAS pathway inhibitors and expands the population of RAS pathway activated tumors," BMC Medical Genomics 3(26):1-11, 2010."
Lone, A.M., et al., A substrate-free activity-based protein profiling screen for the discovery of selective PREPL inhibitors. J Am Chem Soc, 2011. 133(30): p. 11665-74.
"Long, D. "Taxol: An important compound with an impressive structure." (c) 2016. Available from:< https://longscience.com/2011/09/10/taxol-an-organic-compound-you-should-know-about/>".
"Malani et al., "Synthesis, characterization and in vitro screening on bacterial, fungal and malarial strain of piprazinyl cyano biphenyl based compounds," Bioorganic Chemistry 51:16-23, 2013."
Margarit, et al. Structural evidence for feedback activation by Ras.GTP of the Ras-specific nucleotide exchange factor SOS. Cell. Mar. 7, 2003;112(5):685-95.
Maurer, T., et al., Small-molecule ligands bind to a distinct pocket in Ras and inhibit SOS-mediated nucleotide exchange activity. Proc Natl Acad Sci U S A, 2012. 109(14): p. 5299-304.
"Milburn et al., "Molecular Switch for Signal Transduction: Structural Differences Between Active and Inactive Forms of Protooncogenic ras Proteins," Science 247(4945):939-945, Feb. 1990."
Minto, et al. Pharmacokinetics and pharmacodynamics of nandrolone esters in oil vehicle: effects of ester, injection site and injection volume. J Pharmacol Exp Ther. Apr. 1997;281(1):93-102.
"Notice of allowance dated Feb. 27, 2017 for U.S. Appl. No. 14/933,734."
"Notice of allowance dated Mar. 2, 2017 for U.S. Appl. No. 14/511,425."
"Notice of allowance dated Aug. 6, 2015 for U.S. Appl. No. 14/212,656".
"Office action dated Jan. 15, 2016 for U.S. Appl. No. 14/511,425".
"Office action dated Mar. 27, 2015 for U.S. Appl. No. 14/212,656".
"Office action dated Jun. 20, 2016 for U.S. Appl. No. 14/511,425".
"Office action dated Oct. 7, 2016 for U.S. Appl. No. 14/933,734".
"Office action dated Oct. 18, 2016 for U.S. Appl. No. 14/866,147".
"Office action dated Oct. 26, 2016 for U.S. Appl. No. 15/093,951".
"Office action dated Nov. 3, 2016 for U.S. Appl. No. 14/511,425".
"Ohnmacht, Jr. et al., "Antimalarials. 5. a-Dibutylaminomethyl- and a-(2-Piperidyl)-3-quinolinemethanols," Journal of Medicinal Chemistry 14(1):17-24, 197."
Ostrem, J.M., et al., K-Ras(G12C) inhibitors allosterically control GTP affinity and effector interactions. Nature, 2013. 503(7477): p. 548-51.

(56) References Cited

OTHER PUBLICATIONS

Ostro, et al. Use of liposomes as injectable-drug delivery systems. Am J Hosp Pharm. Aug. 1989;46(8):1576-87.
"Pacold et al., "Crystal Structure and Functional Analysis of Ras Binding to Its Effector Phosphoinositide 3-Kinase y," Cell 103(6):931-943, Dec. 2000."
Palmioli, et al. First experimental identification of Ras-inhibitor binding interface using a water-soluble Ras ligand. Bioorg Med Chem Lett. Aug. 1, 2009;19(15):4217-22. doi: 10.1016/j.bmcl. 2009.05.107. Epub May 30, 2009.
Palmioli, et al. Selective cytotoxicity of a bicyclic Ras inhibitor in cancer cells expressing K-Ras(G13D). Biochem Biophys Res Commun. Sep. 4, 2009;386(4):593-7. doi: 10.1016/j.bbrc.2009.06.069. Epub Jun. 18, 2009.
"Pardin, et al. Synthesis and evaluation of peptidic irreversible inhibitors of tissue transglutaminase. Bioorg Med Chem. Dec. 15, 2006;14(24):8379-85. Epub Sep. 27, 2006."
Pautsch, A. et al., Crystal structure of the C3bot-RalA complex reveals a novel type of action of a bacterial exoenzyme. EMBO J, 2005, 24:3670-3680.
"Pedeboscq et al., "Synthesis and evaluation of apoptosis induction of thienopyrimidine compounds on KRAS and BRAF mutated colorectal cancer cell lines," Bioorganic & Medicinal Chemistry 20:6724-6731, 2012."
"Peri et al., "Arabinose-derived bicyclic amino acids: synthesis, conformational analysis and construction of an a,,(33-selective RGD peptide," I Am. Chem. Soc., Perkins Trans 1(5):638-644, Feb. 2002."
"Peri et al., "Sugar-Derived Ras Inhibitors: Group Epitope Mapping by NMR Spectroscopy and Biological Evaluation," Eur. I Org. Chem. 2006(16):3707-3720, Aug. 2006."
"Peri et al., "Synthesis of bicyclic sugar azido acids and their incorporation in cyclic peptides," Chem. Commun. 23:2303-2304, Jan. 2000."
"PICKAR. Dosage Calculations. 1999."
"Spiegel et al., "Small-molecule modulation of Ras signaling," Nature Chemical Biology 10:613-622, Aug. 2014."
"PubChem Compound, "(2S,6R)-hexahydrofuro[3,2-blfuran-2,6-diyl dicarbonochloridate:Compound Summary CID 53396983," Oct. 30, 2011, retrieved from http://pubchem.ncbi.nlm.nih.gov/compound/53396983, 6 pages."
"PubChem Compound, "(4-hydroxypiperidin-l-y1)-pyridin-4-ylmethanone: AC1L5BNJ," retrieved on Feb. 17, 2014, from http://pubchem.ncbi.nlm.nih.gov/summary/summary.cgi?cid=76837, Jul. 8, 2005, 5 pages."
"PubChem Compound, "AKOS024742141," Nov. 27, 2010, retrieved from http://pubchem.ncbi.nim.nih.gov/compound/49702158#x304, CID 49702158, 12 pages."
"PubChem Compound, "SCHEMBL6674271," Dec. 1, 2012, retrieved from http://pubchem.ncbi.nim.nih.gov/compound/69861127#x304, CID 69861127, 12 pages."
"PubChem Compound, "SCHEMBL6797439," Dec. 1, 2012, retrieved from http://pubchem.ncbi.nim.nih.gov/compound/69898605#x304, CID 69898605, 12 pages."
"PubChem Compound, "Compound Summary for CID 21765509: Molecular Formula C18H21N508," Dec. 5, 2007, retrieved from http //pubchem.ncbi.nlm.nih.gov/compound/21765509, 4 pages."
"PubChem Compound, "Compound Summary for CID 21765511: Molecular Formula C18H2IN508," Dec. 5, 2007, retrieved from http://pubchem.ncbi.nlm.nih.gov/compound/21765511, 4 pages."
"PubChem Compound, "Compound Summary for CID 60018735: Molecular Formula C30I-13o013," Aug. 20, 2012, retrieved from http://pubchem.ncbi.nlm.nih.gov/compound/60018735#section=Top, 1 page."
"PubChem Compound, "Compound Summary for CID 72623693: AGN-PC-0D83J7," Jan. 9, 2014, retrieved from http://pubchem.ncbi.nlm.nih.gov/compound/72623693, 6 pages."
"PubChem Compound, "Compound Summary for CID 9897840: Molecular Formula C501446020," Oct. 25, 2006, retrieved from http://pubchem.ncbi.nlm.nih.gov/compound/9897840, 6 pages."

"PubChem, Substance Record for SID 44253980. Create Date: Dec. 5, 2007. Retrieved from the Internet.< URL: https://pubchem.ncbi.nlm.nih.gov/substance/44253980>".
Rao. Recent developments of collagen-based materials for medical applications and drug delivery systems. J Biomater Sci Polym Ed. 1995;7(7):623-45.
Remington. Remington's Pharmaceutical Sciences. 17th Edition. Mack Publishing Company, Easton, PA. 1985.
Remington. Remington: The science and practice of pharmacy. 20th Edition. Gennaro, Eds. Lippincott Williams & Wilkins, 2003.
Rensland, et al. Substrate and product structural requirements for binding of nucleotides to H-ras p21: the mechanism of discrimination between guanosine and adenosine nucleotides. Biochemistry. Jan. 17, 1995;34(2):593-9.
Schubbert, et al. Biochemical and functional characterization of germ line KRAS mutations. Mol Cell Biol. Nov. 2007;27(22):7765-70. Epub Sep. 17, 2007.
Shima, F., et al., Discovery of small-molecule Ras inhibitors that display antitumor activity by interfering with Ras.GTP-effector interaction. Enzymes, 2013. 34 Pt. B: p. 1-23.
Sun, Q., et al., Discovery of small molecules that bind to K-Ras and inhibit Sos-mediated activation. Angew Chem Int Ed Engl, 2012. 51(25): p. 6140-3.
"Taveras et al., "Ras Oncoprotein Inhibitors: The Discovery of Potent, Ras Nucleotide Exchange Inhibitors and the Structural Determination of a Drug-Protein Complex," Bioorganic and Medicinal Chemistry 5(1):125-133, 1997."
"Streuff et al., "First asymmetric aminohydroxylation of acrylamides," Tetrahedron: Asymmetry 16(21):3492-3496, Oct. 2005."
"Tsubaki et al., "Reduction of metastasis, cell invasion, and adhesion in mouse osteosarcoma by YM529/ONO-5920-induced blockade of the Ras/MEK/ERK and Ras/PI3K/Akt pathway," Toxicology and Applied Pharmacology 259(3):402-410, Jan. 2012."
"Tulshian et al., "Synthesis and Phosphodiesterase Activity of Carboxylic Acid Mimetics of Cyclic Guanosine 3',5'-Monophosphate," 1 Med. Chem. 36(9):1210-1220, Jan. 1993."
"Sunaga et al., "Knockdown of Oncogenic KRAS in Non-Small Cell Lung Cancers Suppresses Tumor Growth and Sensitizes Tumor Cells to Targeted Therapy," Molecular Cancer Therapeutics 10(2):336-346, Feb. 2011."
Vaughan, et al. Human antibodies with sub-nanomolar affinities isolated from a large non-immunized phage display library. Nat Biotechnol. Mar. 1996;14(3):309-14.
"Vetter et al., "The Guanine Nucleotide-Binding Switch in Three Dimensions," Science 294(5545):1299-1304, Nov. 2001."
"Wolff, (ed.), Burger's Medicinal Chemistry and Drug Discovery, Fifth Edition, vol. 1: Principles and Practice, San Diego, California, John Wiley & Sons, 1994, pp. 975-977. (4 pages)".
"Wu et al., "Stereoselective synthesis of dioxabicycles from 1-C-allyl-2-O-benzyl-glycosides—An intramolecular cyclization between 2-O-benzyl oxygen and the allyl double bond," Can. I Chem. 84(1):597-602, Jan. 2006."
Yan et. al., Discovery and characterization of small molecules that target the GTPase Ral. Nature, 2014, 515:443-447.
"Yang et al., "Fragment-Based Discovery of Nonpeptidic BACE-1 Inhibitors Using Tethering," Biochemistry 48:4488-4496, 2009."
"Sydor et al., "Transient Kinetic Studies on the Interaction of Ras and the Ras-Binding Domain of c-Raf-1 Reveal Rapid Equilibration of the Complex," Biochemistry 37:14292-14299, 1998."
"Young et al., "Oncogenic and Wild-type Ras Play Divergent Roles in the Regulation of Mitogen-Activated Protein Kinase Signaling," Cancer Discovery 3(1):112-123, Jan. 2013."
"Zenkl et al., "Sugar-Responsive Fluorescent Nanospheres," Macromol. Biosci. 8:146-152, 2008."
McMahon, et al. The case for colorectal cancer screening. Semin Roentgenol. Oct. 2000;35(4):325-32.
Pinedo, et al. Aggressive combination therapy to cure patients with metastatic cancer. Lancet Oncol. Oct. 2000;1:72-3.
Vippagunta et al. Crystalline solids. Adv Drug Deliv Rev. May 16, 2001;48(1):3-26.
Co-pending U.S. Appl. No. 15/508,387, filed Mar. 2, 2017.

(56) References Cited

OTHER PUBLICATIONS

International search report and written opinion dated Apr. 13, 2017 for PCT Application No. PCT/US2016/057774.
International search report with written opinion dated Feb. 2, 2016 for PCT/US15/52437.
Pathan, et al. Lead identification for the K-Ras protein: virtual screening and combinatorial fragment-based approaches. OncoTargets and therapy 9 (2016): 2575-2584.
Patricelli, et al. Selective inhibition of oncogenic KRAS output with small molecules targeting the inactive state. Cancer discovery 6.3 (2016): 316-329.
American Chemical Society. STN Database. Nov. 16, 1984. RN5530-21-2.
Chemocare.com "Taxol." 2016. Available from<http://www.chemocare.com/chemotherapy/drug-info/taxol.aspx>.
European search report dated Nov. 6, 2015 for EP13775551.8.
International preliminary report on patentability dated Oct. 14, 2014 for PCT/2013/036031.
Long, D. "Taxol: An important compound with an impressive structure." 2016. Available from<https://longscience.com/2011/09/10/taxol-an-organic-compound-you-should-know-about/>.
Office action dated May 31, 2017 for U.S. Appl. No. 14/934,184.
International search report and written opinion dated Aug. 16, 2017 for PCT Application No. PCT/US17/24839.
"Pubchem CID 10375614" Create Date: Oct. 25, 2006 (Oct. 25, 2006) Date Accessed: Aug. 8, 2017 (Aug. 8, 2017); p. 3.

```
                          62                              92 95
                          ↓                                ↓  ↓
HUMAN KRAS   56  LDTAGQEEYSAMRDQYMRTGEGFLCVFAINNTKSFEDIHHYREQIKRVKDS  106
HUMAN HRAS   56  LDTAGQEEYSAMRDQYMRTGEGFLCVFAINNTKSFEDIHQYREQIKRVKDS  106
HUMAN NRAS   56  LDTAGQEEYSAMRDQYMRTGEGFLCVFAINNSKSFADINLYREQIKRVKDS  106
HUMAN MRAS   66  LDTAGQEEFSAMREQYMRTGDGFLIVYSVTDKASFEHVDRFHQLILRVKDR  116
HUMAN ERAS   94  LDTAGQAIHRALRDQCLAVCDGVLGVFALDDPSSLIQLQQ---IWATWGPH  141
HUMAN RRAS2  67  LDTAGQEEFGAMREQYMRTGEGFLLVFSVTDRGSFEEIYKFQRQILRVKDR  117
HUMAN RALA   67  LDTAGQEDYAAIRDNYFRSGEGFLCVFSITEMESFAATADFREQILRVKED  117
HUMAN RIT1   74  LDTAGQAEFTAMRDQYMRAGEGFIICYSITDRRSFHEVREFKQLIYRVRRT  124
```

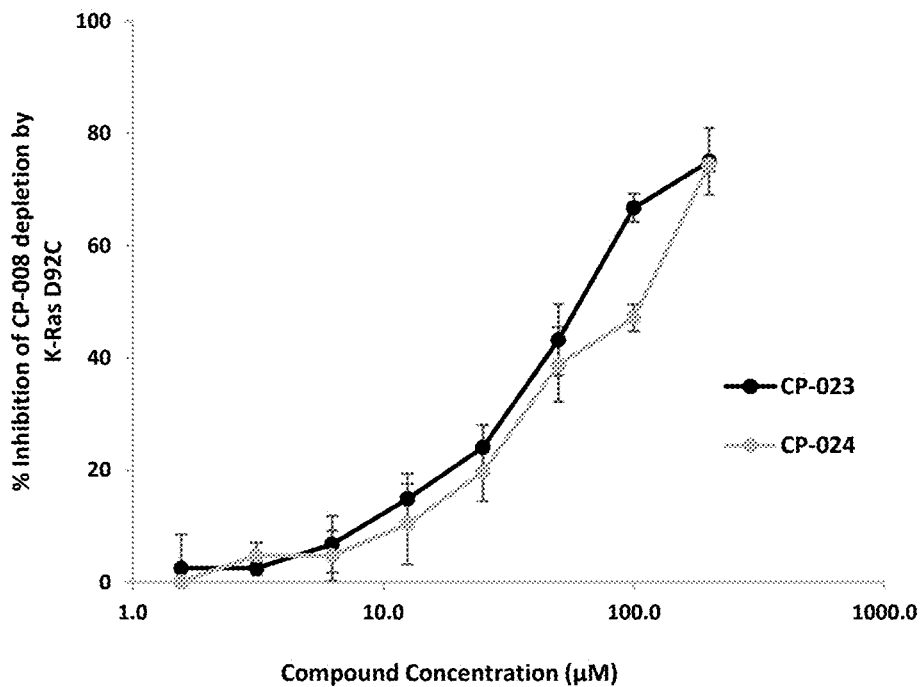
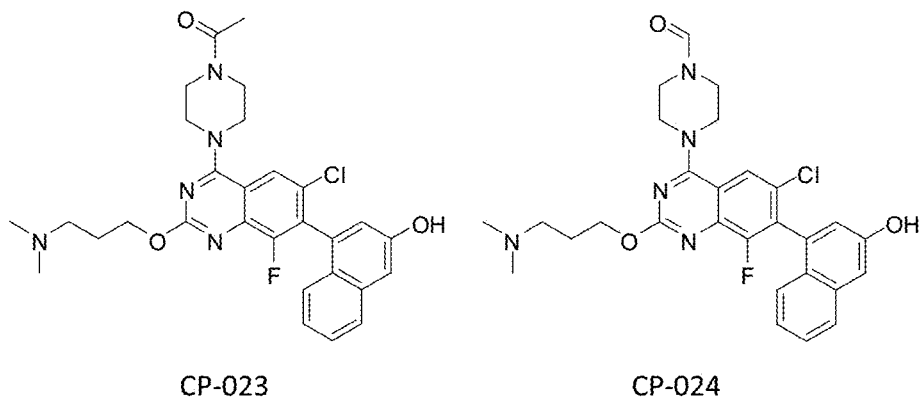
CP-023          CP-024
Fig. 6

SEQUENCE LISTING

<160> NUMBER OF SEQ ID NOS: 62

<210> SEQ ID NO 1
<211> LENGTH: 189
<212> TYPE: PRT
<213> ORGANISM: Homo sapiens

<400> SEQUENCE: 1

Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 2
<211> LENGTH: 188
<212> TYPE: PRT
<213> ORGANISM: Homo sapiens

<400> SEQUENCE: 2

Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr

```
                130             135             140
Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

<210> SEQ ID NO 3
<211> LENGTH: 189
<212> TYPE: PRT
<213> ORGANISM: Homo sapiens

<400> SEQUENCE: 3

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185
```

<210> SEQ ID NO 4
<211> LENGTH: 189
<212> TYPE: PRT
<213> ORGANISM: Homo sapiens

<400> SEQUENCE: 4

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
```

```
                    85                  90                  95

Arg Glu Gln Ile Lys Arg Val Lys Asp Ser Asp Val Pro Met Val
                100                 105                 110

Leu Val Gly Asn Lys Cys Asp Leu Pro Thr Arg Thr Val Asp Thr Lys
            115                 120                 125

Gln Ala His Glu Leu Ala Lys Ser Tyr Gly Ile Pro Phe Ile Glu Thr
        130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185

<210> SEQ ID NO 5
<211> LENGTH: 208
<212> TYPE: PRT
<213> ORGANISM: Homo sapiens

<400> SEQUENCE: 5

Met Ala Thr Ser Ala Val Pro Ser Asp Asn Leu Pro Thr Tyr Lys Leu
1               5                   10                  15

Val Val Val Gly Asp Gly Gly Val Gly Lys Ser Ala Leu Thr Ile Gln
            20                  25                  30

Phe Phe Gln Lys Ile Phe Val Pro Asp Tyr Asp Pro Thr Ile Glu Asp
        35                  40                  45

Ser Tyr Leu Lys His Thr Glu Ile Asp Asn Gln Trp Ala Ile Leu Asp
    50                  55                  60

Val Leu Asp Thr Ala Gly Gln Glu Glu Phe Ser Ala Met Arg Glu Gln
65                  70                  75                  80

Tyr Met Arg Thr Gly Asp Gly Phe Leu Ile Val Tyr Ser Val Thr Asp
                85                  90                  95

Lys Ala Ser Phe Glu His Val Asp Arg Phe His Gln Leu Ile Leu Arg
                100                 105                 110

Val Lys Asp Arg Glu Ser Phe Pro Met Ile Leu Val Ala Asn Lys Val
            115                 120                 125

Asp Leu Met His Leu Arg Lys Ile Thr Arg Glu Gln Gly Lys Glu Met
        130                 135                 140

Ala Thr Lys His Asn Ile Pro Tyr Ile Glu Thr Ser Ala Lys Asp Pro
145                 150                 155                 160

Pro Leu Asn Val Asp Lys Ala Phe His Asp Leu Val Arg Val Ile Arg
                165                 170                 175

Gln Gln Ile Pro Glu Lys Ser Gln Lys Lys Lys Lys Thr Lys Trp
            180                 185                 190

Arg Gly Asp Arg Ala Thr Gly Thr His Lys Leu Gln Cys Val Ile Leu
        195                 200                 205

<210> SEQ ID NO 6
<211> LENGTH: 233
<212> TYPE: PRT
<213> ORGANISM: Homo sapiens

<400> SEQUENCE: 6

Met Glu Leu Pro Thr Lys Pro Gly Thr Phe Asp Leu Gly Leu Ala Thr
1               5                   10                  15

Trp Ser Pro Ser Phe Gln Gly Glu Thr His Arg Ala Gln Ala Arg Arg
```

-continued

```
                20                  25                  30
Arg Asp Val Gly Arg Gln Leu Pro Glu Tyr Lys Ala Val Val Gly
                35                  40                  45
Ala Ser Gly Val Gly Lys Ser Ala Leu Thr Ile Gln Leu Asn His Gln
 50                  55                  60
Cys Phe Val Glu Asp His Asp Pro Thr Ile Gln Asp Ser Tyr Trp Lys
 65                  70                  75                  80
Glu Leu Thr Leu Asp Ser Gly Asp Cys Ile Leu Asn Val Leu Asp Thr
                85                  90                  95
Ala Gly Gln Ala Ile His Arg Ala Leu Arg Asp Gln Cys Leu Ala Val
                100                 105                 110
Cys Asp Gly Val Leu Gly Val Phe Ala Leu Asp Asp Pro Ser Ser Leu
                115                 120                 125
Ile Gln Leu Gln Gln Ile Trp Ala Thr Trp Gly Pro His Pro Ala Gln
                130                 135                 140
Pro Leu Val Leu Val Gly Asn Lys Cys Asp Leu Val Thr Thr Ala Gly
145                 150                 155                 160
Asp Ala His Ala Ala Ala Ala Leu Ala His Ser Trp Gly Ala His
                165                 170                 175
Phe Val Glu Thr Ser Ala Lys Thr Arg Gln Gly Val Glu Glu Ala Phe
                180                 185                 190
Ser Leu Leu Val His Glu Ile Gln Arg Val Gln Glu Ala Met Ala Lys
                195                 200                 205
Glu Pro Met Ala Arg Ser Cys Arg Glu Lys Thr Arg His Gln Lys Ala
                210                 215                 220
Thr Cys His Cys Gly Cys Ser Val Ala
225                 230

<210> SEQ ID NO 7
<211> LENGTH: 204
<212> TYPE: PRT
<213> ORGANISM: Homo sapiens

<400> SEQUENCE: 7

Met Ala Ala Gly Trp Arg Asp Gly Ser Gly Gln Glu Lys Tyr Arg
 1                   5                  10                  15
Leu Val Val Gly Gly Gly Val Gly Lys Ser Ala Leu Thr Ile
                20                  25                  30
Gln Phe Ile Gln Ser Tyr Phe Val Thr Asp Tyr Asp Pro Thr Ile Glu
                35                  40                  45
Asp Ser Tyr Thr Lys Gln Cys Val Ile Asp Asp Arg Ala Ala Arg Leu
 50                  55                  60
Asp Ile Leu Asp Thr Ala Gly Gln Glu Glu Phe Gly Ala Met Arg Glu
 65                  70                  75                  80
Gln Tyr Met Arg Thr Gly Glu Gly Phe Leu Leu Val Phe Ser Val Thr
                85                  90                  95
Asp Arg Gly Ser Phe Glu Glu Ile Tyr Lys Phe Gln Arg Gln Ile Leu
                100                 105                 110
Arg Val Lys Asp Arg Asp Glu Phe Pro Met Ile Leu Ile Gly Asn Lys
                115                 120                 125
Ala Asp Leu Asp His Gln Arg Gln Val Thr Gln Glu Glu Gly Gln Gln
                130                 135                 140
Leu Ala Arg Gln Leu Lys Val Thr Tyr Met Glu Ala Ser Ala Lys Ile
145                 150                 155                 160
```

Arg Met Asn Val Asp Gln Ala Phe His Glu Leu Val Arg Val Ile Arg
                165                 170                 175

Lys Phe Gln Glu Gln Glu Cys Pro Pro Ser Pro Glu Pro Thr Arg Lys
            180                 185                 190

Glu Lys Asp Lys Lys Gly Cys His Cys Val Ile Phe
        195                 200

<210> SEQ ID NO 8
<211> LENGTH: 206
<212> TYPE: PRT
<213> ORGANISM: Homo sapiens

<400> SEQUENCE: 8

Met Ala Ala Asn Lys Pro Lys Gly Gln Asn Ser Leu Ala Leu His Lys
1               5                   10                  15

Val Ile Met Val Gly Ser Gly Gly Val Gly Lys Ser Ala Leu Thr Leu
            20                  25                  30

Gln Phe Met Tyr Asp Glu Phe Val Glu Asp Tyr Glu Pro Thr Lys Ala
        35                  40                  45

Asp Ser Tyr Arg Lys Lys Val Val Leu Asp Gly Glu Glu Val Gln Ile
    50                  55                  60

Asp Ile Leu Asp Thr Ala Gly Gln Glu Asp Tyr Ala Ala Ile Arg Asp
65                  70                  75                  80

Asn Tyr Phe Arg Ser Gly Glu Gly Phe Leu Cys Val Phe Ser Ile Thr
                85                  90                  95

Glu Met Glu Ser Phe Ala Ala Thr Ala Asp Phe Arg Glu Gln Ile Leu
            100                 105                 110

Arg Val Lys Glu Asp Glu Asn Val Pro Phe Leu Leu Val Gly Asn Lys
        115                 120                 125

Ser Asp Leu Glu Asp Lys Arg Gln Val Ser Val Glu Glu Ala Lys Asn
    130                 135                 140

Arg Ala Glu Gln Trp Asn Val Asn Tyr Val Glu Thr Ser Ala Lys Thr
145                 150                 155                 160

Arg Ala Asn Val Asp Lys Val Phe Phe Asp Leu Met Arg Glu Ile Arg
                165                 170                 175

Ala Arg Lys Met Glu Asp Ser Lys Glu Lys Asn Gly Lys Lys Lys Arg
            180                 185                 190

Lys Ser Leu Ala Lys Arg Ile Arg Glu Arg Cys Cys Ile Leu
        195                 200                 205

<210> SEQ ID NO 9
<211> LENGTH: 206
<212> TYPE: PRT
<213> ORGANISM: Homo sapiens

<400> SEQUENCE: 9

Met Ala Ala Asn Lys Ser Lys Gly Gln Ser Ser Leu Ala Leu His Lys
1               5                   10                  15

Val Ile Met Val Gly Ser Gly Gly Val Gly Lys Ser Ala Leu Thr Leu
            20                  25                  30

Gln Phe Met Tyr Asp Glu Phe Val Glu Asp Tyr Glu Pro Thr Lys Ala
        35                  40                  45

Asp Ser Tyr Arg Lys Lys Val Val Leu Asp Gly Glu Glu Val Gln Ile
    50                  55                  60

Asp Ile Leu Asp Thr Ala Gly Gln Glu Asp Tyr Ala Ala Ile Arg Asp
65                  70                  75                  80

```
Asn Tyr Phe Arg Ser Gly Glu Gly Phe Leu Val Phe Ser Ile Thr
                85                  90                  95

Glu His Glu Ser Phe Thr Ala Thr Ala Glu Phe Arg Glu Gln Ile Leu
            100                 105                 110

Arg Val Lys Ala Glu Glu Asp Lys Ile Pro Leu Leu Val Val Gly Asn
        115                 120                 125

Lys Ser Asp Leu Glu Glu Arg Arg Gln Val Pro Val Glu Glu Ala Arg
130                 135                 140

Ser Lys Ala Glu Glu Trp Gly Val Gln Tyr Val Glu Thr Ser Ala Lys
145                 150                 155                 160

Thr Arg Ala Asn Val Asp Lys Val Phe Phe Asp Leu Met Arg Glu Ile
                165                 170                 175

Arg Thr Lys Lys Met Ser Glu Asn Lys Asp Lys Asn Gly Lys Lys Ser
            180                 185                 190

Ser Lys Asn Lys Lys Ser Phe Lys Glu Arg Cys Cys Leu Leu
        195                 200                 205
```

<210> SEQ ID NO 10
<211> LENGTH: 219
<212> TYPE: PRT
<213> ORGANISM: Homo sapiens

<400> SEQUENCE: 10

```
Met Asp Ser Gly Thr Arg Pro Val Gly Ser Cys Cys Ser Ser Pro Ala
1               5                   10                  15

Gly Leu Ser Arg Glu Tyr Lys Leu Val Met Leu Gly Ala Gly Gly Val
            20                  25                  30

Gly Lys Ser Ala Met Thr Met Gln Phe Ile Ser His Arg Phe Pro Glu
        35                  40                  45

Asp His Asp Pro Thr Ile Glu Asp Ala Tyr Lys Ile Arg Ile Arg Ile
    50                  55                  60

Asp Asp Glu Pro Ala Asn Leu Asp Ile Leu Asp Thr Ala Gly Gln Ala
65                  70                  75                  80

Glu Phe Thr Ala Met Arg Asp Gln Tyr Met Arg Ala Gly Glu Gly Phe
                85                  90                  95

Ile Ile Cys Tyr Ser Ile Thr Asp Arg Arg Ser Phe His Glu Val Arg
            100                 105                 110

Glu Phe Lys Gln Leu Ile Tyr Arg Val Arg Arg Thr Asp Asp Thr Pro
        115                 120                 125

Val Val Leu Val Gly Asn Lys Ser Asp Leu Lys Gln Leu Arg Gln Val
    130                 135                 140

Thr Lys Glu Glu Gly Leu Ala Leu Ala Arg Glu Phe Ser Cys Pro Phe
145                 150                 155                 160

Phe Glu Thr Ser Ala Ala Tyr Arg Tyr Tyr Ile Asp Asp Val Phe His
                165                 170                 175

Ala Leu Val Arg Glu Ile Arg Arg Lys Glu Lys Glu Ala Val Leu Ala
            180                 185                 190

Met Glu Lys Lys Ser Lys Pro Lys Asn Ser Val Trp Lys Arg Leu Lys
        195                 200                 205

Ser Pro Phe Arg Lys Lys Lys Asp Ser Val Thr
    210                 215
```

<210> SEQ ID NO 11
<211> LENGTH: 189
<212> TYPE: PRT
<213> ORGANISM: Homo sapiens

<400> SEQUENCE: 11

Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Cys Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 12
<211> LENGTH: 188
<212> TYPE: PRT
<213> ORGANISM: Homo sapiens

<400> SEQUENCE: 12

Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Cys Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Arg Val Glu Asp Ala Phe Tyr Thr Leu Val
145                 150                 155                 160

Arg Glu Ile Arg Lys His Lys Glu Lys Met Ser Lys Asp Gly Lys Lys
                165                 170                 175

```
Lys Lys Lys Lys Ser Lys Thr Lys Cys Val Ile Met
            180                 185

<210> SEQ ID NO 13
<211> LENGTH: 189
<212> TYPE: PRT
<213> ORGANISM: Homo sapiens

<400> SEQUENCE: 13

Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
            50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Cys Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
            130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 14
<211> LENGTH: 188
<212> TYPE: PRT
<213> ORGANISM: Homo sapiens

<400> SEQUENCE: 14

Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
            50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Cys Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125
```

Gln Ala Gln Asp Leu Ala Arg Ser Tyr Gly Ile Pro Phe Ile Glu Thr
            130                 135                 140

Ser Ala Lys Thr Arg Gln Arg Val Glu Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 15
<211> LENGTH: 189
<212> TYPE: PRT
<213> ORGANISM: Homo sapiens

<400> SEQUENCE: 15

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Cys Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
            130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 16
<211> LENGTH: 188
<212> TYPE: PRT
<213> ORGANISM: Homo sapiens

<400> SEQUENCE: 16

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
50                  55                  60

Ser Ala Met Arg Asp Gln Tyr Met Arg Thr Gly Glu Gly Phe Leu Cys
65                  70                  75                  80

```
Val Phe Ala Ile Asn Asn Thr Lys Ser Phe Glu Asp Ile His Cys Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
                180                 185

<210> SEQ ID NO 17
<211> LENGTH: 189
<212> TYPE: PRT
<213> ORGANISM: Homo sapiens

<400> SEQUENCE: 17

Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Cys Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 18
<211> LENGTH: 188
<212> TYPE: PRT
<213> ORGANISM: Homo sapiens

<400> SEQUENCE: 18

Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp Glu Tyr
                20                  25                  30
```

-continued

```
Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Cys Glu Tyr
    50                  55                  60

Ser Ala Met Arg Asp Gln Tyr Met Arg Thr Gly Glu Gly Phe Leu Cys
65              70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Arg Val Glu Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

<210> SEQ ID NO 19
<211> LENGTH: 189
<212> TYPE: PRT
<213> ORGANISM: Homo sapiens

<400> SEQUENCE: 19

```
Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65              70                  75                  80

Val Phe Ala Ile Asn Asn Thr Lys Ser Phe Glu Cys Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185
```

<210> SEQ ID NO 20
<211> LENGTH: 188
<212> TYPE: PRT

<213> ORGANISM: Homo sapiens

<400> SEQUENCE: 20

Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Cys Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 21
<211> LENGTH: 189
<212> TYPE: PRT
<213> ORGANISM: Homo sapiens

<400> SEQUENCE: 21

Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Cys Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys

```
                         165                 170                 175

Thr Pro Gly Cys Val Lys Ile Lys Lys Cys Ile Ile Met
            180                 185

<210> SEQ ID NO 22
<211> LENGTH: 188
<212> TYPE: PRT
<213> ORGANISM: Homo sapiens

<400> SEQUENCE: 22

Met Thr Glu Tyr Lys Leu Val Val Gly Ala Asp Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Cys Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
130                 135                 140

Ser Ala Lys Thr Arg Gln Arg Val Glu Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 23
<211> LENGTH: 206
<212> TYPE: PRT
<213> ORGANISM: Homo sapiens

<400> SEQUENCE: 23

Met Ala Ala Asn Lys Pro Lys Gly Gln Asn Ser Leu Ala Leu His Lys
1               5                   10                  15

Val Ile Met Val Gly Ser Cys Gly Val Gly Lys Ser Ala Leu Thr Leu
            20                  25                  30

Gln Phe Met Tyr Asp Glu Phe Val Glu Asp Tyr Glu Pro Thr Lys Ala
            35                  40                  45

Asp Ser Tyr Arg Lys Lys Val Val Leu Asp Gly Glu Glu Val Gln Ile
            50                  55                  60

Asp Ile Leu Asp Thr Ala Gly Gln Glu Asp Tyr Ala Ala Ile Arg Asp
65                  70                  75                  80

Asn Tyr Phe Arg Ser Gly Glu Gly Phe Leu Cys Val Phe Ser Ile Thr
                85                  90                  95

Glu Met Glu Ser Phe Ala Ala Thr Ala Asp Phe Arg Glu Gln Ile Leu
            100                 105                 110

Arg Val Lys Glu Asp Glu Asn Val Pro Phe Leu Leu Val Gly Asn Lys
```

115                 120                 125
Ser Asp Leu Glu Asp Lys Arg Gln Val Ser Val Glu Glu Ala Lys Asn
    130                 135                 140

Arg Ala Glu Gln Trp Asn Val Asn Tyr Val Glu Thr Ser Ala Lys Thr
145                 150                 155                 160

Arg Ala Asn Val Asp Lys Val Phe Phe Asp Leu Met Arg Glu Ile Arg
                165                 170                 175

Ala Arg Lys Met Glu Asp Ser Lys Glu Lys Asn Gly Lys Lys Lys Arg
            180                 185                 190

Lys Ser Leu Ala Lys Arg Ile Arg Glu Arg Cys Cys Ile Leu
    195                 200                 205

<210> SEQ ID NO 24
<211> LENGTH: 206
<212> TYPE: PRT
<213> ORGANISM: Homo sapiens

<400> SEQUENCE: 24

Met Ala Ala Asn Lys Ser Lys Gly Gln Ser Ser Leu Ala Leu His Lys
1               5                   10                  15

Val Ile Met Val Gly Ser Cys Gly Val Gly Lys Ser Ala Leu Thr Leu
            20                  25                  30

Gln Phe Met Tyr Asp Glu Phe Val Glu Asp Tyr Glu Pro Thr Lys Ala
        35                  40                  45

Asp Ser Tyr Arg Lys Lys Val Val Leu Asp Gly Glu Glu Val Gln Ile
    50                  55                  60

Asp Ile Leu Asp Thr Ala Gly Gln Glu Asp Tyr Ala Ala Ile Arg Asp
65                  70                  75                  80

Asn Tyr Phe Arg Ser Gly Glu Gly Phe Leu Leu Val Phe Ser Ile Thr
                85                  90                  95

Glu His Glu Ser Phe Thr Ala Thr Ala Glu Phe Arg Glu Gln Ile Leu
            100                 105                 110

Arg Val Lys Ala Glu Glu Asp Lys Ile Pro Leu Leu Val Val Gly Asn
        115                 120                 125

Lys Ser Asp Leu Glu Glu Arg Arg Gln Val Pro Val Glu Glu Ala Arg
    130                 135                 140

Ser Lys Ala Glu Glu Trp Gly Val Gln Tyr Val Glu Thr Ser Ala Lys
145                 150                 155                 160

Thr Arg Ala Asn Val Asp Lys Val Phe Phe Asp Leu Met Arg Glu Ile
                165                 170                 175

Arg Thr Lys Lys Met Ser Glu Asn Lys Asp Lys Asn Gly Lys Lys Ser
            180                 185                 190

Ser Lys Asn Lys Lys Ser Phe Lys Glu Arg Cys Cys Leu Leu
        195                 200                 205

<210> SEQ ID NO 25
<211> LENGTH: 173
<212> TYPE: PRT
<213> ORGANISM: Homo sapiens

<400> SEQUENCE: 25

Ser Leu Ala Leu His Lys Val Ile Met Val Gly Ser Cys Gly Val Gly
1               5                   10                  15

Lys Ser Ala Leu Thr Leu Gln Phe Met Tyr Asp Glu Phe Val Glu Asp
            20                  25                  30

Tyr Glu Pro Thr Lys Ala Asp Ser Tyr Arg Lys Lys Val Val Leu Asp

```
                35                  40                  45
Gly Glu Glu Val Gln Ile Asp Ile Leu Asp Thr Ala Gly Gln Glu Asp
 50                  55                  60

Tyr Ala Ala Ile Arg Asp Asn Tyr Phe Arg Ser Gly Glu Gly Phe Leu
65                  70                  75                  80

Cys Val Phe Ser Ile Thr Glu Met Glu Ser Phe Ala Ala Thr Ala Asp
                85                  90                  95

Phe Arg Glu Gln Ile Leu Arg Val Lys Glu Asp Glu Asn Val Pro Phe
            100                 105                 110

Leu Leu Val Gly Asn Lys Ser Asp Leu Glu Asp Lys Arg Gln Val Ser
        115                 120                 125

Val Glu Glu Ala Lys Asn Arg Ala Glu Gln Trp Asn Val Asn Tyr Val
    130                 135                 140

Glu Thr Ser Ala Lys Thr Arg Ala Asn Val Asp Lys Val Phe Phe Asp
145                 150                 155                 160

Leu Met Arg Glu Ile Arg Ala Arg Lys Met Glu Asp Ser
                165                 170

<210> SEQ ID NO 26
<211> LENGTH: 173
<212> TYPE: PRT
<213> ORGANISM: Homo sapiens

<400> SEQUENCE: 26

Ser Leu Ala Leu His Lys Val Ile Met Val Gly Ser Cys Gly Val Gly
1               5                   10                  15

Lys Ser Ala Leu Thr Leu Gln Phe Met Tyr Asp Glu Phe Val Glu Asp
            20                  25                  30

Tyr Glu Pro Thr Lys Ala Asp Ser Tyr Arg Lys Lys Val Val Leu Asp
        35                  40                  45

Gly Glu Glu Val Gln Ile Asp Ile Leu Asp Thr Ala Gly Gln Glu Asp
 50                  55                  60

Tyr Ala Ala Ile Arg Asp Asn Tyr Phe Arg Ser Gly Glu Gly Phe Leu
65                  70                  75                  80

Leu Val Phe Ser Ile Thr Glu His Glu Ser Phe Thr Ala Thr Ala Glu
                85                  90                  95

Phe Arg Glu Gln Ile Leu Arg Val Lys Ala Glu Glu Asp Lys Ile Pro
            100                 105                 110

Leu Leu Val Val Gly Asn Lys Ser Asp Leu Glu Glu Arg Arg Gln Val
        115                 120                 125

Pro Val Glu Glu Ala Arg Ser Lys Ala Glu Glu Trp Gly Val Gln Tyr
    130                 135                 140

Val Glu Thr Ser Ala Lys Thr Arg Ala Asn Val Asp Lys Val Phe Phe
145                 150                 155                 160

Asp Leu Met Arg Glu Ile Arg Thr Lys Lys Met Ser Glu
                165                 170

<210> SEQ ID NO 27
<211> LENGTH: 188
<212> TYPE: PRT
<213> ORGANISM: Homo sapiens

<400> SEQUENCE: 27

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
```

```
            20                  25                  30
Asp Pro Thr Ile Glu Asp Ser Tyr Arg Lys Gln Val Ile Asp Gly
        35                  40                  45

Glu Thr Cys Leu Leu Asp Ile Leu Asp Thr Ala Gly Gln Cys Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 28
<211> LENGTH: 188
<212> TYPE: PRT
<213> ORGANISM: Homo sapiens

<400> SEQUENCE: 28

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Cys Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 29
<211> LENGTH: 188
```

```
<212> TYPE: PRT
<213> ORGANISM: Homo sapiens

<400> SEQUENCE: 29

Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Cys Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
                180                 185

<210> SEQ ID NO 30
<211> LENGTH: 188
<212> TYPE: PRT
<213> ORGANISM: Homo sapiens

<400> SEQUENCE: 30

Met Thr Glu Tyr Lys Leu Val Val Gly Ala Asp Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Cys Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160
```

```
Arg Glu Ile Arg Lys His Lys Glu Lys Met Ser Lys Asp Gly Lys Lys
            165                 170                 175
Lys Lys Lys Lys Ser Lys Thr Lys Cys Val Ile Met
        180                 185

<210> SEQ ID NO 31
<211> LENGTH: 188
<212> TYPE: PRT
<213> ORGANISM: Homo sapiens

<400> SEQUENCE: 31

Met Thr Glu Tyr Lys Leu Val Val Val Gly Ala Asp Gly Val Gly Lys
1               5                   10                  15
Ser Ala Leu Thr Ile Gln Leu Ile Gln Asn His Phe Val Asp Glu Tyr
            20                  25                  30
Asp Pro Thr Ile Glu Asp Ser Tyr Arg Lys Gln Val Val Ile Asp Gly
        35                  40                  45
Glu Thr Cys Leu Leu Asp Ile Leu Asp Thr Ala Gly Gln Glu Glu Tyr
    50                  55                  60
Ser Ala Met Arg Asp Gln Tyr Met Arg Thr Gly Glu Gly Phe Leu Cys
65                  70                  75                  80
Val Phe Ala Ile Asn Asn Thr Lys Ser Phe Glu Cys Ile His His Tyr
                85                  90                  95
Arg Glu Gln Ile Lys Arg Val Lys Asp Ser Glu Asp Val Pro Met Val
            100                 105                 110
Leu Val Gly Asn Lys Cys Asp Leu Pro Ser Arg Thr Val Asp Thr Lys
        115                 120                 125
Gln Ala Gln Asp Leu Ala Arg Ser Tyr Gly Ile Pro Phe Ile Glu Thr
    130                 135                 140
Ser Ala Lys Thr Arg Gln Gly Val Asp Asp Ala Phe Tyr Thr Leu Val
145                 150                 155                 160
Arg Glu Ile Arg Lys His Lys Glu Lys Met Ser Lys Asp Gly Lys Lys
            165                 170                 175
Lys Lys Lys Lys Ser Lys Thr Lys Cys Val Ile Met
        180                 185

<210> SEQ ID NO 32
<211> LENGTH: 188
<212> TYPE: PRT
<213> ORGANISM: Homo sapiens

<400> SEQUENCE: 32

Met Thr Glu Tyr Lys Leu Val Val Val Gly Ala Asp Gly Val Gly Lys
1               5                   10                  15
Ser Ala Leu Thr Ile Gln Leu Ile Gln Asn His Phe Val Asp Glu Tyr
            20                  25                  30
Asp Pro Thr Ile Glu Asp Ser Tyr Arg Lys Gln Val Val Ile Asp Gly
        35                  40                  45
Glu Thr Cys Leu Leu Asp Ile Leu Asp Thr Ala Gly Gln Glu Glu Tyr
    50                  55                  60
Ser Ala Met Arg Asp Gln Tyr Met Arg Thr Gly Glu Gly Phe Leu Cys
65                  70                  75                  80
Val Phe Ala Ile Asn Asn Thr Lys Ser Phe Glu Asp Ile His Cys Tyr
                85                  90                  95
Arg Glu Gln Ile Lys Arg Val Lys Asp Ser Glu Asp Val Pro Met Val
            100                 105                 110
```

```
Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Ser Lys Thr Lys Cys Val Ile Met
            180                 185

<210> SEQ ID NO 33
<211> LENGTH: 169
<212> TYPE: PRT
<213> ORGANISM: Homo sapiens

<400> SEQUENCE: 33

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Cys Glu Tyr
50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Asp Val Pro Met Val
            100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys
                165

<210> SEQ ID NO 34
<211> LENGTH: 169
<212> TYPE: PRT
<213> ORGANISM: Homo sapiens

<400> SEQUENCE: 34

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
50                  55                  60

Ser Ala Met Arg Asp Gln Tyr Met Arg Thr Gly Glu Gly Phe Leu Cys
65                  70                  75                  80
```

```
Val Phe Ala Ile Asn Asn Thr Lys Ser Phe Glu Cys Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
            130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys
                165

<210> SEQ ID NO 35
<211> LENGTH: 169
<212> TYPE: PRT
<213> ORGANISM: Homo sapiens

<400> SEQUENCE: 35

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Cys Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
            130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys
                165

<210> SEQ ID NO 36
<211> LENGTH: 169
<212> TYPE: PRT
<213> ORGANISM: Homo sapiens

<400> SEQUENCE: 36

Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Cys Glu Tyr
        50                  55                  60
```

```
Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                 85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys
                165

<210> SEQ ID NO 37
<211> LENGTH: 169
<212> TYPE: PRT
<213> ORGANISM: Homo sapiens

<400> SEQUENCE: 37

Met Thr Glu Tyr Lys Leu Val Val Val Gly Ala Asp Gly Val Gly Lys
 1               5                  10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Cys Ile His His Tyr
                 85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys
                165

<210> SEQ ID NO 38
<211> LENGTH: 169
<212> TYPE: PRT
<213> ORGANISM: Homo sapiens

<400> SEQUENCE: 38

Met Thr Glu Tyr Lys Leu Val Val Val Gly Ala Asp Gly Val Gly Lys
 1               5                  10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45
```

```
Glu Thr Cys Leu Leu Asp Ile Leu Asp Thr Ala Gly Gln Glu Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His Cys Tyr
                 85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys
                165

<210> SEQ ID NO 39
<211> LENGTH: 169
<212> TYPE: PRT
<213> ORGANISM: Homo sapiens

<400> SEQUENCE: 39

Met Thr Glu Tyr Lys Leu Val Val Val Gly Ala Gly Gly Val Gly Lys
 1               5                  10                  15

Ser Ala Leu Thr Ile Gln Leu Ile Gln Asn His Phe Val Asp Glu Tyr
                 20                  25                  30

Asp Pro Thr Ile Glu Asp Ser Tyr Arg Lys Gln Val Val Ile Asp Gly
             35                  40                  45

Glu Thr Cys Leu Leu Asp Ile Leu Asp Thr Ala Gly Gln Cys Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                 85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys
                165

<210> SEQ ID NO 40
<211> LENGTH: 169
<212> TYPE: PRT
<213> ORGANISM: Homo sapiens

<400> SEQUENCE: 40

Met Thr Glu Tyr Lys Leu Val Val Val Gly Ala Gly Gly Val Gly Lys
 1               5                  10                  15

Ser Ala Leu Thr Ile Gln Leu Ile Gln Asn His Phe Val Asp Glu Tyr
                 20                  25                  30
```

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Cys Ile His His Tyr
                 85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
                115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys
                165

<210> SEQ ID NO 41
<211> LENGTH: 169
<212> TYPE: PRT
<213> ORGANISM: Homo sapiens

<400> SEQUENCE: 41

Met Thr Glu Tyr Lys Leu Val Val Val Gly Ala Gly Gly Val Gly Lys
 1               5                  10                  15

Ser Ala Leu Thr Ile Gln Leu Ile Gln Asn His Phe Val Asp Glu Tyr
                 20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His Cys Tyr
                 85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
                115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys
                165

<210> SEQ ID NO 42
<211> LENGTH: 169
<212> TYPE: PRT
<213> ORGANISM: Homo sapiens

<400> SEQUENCE: 42

Met Thr Glu Tyr Lys Leu Val Val Val Gly Ala Asp Gly Val Gly Lys
 1               5                  10                  15

```
Ser Ala Leu Thr Ile Gln Leu Ile Gln Asn His Phe Val Asp Glu Tyr
             20                  25                  30

Asp Pro Thr Ile Glu Asp Ser Tyr Arg Lys Gln Val Val Ile Asp Gly
         35                  40                  45

Glu Thr Cys Leu Leu Asp Ile Leu Asp Thr Ala Gly Gln Cys Glu Tyr
     50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                 85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys
                165

<210> SEQ ID NO 43
<211> LENGTH: 169
<212> TYPE: PRT
<213> ORGANISM: Homo sapiens

<400> SEQUENCE: 43

Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp Glu Tyr
             20                  25                  30

Asp Pro Thr Ile Glu Asp Ser Tyr Arg Lys Gln Val Val Ile Asp Gly
         35                  40                  45

Glu Thr Cys Leu Leu Asp Ile Leu Asp Thr Ala Gly Gln Glu Glu Tyr
     50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Cys Ile His His Tyr
                 85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys
                165

<210> SEQ ID NO 44
<211> LENGTH: 169
<212> TYPE: PRT
<213> ORGANISM: Homo sapiens

<400> SEQUENCE: 44
```

```
Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65              70                  75                  80

Val Phe Ala Ile Asn Asn Thr Lys Ser Phe Glu Asp Ile His Cys Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145             150                 155                 160

Arg Glu Ile Arg Lys His Lys Glu Lys
                165
```

<210> SEQ ID NO 45
<211> LENGTH: 127
<212> TYPE: PRT
<213> ORGANISM: Homo sapiens

<400> SEQUENCE: 45

```
Met Arg Glu Gln Tyr Met Arg Thr Gly Glu Gly Phe Leu Leu Val Phe
1               5                   10                  15

Ser Val Thr Asp Arg Gly Ser Phe Glu Glu Ile Tyr Lys Phe Gln Arg
            20                  25                  30

Gln Ile Leu Arg Val Lys Asp Arg Asp Glu Phe Pro Met Ile Leu Ile
        35                  40                  45

Gly Asn Lys Ala Asp Leu Asp His Gln Arg Gln Val Thr Gln Glu Glu
    50                  55                  60

Gly Gln Gln Leu Ala Arg Gln Leu Lys Val Thr Tyr Met Glu Ala Ser
65              70                  75                  80

Ala Lys Ile Arg Met Asn Val Asp Gln Ala Phe His Glu Leu Val Arg
                85                  90                  95

Val Ile Arg Lys Phe Gln Glu Gln Glu Cys Pro Pro Ser Pro Glu Pro
            100                 105                 110

Thr Arg Lys Glu Lys Asp Lys Lys Gly Cys His Cys Val Ile Phe
            115                 120                 125
```

<210> SEQ ID NO 46
<211> LENGTH: 169
<212> TYPE: PRT
<213> ORGANISM: Homo sapiens

<400> SEQUENCE: 46

```
Met Ser Tyr Phe Val Thr Asp Tyr Asp Pro Thr Ile Glu Asp Ser Tyr
1               5                   10                  15

Thr Lys Gln Cys Val Ile Asp Asp Arg Ala Ala Arg Leu Asp Ile Leu
            20                  25                  30
```

```
Asp Thr Ala Gly Gln Glu Glu Phe Gly Ala Met Arg Glu Gln Tyr Met
            35                  40                  45

Arg Thr Gly Glu Gly Phe Leu Leu Val Phe Ser Val Thr Asp Arg Gly
 50                  55                  60

Ser Phe Glu Glu Ile Tyr Lys Phe Gln Arg Gln Ile Leu Arg Val Lys
 65                  70                  75                  80

Asp Arg Asp Glu Phe Pro Met Ile Leu Ile Gly Asn Lys Ala Asp Leu
                     85                  90                  95

Asp His Gln Arg Gln Val Thr Gln Glu Gly Gln Gln Leu Ala Arg
                100                 105                 110

Gln Leu Lys Val Thr Tyr Met Glu Ala Ser Ala Lys Ile Arg Met Asn
            115                 120                 125

Val Asp Gln Ala Phe His Glu Leu Val Arg Val Ile Arg Lys Phe Gln
130                 135                 140

Glu Gln Glu Cys Pro Pro Ser Pro Glu Pro Thr Arg Lys Glu Lys Asp
145                 150                 155                 160

Lys Lys Gly Cys His Cys Val Ile Phe
                165

<210> SEQ ID NO 47
<211> LENGTH: 236
<212> TYPE: PRT
<213> ORGANISM: Homo sapiens

<400> SEQUENCE: 47

Met Glu Arg Trp Leu Phe Leu Gly Ala Thr Glu Glu Gly Pro Lys Arg
 1               5                  10                  15

Thr Met Asp Ser Gly Thr Arg Pro Val Gly Ser Cys Ser Ser Pro
            20                  25                  30

Ala Gly Leu Ser Arg Glu Tyr Lys Leu Val Met Leu Gly Ala Gly Gly
            35                  40                  45

Val Gly Lys Ser Ala Met Thr Met Gln Phe Ile Ser His Arg Phe Pro
 50                  55                  60

Glu Asp His Asp Pro Thr Ile Glu Asp Ala Tyr Lys Ile Arg Ile Arg
 65                  70                  75                  80

Ile Asp Asp Glu Pro Ala Asn Leu Asp Ile Leu Asp Thr Ala Gly Gln
                 85                  90                  95

Ala Glu Phe Thr Ala Met Arg Asp Gln Tyr Met Arg Ala Gly Glu Gly
                100                 105                 110

Phe Ile Ile Cys Tyr Ser Ile Thr Asp Arg Arg Ser Phe His Glu Val
            115                 120                 125

Arg Glu Phe Lys Gln Leu Ile Tyr Arg Val Arg Arg Thr Asp Asp Thr
130                 135                 140

Pro Val Val Leu Val Gly Asn Lys Ser Asp Leu Lys Gln Leu Arg Gln
145                 150                 155                 160

Val Thr Lys Glu Glu Gly Leu Ala Leu Ala Arg Glu Phe Ser Cys Pro
                165                 170                 175

Phe Phe Glu Thr Ser Ala Ala Tyr Arg Tyr Tyr Ile Asp Asp Val Phe
            180                 185                 190

His Ala Leu Val Arg Glu Ile Arg Arg Lys Glu Lys Glu Ala Val Leu
            195                 200                 205

Ala Met Glu Lys Lys Ser Lys Pro Lys Asn Ser Val Trp Lys Arg Leu
210                 215                 220

Lys Ser Pro Phe Arg Lys Lys Lys Asp Ser Val Thr
225                 230                 235
```

```
<210> SEQ ID NO 48
<211> LENGTH: 183
<212> TYPE: PRT
<213> ORGANISM: Homo sapiens

<400> SEQUENCE: 48

Met Thr Met Gln Phe Ile Ser His Arg Phe Pro Glu Asp His Asp Pro
1               5                   10                  15

Thr Ile Glu Asp Ala Tyr Lys Ile Arg Ile Arg Ile Asp Glu Pro
            20                  25                  30

Ala Asn Leu Asp Ile Leu Asp Thr Ala Gly Gln Ala Glu Phe Thr Ala
        35                  40                  45

Met Arg Asp Gln Tyr Met Arg Ala Gly Glu Gly Phe Ile Ile Cys Tyr
50                  55                  60

Ser Ile Thr Asp Arg Arg Ser Phe His Glu Val Arg Glu Phe Lys Gln
65                  70                  75                  80

Leu Ile Tyr Arg Val Arg Arg Thr Asp Asp Thr Pro Val Val Leu Val
                85                  90                  95

Gly Asn Lys Ser Asp Leu Lys Gln Leu Arg Gln Val Thr Lys Glu Glu
            100                 105                 110

Gly Leu Ala Leu Ala Arg Glu Phe Ser Cys Pro Phe Phe Glu Thr Ser
        115                 120                 125

Ala Ala Tyr Arg Tyr Tyr Ile Asp Asp Val Phe His Ala Leu Val Arg
    130                 135                 140

Glu Ile Arg Arg Lys Glu Lys Glu Ala Val Leu Ala Met Glu Lys Lys
145                 150                 155                 160

Ser Lys Pro Lys Asn Ser Val Trp Lys Arg Leu Lys Ser Pro Phe Arg
                165                 170                 175

Lys Lys Lys Asp Ser Val Thr
            180

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 49

His His His His His His
1               5

<210> SEQ ID NO 50
<211> LENGTH: 51
<212> TYPE: PRT
<213> ORGANISM: Homo sapiens

<400> SEQUENCE: 50

Leu Asp Thr Ala Gly Gln Glu Glu Tyr Ser Ala Met Arg Asp Gln Tyr
1               5                   10                  15

Met Arg Thr Gly Glu Gly Phe Leu Cys Val Phe Ala Ile Asn Asn Thr
            20                  25                  30

Lys Ser Phe Glu Asp Ile His His Tyr Arg Glu Gln Ile Lys Arg Val
        35                  40                  45

Lys Asp Ser
    50
```

<210> SEQ ID NO 51
<211> LENGTH: 51
<212> TYPE: PRT
<213> ORGANISM: Homo sapiens

<400> SEQUENCE: 51

Leu Asp Thr Ala Gly Gln Glu Glu Tyr Ser Ala Met Arg Asp Gln Tyr
1               5                   10                  15

Met Arg Thr Gly Glu Gly Phe Leu Cys Val Phe Ala Ile Asn Asn Thr
            20                  25                  30

Lys Ser Phe Glu Asp Ile His Gln Tyr Arg Glu Gln Ile Lys Arg Val
        35                  40                  45

Lys Asp Ser
    50

<210> SEQ ID NO 52
<211> LENGTH: 51
<212> TYPE: PRT
<213> ORGANISM: Homo sapiens

<400> SEQUENCE: 52

Leu Asp Thr Ala Gly Gln Glu Glu Tyr Ser Ala Met Arg Asp Gln Tyr
1               5                   10                  15

Met Arg Thr Gly Glu Gly Phe Leu Cys Val Phe Ala Ile Asn Asn Ser
            20                  25                  30

Lys Ser Phe Ala Asp Ile Asn Leu Tyr Arg Glu Gln Ile Lys Arg Val
        35                  40                  45

Lys Asp Ser
    50

<210> SEQ ID NO 53
<211> LENGTH: 51
<212> TYPE: PRT
<213> ORGANISM: Homo sapiens

<400> SEQUENCE: 53

Leu Asp Thr Ala Gly Gln Glu Glu Phe Ser Ala Met Arg Glu Gln Tyr
1               5                   10                  15

Met Arg Thr Gly Asp Gly Phe Leu Ile Val Tyr Ser Val Thr Asp Lys
            20                  25                  30

Ala Ser Phe Glu His Val Asp Arg Phe His Gln Leu Ile Leu Arg Val
        35                  40                  45

Lys Asp Arg
    50

<210> SEQ ID NO 54
<211> LENGTH: 48
<212> TYPE: PRT
<213> ORGANISM: Homo sapiens

<400> SEQUENCE: 54

Leu Asp Thr Ala Gly Gln Ala Ile His Arg Ala Leu Arg Asp Gln Cys
1               5                   10                  15

Leu Ala Val Cys Asp Gly Val Leu Gly Val Phe Ala Leu Asp Asp Pro
            20                  25                  30

Ser Ser Leu Ile Gln Leu Gln Gln Ile Trp Ala Thr Trp Gly Pro His
        35                  40                  45

<210> SEQ ID NO 55

```
<211> LENGTH: 51
<212> TYPE: PRT
<213> ORGANISM: Homo sapiens

<400> SEQUENCE: 55

Leu Asp Thr Ala Gly Gln Glu Glu Phe Gly Ala Met Arg Glu Gln Tyr
1               5                   10                  15

Met Arg Thr Gly Glu Gly Phe Leu Leu Val Phe Ser Val Thr Asp Arg
            20                  25                  30

Gly Ser Phe Glu Glu Ile Tyr Lys Phe Gln Arg Gln Ile Leu Arg Val
        35                  40                  45

Lys Asp Arg
    50

<210> SEQ ID NO 56
<211> LENGTH: 51
<212> TYPE: PRT
<213> ORGANISM: Homo sapiens

<400> SEQUENCE: 56

Leu Asp Thr Ala Gly Gln Glu Asp Tyr Ala Ala Ile Arg Asp Asn Tyr
1               5                   10                  15

Phe Arg Ser Gly Glu Gly Phe Leu Cys Val Phe Ser Ile Thr Glu Met
            20                  25                  30

Glu Ser Phe Ala Ala Thr Ala Asp Phe Arg Glu Gln Ile Leu Arg Val
        35                  40                  45

Lys Glu Asp
    50

<210> SEQ ID NO 57
<211> LENGTH: 51
<212> TYPE: PRT
<213> ORGANISM: Homo sapiens

<400> SEQUENCE: 57

Leu Asp Thr Ala Gly Gln Ala Glu Phe Thr Ala Met Arg Asp Gln Tyr
1               5                   10                  15

Met Arg Ala Gly Glu Gly Phe Ile Ile Cys Tyr Ser Ile Thr Asp Arg
            20                  25                  30

Arg Ser Phe His Glu Val Arg Glu Phe Lys Gln Leu Ile Tyr Arg Val
        35                  40                  45

Arg Arg Thr
    50

<210> SEQ ID NO 58
<211> LENGTH: 108
<212> TYPE: PRT
<213> ORGANISM: Homo sapiens

<400> SEQUENCE: 58

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
```

```
                65                  70                  75                  80
Val Phe Ala Ile Asn Asn Thr Lys Ser Phe Glu Asp Ile His His Tyr
                    85                  90                  95

Arg Glu Gln Ile Lys Arg Val Lys Asp Ser Glu Asp
                100                 105

<210> SEQ ID NO 59
<211> LENGTH: 108
<212> TYPE: PRT
<213> ORGANISM: Homo sapiens

<400> SEQUENCE: 59

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                    85                  90                  95

Arg Glu Gln Ile Lys Arg Val Lys Asp Ser Asp Asp
                100                 105

<210> SEQ ID NO 60
<211> LENGTH: 108
<212> TYPE: PRT
<213> ORGANISM: Homo sapiens

<400> SEQUENCE: 60

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                    85                  90                  95

Arg Glu Gln Ile Lys Arg Val Lys Asp Ser Asp Asp
                100                 105

<210> SEQ ID NO 61
<211> LENGTH: 119
<212> TYPE: PRT
<213> ORGANISM: Homo sapiens

<400> SEQUENCE: 61

Met Ala Ala Asn Lys Pro Lys Gly Gln Asn Ser Leu Ala Leu His Lys
1               5                   10                  15

Val Ile Met Val Gly Ser Gly Gly Val Gly Lys Ser Ala Leu Thr Leu
                20                  25                  30
```

```
Gln Phe Met Tyr Asp Glu Phe Val Glu Asp Tyr Glu Pro Thr Lys Ala
            35                  40                  45

Asp Ser Tyr Arg Lys Lys Val Val Leu Asp Gly Glu Glu Val Gln Ile
    50                  55                  60

Asp Ile Leu Asp Thr Ala Gly Gln Glu Asp Tyr Ala Ala Ile Arg Asp
65                  70                  75                  80

Asn Tyr Phe Arg Ser Gly Glu Gly Phe Leu Cys Val Phe Ser Ile Thr
                85                  90                  95

Glu Met Glu Ser Phe Ala Ala Thr Ala Asp Phe Arg Glu Gln Ile Leu
                100                 105                 110

Arg Val Lys Glu Asp Glu Asn
            115

<210> SEQ ID NO 62
<211> LENGTH: 120
<212> TYPE: PRT
<213> ORGANISM: Homo sapiens

<400> SEQUENCE: 62

Met Ala Ala Asn Lys Ser Lys Gly Gln Ser Ser Leu Ala Leu His Lys
1               5                   10                  15

Val Ile Met Val Gly Ser Gly Gly Val Gly Lys Ser Ala Leu Thr Leu
            20                  25                  30

Gln Phe Met Tyr Asp Glu Phe Val Glu Asp Tyr Glu Pro Thr Lys Ala
            35                  40                  45

Asp Ser Tyr Arg Lys Lys Val Val Leu Asp Gly Glu Glu Val Gln Ile
    50                  55                  60

Asp Ile Leu Asp Thr Ala Gly Gln Glu Asp Tyr Ala Ala Ile Arg Asp
65                  70                  75                  80

Asn Tyr Phe Arg Ser Gly Glu Gly Phe Leu Leu Val Phe Ser Ile Thr
                85                  90                  95

Glu His Glu Ser Phe Thr Ala Thr Ala Glu Phe Arg Glu Gln Ile Leu
                100                 105                 110

Arg Val Lys Ala Glu Glu Asp Lys
            115                 120
```

US 9,810,690 B2

METHOD FOR SCREENING INHIBITORS OF RAS

CROSS-REFERENCE

This application is a continuation-in-part application of International Patent Application No. PCT/US2016/057774, filed on Oct. 19, 2016, which application claims priority to U.S. Provisional Patent Application No. 62/243,439, filed on Oct. 19, 2015, each of which is herein incorporated by reference in its entirety.

SEQUENCE LISTING

The instant application contains a Sequence Listing which has been submitted electronically in ASCII format and is hereby incorporated by reference in its entirety. Said ASCII copy, created on Dec. 22, 2016, is named 43683-713_501_SL.txt and is 88,631 bytes in size.

BACKGROUND OF THE INVENTION

Mutations in Ras proteins such as KRAS, HRAS, and NRAS are common oncogenic mutations present in human malignancies, including but not limited to colorectal cancer, lung cancer, thyroid cancer, and ovarian cancer. While Ras, in particular KRAS, has been well known as a primary cancer causing protein for more than 30 years, no effective treatments for Ras mutant tumors are currently available. The pharmaceutical industry has invested tremendous resources into the development of Ras and Ras pathway inhibitors with limited success to date. Recently, drugs have been approved targeting kinases involved in signal transduction downstream of Ras (e.g., RAF and MEK kinases). However, even in these cases, their effectiveness in Ras mutant tumors remains to be demonstrated.

Direct targeting of Ras has been deemed unfeasible for many years due to multiple failed attempts and a perception that the protein lacks druggable binding pockets. While crystal structures of Ras are generally consistent with a lack of clearly deep binding pockets, some portions of the protein are highly flexible (switch regions) and may adopt conformations favorable for small molecule drug binding. Exhaustive exploration of chemical space to identify potential direct Ras inhibitors has to date been prevented in part by a lack of robust high throughput assays suitable for screening. Assays used to identify direct Ras inhibitors have either relied on nuclear magnetic resonance (NMR) spectroscopy, or a combination of computational screening or design coupled with relatively low throughput Ras functional assays such as nucleotide exchange or effector binding. These methods do not allow for an unbiased screen of a large compound library. In addition, particularly for NMR and other unbiased binding assays, significant effort is typically made for each hit molecule or class to determine whether the binding event will lead to inhibition of Ras activity.

SUMMARY OF THE INVENTION

There exists a considerable need for high throughput compatible screening methodologies for identifying binders to Ras at sites known to alter Ras function. The present disclosure provides assay strategies that enable robust and high throughput interrogation of Ras binding, such as in the Switch II binding pocket, and provides other advantages as well. This pocket has been shown to inhibit Ras function both biochemically and in cells (see e.g., Ostrem, J. M.; Peters, U.; Sos, M. L.; Wells, J. A.; Shokat, K. M. *Nature* 2013, 503, 548-551, which is entirely incorporated herein by reference). The assays are amenable to the predominant oncogenic mutations in any isoform of Ras (e.g., KRAS, HRAS, and NRAS). Unlike previously Ras binding assays, the methods described herein provide a direct measure of binding to a specific site on Ras (e.g., the Switch II pocket) that is targetable by small molecules and has been shown to affect Ras function. The method also presents advantages over in vitro functional assays (e.g., nucleotide exchange, effector binding) in its ease of implementation, its throughput, and the fact that it can specifically identify direct Ras binders with a very low possibility of showing hits from compounds with indirect effects (e.g., binding to Ras effectors or binding to protein complex interfaces). The present disclosure provides methods, compositions, reaction mixtures, mutant Ras proteins, kits, substrates, and systems for selecting a Ras antagonist, with high specificity and sensitivity. Selection of Ras antagonists according to the disclosure is significantly higher in throughput and efficiency.

In one aspect, the present disclosure provides a method of selecting a Ras antagonist. In some embodiments, the method comprises: (a) combining in a reaction mixture a mutant Ras, a competition probe, and a test compound; and (b) detecting a decrease in binding between the mutant Ras and the competition probe as compared to binding of the competition probe to the mutant Ras in the absence of the test compound; wherein: (i) the mutant Ras comprises a cysteine mutation; (ii) the competition probe is capable of binding and covalently modifying the mutant Ras; and (iii) the decrease in binding between the mutant Ras and the competition probe is indicative of Ras antagonist activity of the test compound. In some embodiments, the competition probe competes for binding in the Switch II pocket of the mutant Ras. In some embodiments, the competition probe is capable of covalently modifying the mutant Ras by reacting with the cysteine residue of the cysteine mutation. In some embodiments, the competition probe is selected from a compound in Table 2 or Table 3. In some embodiments, the competition probe is selected from the group consisting of CP-001, CP-002, CP-003, CP-004, CP-005, CP-006, CP-007, CP-008, CP-009, CP-010, CP-011, CP-012, CP-013, CP-014, CP-015, CP-016, CP-017, CP-018, CP-019, CP-020, and any combination thereof. In some embodiments, the cysteine mutation is not at position 12 or 13 relative to SEQ ID NO: 1 or SEQ ID NO: 2 when optimally aligned. In some embodiments, the cysteine mutation is at position 12 or 13 relative to SEQ ID NO: 1 or SEQ ID NO: 2 when optimally aligned. In some embodiments, the cysteine mutation is at position 12 or 13 relative to SEQ ID NO: 1 when optimally aligned, and the mutant Ras is selected from the group consisting of MRAS, ERAS, RRAS2, RALA, RALB, RIT1, and any combination thereof. In some embodiments, the cysteine mutation is at a non-conserved amino acid position. In some embodiments, the cysteine mutation is a mutation relative to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, or SEQ ID NO: 48 when optimally aligned. In some embodiments, the cysteine mutation is at position 62 relative to SEQ ID NO: 1 or SEQ ID NO: 2 when optimally aligned (e.g., E62C in KRAS, HRAS, or NRAS; E72C in MRAS; A100C in ERAS; E73C in RRAS2, RALA, or RALB; A80C in RIT1), position 92 relative to SEQ ID NO: 1 or SEQ ID NO: 2 when optimally aligned (e.g., D92C in KRAS, HRAS, or NRAS; H102C in MRAS; Q130C in ERAS; E103C in RRAS2; A103C in RALA or RALB; E110C in RIT1), or position 95 relative to SEQ ID NO: 1 or SEQ ID NO: 2 when optimally aligned (e.g., H95C in KRAS; Q95C in HRAS; L95C in NRAS; R105C in MRAS; Q133C in ERAS; K106C in RRAS2; D106C in RALA; E106C in RALB; E113C in RIT1). In some embodiments, the mutant Ras is a mutant Ras subfamily protein. In some embodiments, the Ras is a Ras subfamily protein. In some embodiments, the mutant Ras is selected from the group consisting of mutant KRAS, mutant HRAS, mutant NRAS, mutant MRAS, mutant ERAS, mutant RRAS2, mutant RALA, mutant RALB, mutant RIT1, and any combination thereof. In some embodiments, the Ras is selected from the group consisting of KRAS, HRAS, NRAS, MRAS, ERAS, RRAS2, RALA, RALB, RIT1, and any combination thereof. In some embodiments, the mutant KRAS is a mutant KRAS isoform a or a mutant KRAS isoform b. In some embodiments, the mutant RRAS2 is a mutant RRAS2 isoform a, a mutant RRAS2 isoform b, or a mutant RRAS2 isoform c. In some embodiments, the mutant RIT1 is a mutant RIT1 isoform 1, a mutant RIT1 isoform 2, or a mutant RIT1 isoform 3. In some embodiments, the mutant Ras comprises one or more additional mutations. In some embodiments, the mutant Ras is selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, and any combination thereof.

In some embodiments, the subject method utilizes a KRAS double mutant based on SEQ ID NO: 1, in which positions 12 and 92 are substituted as G12D and D92C. In some embodiments, the subject method utilizes a KRAS double mutant based on SEQ ID NO: 1, in which positions 12 and 95 are substituted as G12D and H95C. In some embodiments, the subject method utilizes a KRAS mutant having a sequence shown in SEQ ID NO: 17, SEQ ID NO: 19, SEQ ID NO: 21, SEQ ID NO: 36, SEQ ID NO: 37, or SEQ ID NO: 38. In some embodiments, the subject method utilizes a KRAS double mutant based on SEQ ID NO: 2, in which positions 12 and 92 are substituted as G12D and D92C. In some embodiments, the subject method utilizes a KRAS double mutant based on SEQ ID NO: 2, in which positions 12 and 95 are substituted as G12D and H95C. In some embodiments, the subject method utilizes a KRAS mutant having a sequence shown in SEQ ID NO: 30, SEQ ID NO: 31, SEQ ID NO: 32, SEQ ID NO: 42, SEQ ID NO: 43 or SEQ ID NO: 44.

In some embodiments, the test compound interacts with Ras via a chemical bond selected from the group consisting of a hydrogen bond, van der Waals interaction, ionic bond, covalent bond, hydrophobic interaction, and any combination thereof. In some embodiments, the test compound interacts with the Switch II binding pocket of Ras. In some embodiments, the test compound binds to a GDP-bound Ras protein with a $K_d$ of at most 100 thereby antagonizing Ras activity. In some embodiments, antagonizing Ras activity comprises modulating GTPase activity, nucleotide exchange, effector protein binding, effector protein activation, guanine exchange factor (GEF) binding, GEF-facilitated nucleotide exchange, phosphate release, nucleotide release, nucleotide binding, Ras subcellular localization, Ras post-translational processing, or Ras post-translational modification. In some embodiments, the test compound inhibits the binding or release of GDP or GTP to a Ras protein. In some embodiments, the test compound is selected from the group consisting of CP-023 (1-(4-(6-chloro-2-(3-(dimethylamino)propoxy)-8-fluoro-7-(3-hydroxynaphthalen-1-yl)quinazolin-4-yl)piperazin-1-yl)ethanone), CP-024 (4-(6-chloro-2-(3-(dimethylamino)propoxy)-8-fluoro-7-(3-hydroxynaphthalen-1-yl)quinazolin-4-yl)piperazine-1-carbaldehyde), and any combination thereof. In some embodiments, detecting the decrease in binding comprises measuring the fraction of Ras covalently modified by the competition probe as determined by mass spectrometry.

In one aspect, the disclosure provides a method of producing a Ras antagonist. In some embodiments, the method comprises selecting the Ras antagonist according to any of the methods described herein, and synthesizing the compound.

In one aspect, the disclosure provides a pharmaceutical composition comprising a Ras antagonist or pharmaceutically acceptable salt thereof selected according to any of the methods described herein.

In one aspect, the disclosure provides a reaction mixture comprising a mutant Ras, a competition probe that is capable of binding the mutant Ras, and a test compound. In some embodiments, the mutant Ras comprises a cysteine mutation; the competition probe is capable of covalently modifying the mutant Ras at the cysteine mutation; and the test compound inhibits covalent modification of the mutant Ras by the competition probe. In some embodiments, the competition probe competes for binding in the Switch II pocket of the mutant Ras. In some embodiments, the cysteine mutation is not at position 12 or 13 relative to SEQ ID NO: 1 or SEQ ID NO: 2 when optimally aligned. In some embodiments, the cysteine mutation is at position 12 or 13 relative to SEQ ID NO: 1 or SEQ ID NO: 2 when optimally aligned. In some embodiments, the cysteine mutation is at position 12 or 13 relative to SEQ ID NO: 1 when optimally aligned, and the mutant Ras is selected from mutant MRAS, mutant ERAS, mutant RRAS2, mutant RALA, mutant RALB, mutant RIT1, and any combination thereof. In some embodiments, the cysteine mutation is at a non-conserved amino acid position. In some embodiments, the cysteine mutation is at position 62 relative to SEQ ID NO: 1 or SEQ ID NO: 2 when optimally aligned (e.g., E62C in KRAS, HRAS, or NRAS; E72C in MRAS; A100C in ERAS; E73C in RRAS2, RALA, or RALB; A80C in RIT1), position 92 relative to SEQ ID NO: 1 or SEQ ID NO: 2 when optimally aligned (e.g., D92C in KRAS, HRAS, or NRAS; H102C in MRAS; Q130C in ERAS; E103C in RRAS2; A103C in RALA or RALB; E110C in RIT1), or position 95 relative to SEQ ID NO: 1 or SEQ ID NO: 2 when optimally aligned (e.g., H95C in KRAS; Q95C in HRAS; L95C in NRAS; R105C in MRAS; Q133C in ERAS; K106C in RRAS2; D106C in RALA; E106C in RALB; E113C in RIT1). In some embodiments, the mutant Ras is selected from the group consisting of mutant KRAS, mutant HRAS, mutant NRAS, mutant MRAS, mutant ERAS, mutant RRAS2, mutant RALA, mutant RALB, mutant RIT1, and any combination thereof. In some embodiments, the mutant KRAS is a mutant KRAS isoform a or a mutant KRAS isoform b. In some embodiments, the mutant RRAS2 is a mutant RRAS2 isoform a, a mutant RRAS2 isoform b, or a mutant RRAS2 isoform c. In some embodiments, the mutant RIT1 is a mutant RIT1 isoform 1, a mutant RIT1 isoform 2, or a mutant RIT1 isoform 3. In some embodiments, the mutant Ras is selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, and any combination thereof. In some embodiments, the mutant Ras comprises one or more additional mutations. In some embodiments, the test compound interacts with Ras via a chemical bond selected from the group consisting of a hydrogen bond, van der Waals interaction, ionic bond, covalent bond, hydrophobic interaction, and any combination thereof. In some embodiments, the test compound interacts with the Switch II binding pocket of Ras. In some embodiments, the test compound is selected from the group consisting of CP-023 (1-(4-(6-chloro-2-(3-(dimethylamino)propoxy)-8-fluoro-7-(3-hydroxynaphthalen-1-yl)quinazolin-4-yl)piperazin-1-yl)ethanone), CP-024 (4-(6-chloro-2-(3-(dimethylamino)propoxy)-8-fluoro-7-(3-hydroxynaphthalen-1-yl)quinazolin-4-yl)piperazine-1-carbaldehyde), and any combination thereof.

In one aspect, the disclosure provides a mutant Ras comprising at least one substituted amino acid. In some embodiments, (a) the substituted amino acid is a reactive amino acid that permits covalent conjugation between the mutant Ras and a competition probe exhibiting the ability to react with the reactive amino acid; and (b) the substituted amino acid is not a cysteine or an aspartic acid at position 12 or 13 relative to SEQ ID NO: 1 SEQ ID NO: 2 when optimally aligned. In some embodiments, the reactive amino acid is cysteine, lysine, tyrosine, aspartic acid, glutamic acid, or a non-natural amino acid. In some embodiments, the reactive amino acid is cysteine. In some embodiments, the competition probe is capable of binding the mutant Ras. In some embodiments, the competition probe competes for binding in the Switch II pocket of the mutant Ras. In some embodiments, the substituted amino acid is at a non-conserved position in Ras. In some embodiments, the substituted amino acid is at position 62, 92, or 95 relative to SEQ ID NO: 1 or SEQ ID NO: 2 when optimally aligned. In some embodiments, the substituted amino acid is a cysteine at position 62 relative to SEQ ID NO: 1 or SEQ ID NO: 2 when optimally aligned (e.g., E62C in KRAS, HRAS, or NRAS; E72C in MRAS; A100C in ERAS; E73C in RRAS2, RALA, or RALB; A80C in RIT1), a cysteine at position 92 relative to SEQ ID NO: 1 or SEQ ID NO: 2 when optimally aligned (e.g., D92C in KRAS, HRAS, or NRAS; H102C in MRAS; Q130C in ERAS; E103C in RRAS2; A103C in RALA or RALB; E110C in RIT1), or a cysteine at position 95 relative to SEQ ID NO: 1 or SEQ ID NO: 2 when optimally aligned (e.g., H95C in KRAS; Q95C in HRAS; L95C in NRAS; R105C in MRAS; Q133C in ERAS; K106C in RRAS2; D106C in RALA; E106C in RALB; E113C in RIT1). In some embodiments, the mutant Ras is selected from the group consisting of mutant KRAS, mutant HRAS, mutant NRAS, mutant MRAS, mutant ERAS, mutant RRAS2, mutant RALA, mutant RALB, mutant RIT1, and any combination thereof. In some embodiments, the mutant KRAS is a mutant KRAS isoform a or a mutant KRAS isoform b. In some embodiments, a mutant RRAS2 may be a mutant RRAS2 isoform a, a mutant RRAS2 isoform b, or a mutant RRAS2 isoform c. In some embodiments, a mutant RIT1 may be a mutant RIT1 isoform 1, a mutant RIT1 isoform 2, or a mutant RIT1 isoform 3. In some embodiments, the mutant Ras is selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, and any combination thereof. In some embodiments, the mutant Ras comprises one or more additional mutations, such as a mutation at a position selected from positions 12, 13, 14, 18, 19, 22, 59, 60, 61, 63, 117, 146, and any combination thereof relative to SEQ ID NO: 1 or SEQ ID NO: 2 when optimally aligned. In some embodiments, the one or more additional mutations comprises a mutation at a position selected from position 12, 13, 18, 61, 117, 146, and any combination thereof relative to SEQ ID NO: 1 or SEQ ID NO: 2 when optimally aligned. In some embodiments, the one or more additional mutations comprise a mutation at a position selected from positions 12 and 13 relative to SEQ ID NO: 1 or SEQ ID NO: 2 when optimally aligned. In some embodiments, the one or more additional mutations comprises a cysteine at position 12, an aspartic acid at position 12, a cysteine at position 13, an aspartic acid at position 13, or any combination thereof relative to SEQ ID NO: 1 or SEQ ID NO: 2 when optimally aligned.

In one aspect, the disclosure provides a mutant Ras comprising a substituted amino acid, wherein: (a) the substituted amino acid is a reactive amino acid that permits covalent conjugation between the mutant Ras and a competition probe exhibiting the ability to react with the reactive amino acid; (b) the substituted amino acid is a cysteine or an aspartic acid at position 12 or 13 relative to SEQ ID NO: 1 when optimally aligned; and (c) the mutant Ras is selected from the group consisting of mutant MRAS, mutant ERAS, mutant RRAS2, mutant RALA, mutant RALB, mutant RIT1, and any combination thereof. In some embodiments, the reactive amino acid is cysteine. In some embodiments, the competition probe is capable of binding the mutant Ras. In some embodiments, the competition probe competes for binding in the Switch II pocket of the mutant Ras. In some embodiments, the mutant Ras is selected from the group consisting of RALA, RALB, and any combination thereof. In some embodiments, the mutant Ras comprises one or more additional mutations. In some embodiments, the one or more additional mutations comprises a mutation at a position selected from position 12, 13, 14, 18, 19, 22, 59, 60, 61, 63, 117, 146, and any combination thereof relative to SEQ ID NO: 1 when optimally aligned, such as from position 12, 13, 18, 61, 117, 146, and any combination thereof relative to SEQ ID NO: 1 when optimally aligned.

In some embodiments, the mutant Ras is Kras, having mutations of G12D and D92C, or mutations of G12D and H95C.

In one aspect, the disclosure provides a polynucleotide encoding any mutant Ras described herein. In some embodiments, the polynucleotide comprises DNA or RNA.

In one aspect, the disclosure provides an expression vector comprising any of the polynucleotides described herein.

In one aspect, the disclosure provides a host cell comprising any of the polynucleotides described herein. In one aspect, the disclosure provides a host cell comprising any of the expression vectors described herein.

In one aspect, the disclosure provides a kit. In some embodiments, the kit comprises (a) a mutant Ras having a cysteine mutation at a position other than position 12 or 13 relative to SEQ ID NO: 1 or SEQ ID NO: 2 when optimally aligned; and (b) instructions for using the mutant Ras in a competition reaction between a competition probe and a test compound. In some embodiments, the kit further comprises the competition probe. In some embodiments, the kit further comprises one or more test compounds. In some embodiments, the mutant Ras is selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, and any combination thereof.

In one aspect, the disclosure provides a substrate having attached thereto a complex comprising a mutant Ras and a competition probe. In some embodiments, (a) the mutant Ras comprises a substituted amino acid that is a reactive amino acid that permits covalent conjugation between the mutant Ras and the competition probe; (b) the substituted amino acid is not a cysteine or an aspartic acid at position 12 or 13 relative to SEQ ID NO: 1 or SEQ ID NO: 2 when optimally aligned; and (c) the competition probe is covalently bound to the mutant Ras at the reactive amino acid. In some embodiments, the substrate is in a form selected from the group consisting of beads, microparticles, nanoparticles, nanocrystals, fibers, microfibers, nanofibers, nanowires, nanotubes, mats, planar sheets, planar wafers or slides, multi-well plates, optical slides, flow cells, channels, and any combination thereof. In some embodiments, the substrate comprises a material selected from the group consisting of glass, quartz, fused silica, silicon, metal, polymers, plastics, ceramics, composite materials, and any combination thereof.

In one aspect, the disclosure provides a system for selecting a Ras antagonist. In some embodiments, the system comprises: (a) a computer configured to receive a user request to perform a competition reaction; (b) a reaction module that prepares the competition reaction, the competition reaction comprising a mutant Ras, a competition probe that is capable of binding the mutant Ras, and a test compound; (c) a detection module that detects a decrease in binding between the mutant Ras and the competition probe as compared to binding of the mutant Ras in the absence of the test compound; and (d) a report generator that sends a report to a recipient, wherein the report contains results from the detection module; wherein (i) the mutant Ras comprises a cysteine mutation that is not at position 12 or 13 relative to SEQ ID NO: 1 or SEQ ID NO: 2 when optimally aligned; (ii) the competition probe is capable of covalently modifying the mutant Ras at the cysteine mutation; and (iii) the test compound inhibits covalent modification of the mutant Ras by the competition probe. In some embodiments, the report generator identifies the test compound as an inhibitor of Ras.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 shows that exemplary sites for substituted amino acid introduction (highlighted in black), including but not limited to position 62, position 95, and position 92, are not highly conserved in Ras family GTPases (SEQ ID NOS 50-57, respectively, in order of appearance). Positions are relative to SEQ ID NO: 1 when optimally aligned.

FIG. 4 shows that KRAS (SEQ ID NO: 58), HRAS (SEQ ID NO: 59), NRAS (SEQ ID NO: 60), RALA (SEQ ID NO: 61), and RALB (SEQ ID NO: 62) have high sequence conservation. Boxed positions indicate residues in the Switch II pocket. Position 12 in KRAS, HRAS, and NRAS is equivalent to position 23 in RALA and RALB.

FIG. 6 shows inhibition of competition probe depletion by D92C K-Ras in the presence of a test compound selected from CP-023 (1-(4-(6-chloro-2-(3-(dimethylamino)propoxy)-8-fluoro-7-(3-hydroxynaphthalen-1-yl)quinazolin-4-yl)piperazin-1-yl)ethanone), and CP-024 (4-(6-chloro-2-(3-(dimethylamino)propoxy)-8-fluoro-7-(3-hydroxynaphthalen-1-yl)quinazolin-4-yl)piperazine-1-carbaldehyde). K-Ras (2 CP-008 (100 nM), and test compound were incubated for 6 h. Depletion of CP-008 was determined by mass spectrometry against a nonreactive internal standard compound.

DETAILED DESCRIPTION OF THE INVENTION

Figure 1:
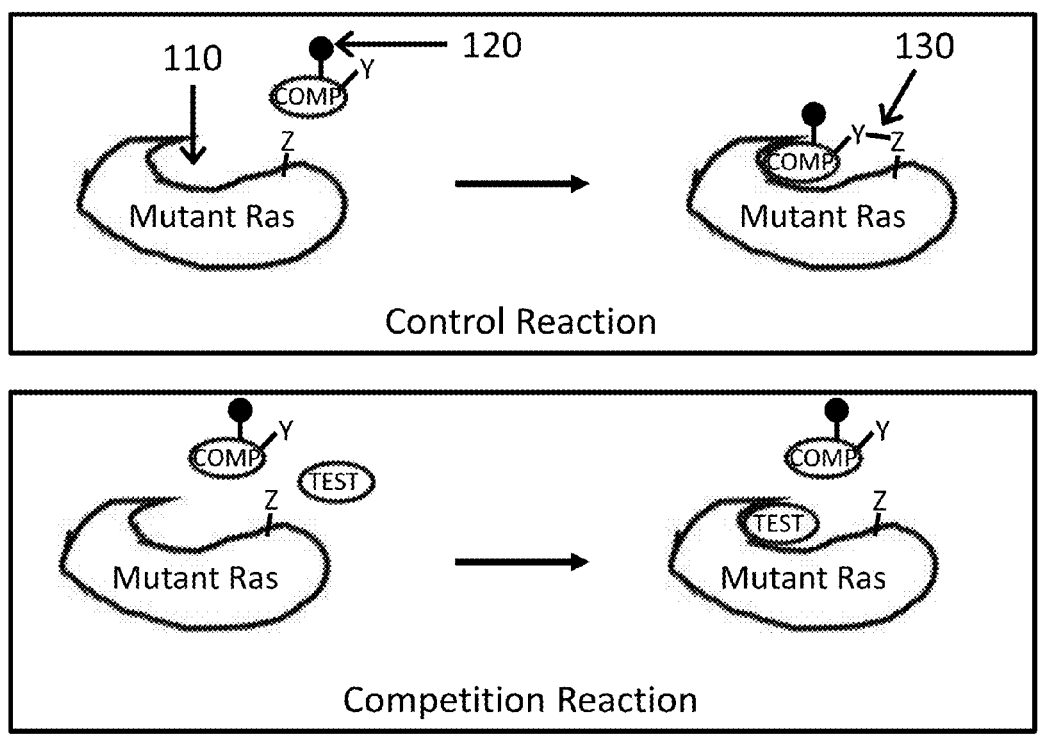
FIG. 1 illustrates an example of a competitive binding assay, in accordance with an embodiment. A mutant Ras comprises a substituted amino acid (Z) (e.g., E62C, D92C, H95C relative to SEQ ID NO: 1 when optimally aligned) and optionally one or more additional mutations (e.g., an oncogenic mutation such as G12X or Q61X relative to SEQ ID NO: 1 when optimally aligned). A competition probe (COMP) is capable of binding the mutant Ras, for example, in the Switch II pocket (110). The competition probe may contain a reactive moiety (Y) (e.g., an electrophilic group) and an optional affinity and/or detection tag (120). The competition probe may be capable of covalently modifying the mutant Ras, for example, by reacting through its reactive moiety with the substituted amino acid to form a covalent bond (130). A test compound (TEST) is a potential Switch II pocket binder. The extent of reaction (e.g., binding or covalent modification of the mutant Ras) in the competition reaction in the presence of a test compound is compared to the extent of reaction in the control reaction in the absence of a test compound.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 15%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

"Ras" refers to a protein in the Ras superfamily of small GTPases, such as in the Ras subfamily. The Ras superfamily includes, but is not limited to, the Ras subfamily, Rho subfamily, Rab subfamily, Rap subfamily, Arf subfamily, Ran subfamily, Rheb subfamily, RGK subfamily, Rit subfamily, Miro subfamily, and Unclassified subfamily. In some embodiments, a Ras protein is selected from the group consisting of KRAS, HRAS, NRAS, MRAS, ERAS, RRAS2, RALA, RALB, RIT1, and any combination thereof, such as from KRAS, HRAS, NRAS, RALA, RALB, and any combination thereof. Non-limiting examples of a Ras subfamily protein include DIRAS1; DIRAS2; DIRAS3; ERAS; GEM; HRAS; KRAS; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS; and RRAS2. Non-limiting examples of a Rho subfamily protein include RHOA; RHOB; RHOBTB1; RHOBTB2; RHOBTB3; RHOC; RHOD; RHOF; RHOG; RHOH; RHOJ; RHOQ; RHOU; RHOV; RND1; RND2; RND3; RAC1; RAC2; RAC3; and CDC42. Non-limiting examples of a Rab subfamily protein include RAB1A; RAB1B; RAB2; RAB3A; RAB3B; RAB3C; RAB3D; RAB4A; RAB4B; RAB5A; RAB5B; RAB5C; RAB6A; RAB6B; RAB6C; RAB7A; RAB7B; RAB7L1; RAB8A; RAB8B; RAB9; RAB9B; RABL2A; RABL2B; RABL4; RAB10; RAB11A; RAB11B; RAB12; RAB13; RAB14; RAB15; RAB17; RAB18; RAB19; RAB20; RAB21; RAB22A; RAB23; RAB24; RAB25; RAB26; RAB27A; RAB27B; RAB28; RAB2B; RAB30; RAB31; RAB32; RAB33A; RAB33B; RAB34; RAB35; RAB36; RAB37; RAB38; RAB39; RAB39B; RAB40A; RAB40AL; RAB40B; RAB40C; RAB41; RAB42; and RAB43. Non-limiting examples of a Rap subfamily protein include RAP1A; RAP1B; RAP2A; RAP2B; and RAP2C. Non-limiting examples of an Arf subfamily protein include ARF1; ARF3; ARF4; ARF5; ARF6; ARL1; ARL2; ARL3; ARL4; ARL5; ARL5C; ARL6; ARL7; ARL8; ARL9; ARL10A; ARL10B; ARL10C; ARL11; ARL13A; ARL13B; ARL14; ARL15; ARL16; ARL17; TRIM23, ARL4D; ARFRP1; and ARL13B. Non-limiting examples of a Ran subfamily protein include RAN. Non-limiting examples of a Rheb subfamily protein include RHEB and RHEBL1. Non-limiting examples of a RGK subfamily protein include RRAD; GEM; REM; and REM2. Non-limiting examples of a Rit subfamily protein include RIT1 and RIT2. Non-limiting examples of a Miro subfamily protein include RHOT1 and RHOT2. Non-limiting examples of an Unclassified subfamily protein include ARHGAP5; DNAJC27; GRLF1; and RASEF. Non-limiting examples of a RAL protein include RALA and RALB. In some embodiments, a Ras may be further modified, such as by conjugation with a detectable label. In some embodiments, a Ras is a full-length or truncated polypeptide. For example, a Ras may be a truncated polypeptide comprising residues 1-169 or residues 11-183 (e.g., residues 11-183 of RALA or RALB).

"Mutant Ras" and "Ras mutant" refer to a Ras protein with one or more amino acid mutations, such as with respect to a common reference sequence such as a wild-type (WT) sequence. In some embodiments, a mutant Ras is selected from a mutant KRAS, mutant HRAS, mutant NRAS, mutant MRAS, mutant ERAS, mutant RRAS2, mutant RALA, mutant RALB, mutant RIT1, and any combination thereof, such as from a mutant KRAS, mutant HRAS, mutant NRAS, mutant RALA, mutant RALB, and any combination thereof. In some embodiments, a mutation may be an introduced mutation, a naturally occurring mutation, or a non-naturally occurring mutation. In some embodiments, a mutation may be a substitution (e.g., a substituted amino acid), insertion (e.g., addition of one or more amino acids), or deletion (e.g., removal of one or more amino acids). In some embodiments, two or more mutations may be consecutive, non-consecutive, or a combination thereof. In some embodiments, a mutation may be present at any position of Ras. In some embodiments, a mutation may be present at position 12, 13, 62, 92, 95, or any combination thereof of Ras relative to SEQ ID NO: 1 when optimally aligned. In some embodiments, a mutant Ras may comprise about or at least about 1, 2, 3, 4, 5, 6, 7, 8, 9, 10, 11, 12, 13, 14, 15, 16, 17, 18, 19, 20, 25, 30, 35, 40, 45, 50, or more than 50 mutations. In some embodiments, a mutant Ras may comprise up to about 1, 2, 3, 4, 5, 6, 7, 8, 9, 10, 11, 12, 13, 14, 15, 16, 17, 18, 19, 20, 25, 30, 35, 40, 45, or 50 mutations. In some embodiments, the mutant Ras is about or up to about 500, 400, 300, 250, 240, 233, 230, 220, 219, 210, 208, 206, 204, 200, 195, 190, 189, 188, 187, 186, 185, 180, 175, 174, 173, 172, 171, 170, 169, 168, 167, 166, 165, 160, 155, 150, 125, 100, 90, 80, 70, 60, 50, or fewer than 50 amino acids in length. In some embodiments, an amino acid of a mutation is a proteinogenic, natural, standard, non-standard, non-canonical, essential, non-essential, or non-natural amino acid. In some embodiments, an amino acid of a mutation has a positively charged side chain, a negatively charged side chain, a polar uncharged side chain, a non-polar side chain, a hydrophobic side chain, a hydrophilic side chain, an aliphatic side chain, an aromatic side chain, a cyclic side chain, an acyclic side chain, a basic side chain, or an acidic side chain. In some embodiments, a mutation comprises a reactive moiety. In some embodiments, a substituted amino acid comprises a reactive moiety. In some embodiments, a mutant Ras may be further modified, such as by conjugation with a detectable label. In some embodiments, a mutant Ras is a full-length or truncated polypeptide. For example, a mutant Ras may be a truncated polypeptide comprising residues 1-169 or residues 11-183 (e.g., residues 11-183 of a mutant RALA or mutant RALB).

Figure 2:
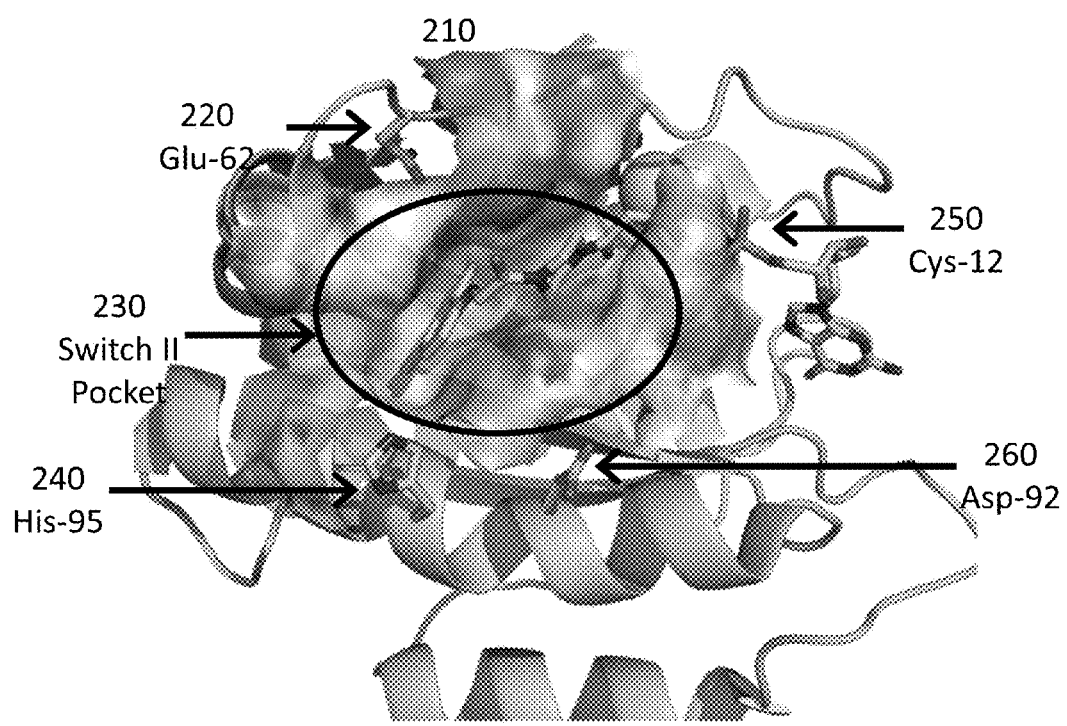
FIG. 2 shows that exemplary substituted amino acid sites, including but not limited to position 62 (220), position 95 (240), and position 92 (260), are near the Switch II pocket (230) of Ras (210). A mutant Ras may optionally comprise an additional mutation at position 12 (250). Positions are relative to SEQ ID NO: 1 when optimally aligned.
Figure 5:
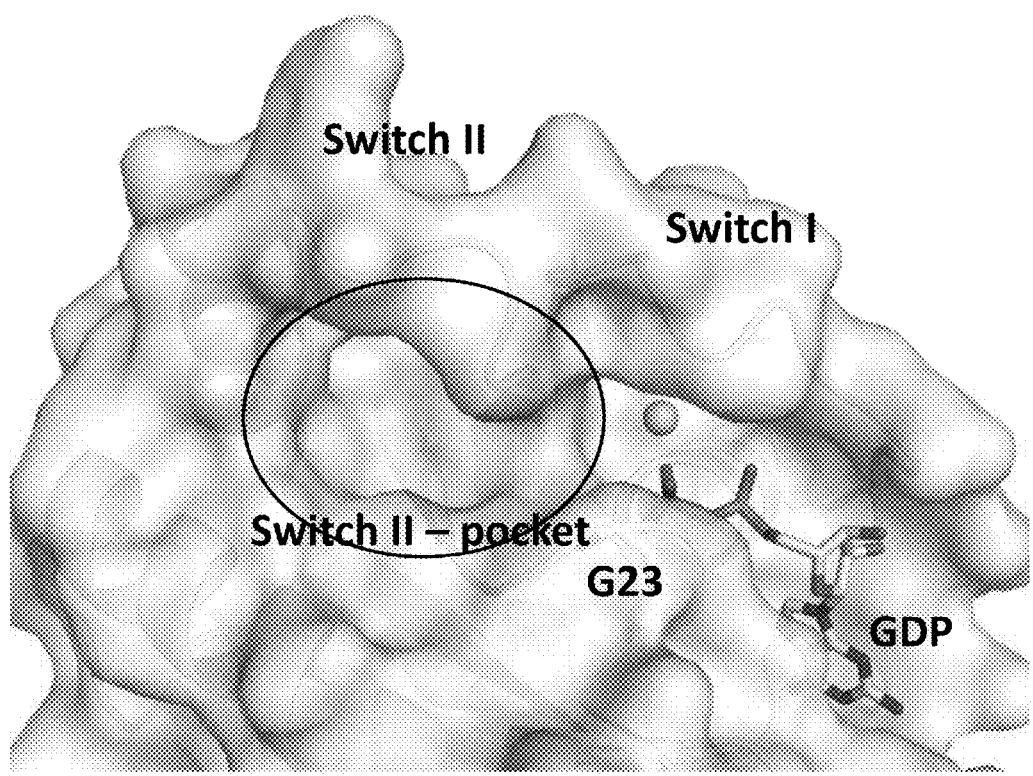
FIG. 5 shows that RAL proteins have a preformed Switch II pocket. Apo RalA GDP structure is shown. RCSB protein data bank structure 1U90.

"Switch II pocket" and "switch II binding pocket" refer to a binding pocket formed under the "Switch II" loop of Ras (see FIG. 2 and FIG. 5). In some embodiments, the Switch II pocket is located between the central β-sheet of Ras and the α2- and α3-helices. In some embodiments, the Switch II binding pocket is located about or at least about 5, 10, 20, 30, 40, 50, 60, 70, 80, 90, 100, 110, 120, 130, 140, 150, 160, 170, 180, 190, or 200 nm from position 12, position 60, position 99, or any combination thereof. In some embodiments, the Switch II binding pocket is located up to about 5, 10, 20, 30, 40, 50, 60, 70, 80, 90, 100, 110, 120, 130, 140, 150, 160, 170, 180, 190, or 200 nm from position 12, position 60, position 99, or any combination thereof.

"Competition probe" refers to compound capable of binding a mutant Ras. In some embodiments, a competition probe is capable of binding Ras. In some embodiments, a competition probe may be capable of covalently modifying a mutant Ras, for example, through a reactive moiety. In some embodiments, a competition probe may be capable of binding in the Switch II pocket of a mutant Ras. In some embodiments, a competition probe may be a Ras antagonist. In some embodiments, a competition probe comprises a reactive moiety (e.g., an electrophilic group, a nucleophilic group).

"Test compound" refers to a compound screened for the capability of binding a mutant Ras. In some embodiments, a test compound may be capable of binding Ras and/or a mutant Ras. In some embodiments, a test compound may be capable of binding in the Switch II pocket of Ras and/or a mutant Ras. In some embodiments, a test compound may be a Ras antagonist.

Figure 4:
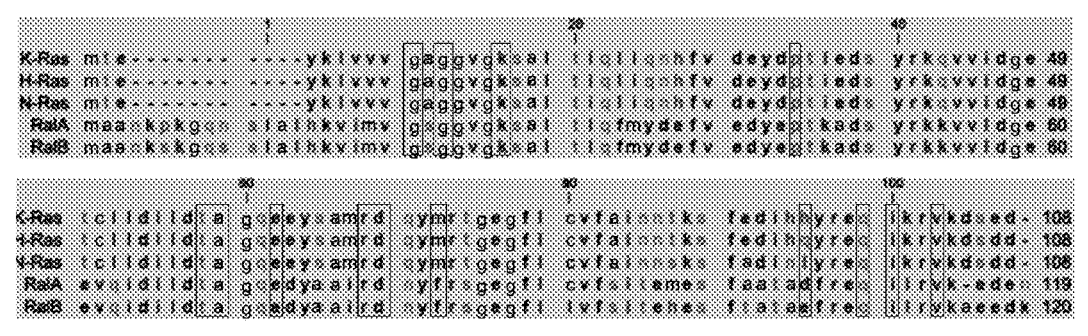

Amino acid positions, unless indicated otherwise, are relative to SEQ ID NO: 1 when optimally aligned. For example, FIG. 3 shows optimally aligned amino acid sequences for 51-amino acid segments of KRAS, HRAS, NRAS, MRAS, RRAS2, RALA, and RIT1 and a 48-amino acid segment of ERAS. For example, position 62 of KRAS, position 62 of HRAS, position 62 of NRAS, position 72 of MRAS, position 100 of ERAS, position 73 of RRAS2, position 73 of RALA, and position 80 of RIT1 correspond to position 62 of SEQ ID NO: 1 when optimally aligned. For example, FIG. 4 shows optimally aligned amino acid sequences for segments of KRAS, HRAS, NRAS, RALA, and RALB. For example, position 62 of KRAS, position 62 of HRAS, position 62 of NRAS, position 73 of RALA, and position 73 of RALB correspond to position 62 of SEQ ID NO: 1 when optimally aligned. For example, position 12 of KRAS, position 12 of HRAS, position 12 of NRAS, position 23 of RALA, and position 23 of RALB correspond to position 12 of SEQ ID NO: 1 when optimally aligned.

Amino acid mutations, unless indicated otherwise, are relative to SEQ ID NO: 1 when optimally aligned. For example, G12C of KRAS, G12C of HRAS, G12C of NRAS, G23C of RALA, and G23C of RALB correspond to G12C of SEQ ID NO: 1 when optimally aligned. For example, E62C of KRAS, E62C of HRAS, E62C of NRAS, E73C of RALA, and E73C of RALB correspond to E62C of SEQ ID NO: 1 when optimally aligned. For example, D92C of KRAS, D92C of HRAS, D92C of NRAS, A103C of RALA, and A103C of RALB correspond to D92C of SEQ ID NO: 1 when optimally aligned. For example, H95C of KRAS, Q95C of HRAS, L95C of NRAS, D106C of RALA, and E106C of RALB correspond to H95C of SEQ ID NO: 1 when optimally aligned.

"Reactive moiety" refers to any moiety that facilitates attachment by a chemical reaction (e.g., covalent bond formation) or a binding interaction. In some embodiments, a reactive moiety is a nucleophilic group such as a sulfur-containing group (e.g., thiol, thiolate, cysteine), nitrogen-containing group (e.g., amine, azide, alkoxyamine, hydrazine), carbon-containing group (e.g., enol, enolate, tyrosine, aniline, alkene, alkyne), phosphorus-containing group (e.g., phosphine compounds such as a triaryl phosphine), or oxygen-containing group (e.g., alcohol, alkoxide). In some embodiments, a reactive moiety is an electrophilic group such as an alkene, alkyne, aldehyde, ketone, N-hydroxysuccinimide ester, sulfo-N-hydroxysuccinimide ester, imidoester, sulfonyl chloride, carbodiimide, acyl azide, fluorobenzene, carbonate, fluorophenyl ester, maleimide, iodoacetamide, 2-thiopyridone, 3-carboxy-4-nitrothiophenol, epoxide, isothiocyanate, diazonium compound, isocyanate, anhydride, conjugated double bond, α,β-unsaturated carbonyl, acrylamide, vinyl sulfonamide, or α,β-unsaturated thiocarbonyl. In some embodiments, a reactive moiety is biotin, streptavidin, or avidin.

"Electrophile" and "electrophilic group" refer to any moiety capable of reacting with a nucleophile (e.g., a moiety having a lone pair of electrons, a negative charge, a partial negative charge and/or an excess of electrons, for example a —SH group). Electrophiles typically are electron poor or comprise atoms which are electron poor. In certain embodiments, an electrophile contains a positive charge or partial positive charge, has a resonance structure which contains a positive charge or partial positive charge, or is a moiety in which delocalization or polarization of electrons results in one or more atoms which contain a positive charge or partial positive charge. In some embodiments, the electrophile comprises conjugated double bonds, for example an α,β-unsaturated carbonyl, acrylamide, vinyl sulfonamide, or α,β-unsaturated thiocarbonyl compound. In some embodiments, the electrophile is capable of covalent and/or irreversible binding to a cysteine thiol group. In some embodiments, the electrophile is capable of forming a covalent bond with a mutant Ras protein, such as at position 62, 92, or 95 of a mutant Ras.

The terms "antagonist" and "inhibitor" are used interchangeably, and they refer to a compound having the ability to antagonize a biological function (e.g., activity, expression, binding, protein-protein interaction) of a target protein (e.g., Ras, mutant Ras, KRAS, HRAS, NRAS). Accordingly, the terms "antagonist" and "inhibitor" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" refers to a compound having the ability to initiate or enhance a biological function of a target protein, such as by triggering the activity or expression of the target protein. Accordingly, the term "agonist" is defined in the context of the biological role of the target polypeptide. While preferred agonists herein specifically interact with (e.g., bind to) the target, compounds that initiate or enhance a biological activity of the target polypeptide by interacting with other members of the signal transduction pathway of which the target polypeptide is a member are also specifically included within this definition.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

The terms "polynucleotide", "nucleotide", "nucleotide sequence", "nucleic acid", and "oligonucleotide" are used interchangeably. They refer to a polymeric form of nucleotides of any length, including deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), microRNA (miRNA), ribozymes, cDNA, recombinant polynucleotides, branched polynucleotides, plasmids, expression vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a detectable label.

"Expression" refers to the process by which a polynucleotide is transcribed from a DNA template (such as into mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide", and "protein" are used interchangeably herein to refer to polymers of amino acids of any length. The polymer may be linear or branched, may comprise modified amino acids, and may be interrupted by non amino acids. The terms also encompass an amino acid polymer that has been modified, for example, by disulfide bond formation, glycosylation, lipidation, acetylation, phosphorylation, or any other manipulation, such as conjugation with a detectable label.

As used herein the term "amino acid" includes natural and/or unnatural or synthetic amino acids, including glycine, cysteine, and both the D or L optical isomers, and amino acid analogs and peptidomimetics. In some embodiments, an amino acid is a proteinogenic, natural, standard, non-standard, non-canonical, essential, non-essential, or non-natural amino acid. In some embodiments, an amino acid has a positively charged side chain, a negatively charged side chain, a polar uncharged side chain, a non-polar side chain, a hydrophobic side chain, a hydrophilic side chain, an aliphatic side chain, an aromatic side chain, a cyclic side chain, an acyclic side chain, a basic side chain, or an acidic side chain. In some embodiments, an amino acid has a nucleophilic or electrophilic side chain.

The terms "conjugate" and "conjugated to" are intended to indicate the formation of a composite molecule by the covalent attachment of one or more proteins or small molecules to any of the articles of the invention described herein. "Covalent attachment" means that the two elements described are either directly covalently joined to each other (e.g., via a carbon-carbon bond), or are indirectly covalently joined to one another via an intervening chemical structure, such as a bridge, spacer, linker, linkage group, or any combination thereof. The term "bridge" refers to a molecular fragment that connects two distinct chemical elements (e.g., an inhibitor and a fluorophore). The terms "spacer" or "linker" are used interchangeably to refer to a single covalent bond or series of stable covalent bonds incorporating 1-30 nonhydrogen atoms selected from the group consisting of C, N, O, S, and P that covalently connect two or more distinct chemical elements. The term "linkage group" is intended to mean a chemical functional group capable of covalently joining two or more chemical elements (e.g., a phosphoryl or sulfonyl group).

"Control" refers to an alternative subject or sample used in an experiment for comparison purpose. A "control reaction" refers to a reaction, to which a competition reaction is compared. In some embodiments, a control reaction comprises the mutant Ras and competition probe but not the test compound of a competition reaction to which it is compared. In some embodiments, the control reaction may consist of the same contents by identity and quantity as the competition reaction but without the test compound.

The terms "determining", "measuring", "evaluating", "assessing", "assaying", and "analyzing" can be used interchangeably herein to refer to any form of measurement, and include determining if an element is present or not (for example, detection). These terms can include both quantitative and/or qualitative determinations. Assessing may be relative or absolute. "Detecting the presence of" can include determining the amount of something present and/or determining whether it is present or absent.

Sequence comparisons, such as for the purpose of assessing identities, mutations, or where one or more positions of a test sequence fall relative to one or more specified positions of a reference sequence (e.g., SEQ ID NO: 1), may be performed by any suitable alignment algorithm, including but not limited to the Needleman-Wunsch algorithm (see e.g., the EMBOSS Needle aligner available at www.ebi.ac.uk/Tools/psa/emboss_needle/, optionally with default settings), the BLAST algorithm (see e.g., the BLAST alignment tool available at blast.ncbi.nlm.nih.gov/Blast.cgi, optionally with default settings), and the Smith-Waterman algorithm (see e.g., the EMBOSS Water aligner available at www.ebi.ac.uk/Tools/psa/emboss_water/, optionally with default settings). Optimal alignment may be assessed using any suitable parameters of a chosen algorithm, including default parameters.

In general, "sequence identity" refers to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby, and comparing these sequences to a second nucleotide or amino acid sequence. Two or more sequences (polynucleotide or amino acid) can be compared by determining their "percent identity." The percent identity to a reference sequence (e.g., nucleic acid or amino acid sequences), which may be a sequence within a longer molecule (e.g., polynucleotide or polypeptide), may be calculated as the number of exact matches between two optimally aligned sequences divided by the length of the reference sequence and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul, et al., J. Mol. Biol. 215:403-410 (1990); Karlin And Altschul, Proc. Natl. Acad. Sci. USA 90:5873-5877 (1993); and Altschul et al., Nucleic Acids Res. 25:3389-3402 (1997). Briefly, the BLAST program defines identity as the number of identical aligned symbols (i.e., nucleotides or amino acids), divided by the total number of symbols in the shorter of the two sequences. The program may be used to determine percent identity over the entire length of the sequences being compared. Default parameters are provided to optimize searches with short query sequences, for example, with the blastp program. The program also allows use of an SEG filter to mask-off segments of the query sequences as determined by the SEG program of Wootton and Federhen, Computers and Chemistry 17:149-163 (1993). Ranges of desired degrees of sequence identity are approximately 80% to 100% and integer values there between. Typically, the percent identities between a disclosed sequence and a claimed sequence are at least 80%, at least 85%, at least 90%, at least 95%, or at least 98%. In general, an exact match indicates 100% identity over the length of the reference sequence.

The term "effective amount" or "therapeutically effective amount" refers to that amount of a compound described herein that is sufficient to affect the intended application, including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refers to an approach for obtaining beneficial or desired results with respect to a disease, disorder, or medical condition including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

"Pharmaceutically acceptable salt" includes both pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise desirable, and which are formed with inorganic acids such as, but are not limited to, hydrochloric acid, hydrobromic acid, sulfuric acid, nitric acid, phosphoric acid and the like, or organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise desirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

As used herein, "agent" or "biologically active agent" refers to a biological, pharmaceutical, or chemical compound. Non-limiting examples include a simple or complex organic or inorganic molecule, a peptide, a protein, an oligonucleotide, an antibody, an antibody derivative, antibody fragment, a vitamin derivative, a carbohydrate, a toxin, and a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs to a subject by various methods, including intravenous, oral, intramuscular, intraperitoneal, intravesical, subcutaneous, transdermal, buccal, or inhalation or in the form of a suppository.

The terms "subject" and "individual" are used interchangeably herein to refer to a vertebrate, preferably a mammal, more preferably a human. "Subject" refers to an animal, such as a mammal, for example a human. The methods described herein can be useful in both human therapeutics and veterinary applications. In some embodiments, the subject is a mammal, and in some embodiments, the subject is human.

"Mammal" includes humans and both domestic animals such as laboratory animals and household pets (e.g., cats, dogs, swine, cattle, sheep, goats, horses, rabbits), and non-domestic animals such as wildlife and the like. Mammals include, but are not limited to, murines, simians, humans, farm animals, sport animals, domesticated animals, and pets. Tissues, cells, and their progeny of a biological entity obtained in vivo or cultured in vitro are also encompassed.

The term "in vivo" refers to an event that takes place in a subject's body.

The term "in vitro" refers to an event that takes places outside of a subject's body. For example, an in vitro assay encompasses any assay run outside of a subject. In vitro assays encompass cell-based assays in which cells alive or dead are employed. In vitro assays also encompass a cell-free assay in which no intact cells are employed.

"Prodrug" is meant to indicate a compound that may be converted under physiological conditions or by solvolysis to a biologically active compound described herein (e.g., Ras antagonist). The term "prodrug" encompasses a precursor of a biologically active compound that is pharmaceutically acceptable. In some aspects, a prodrug is inactive when administered to a subject but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam); Higuchi, T., et al., "Pro-drugs as Novel Delivery Systems," (1987) A.C.S. Symposium Series, Vol. 14; and Bioreversible Carriers in Drug Design, ed. Edward B. Roche, American Pharmaceutical Association and Pergamon Press) each of which is incorporated in full by reference herein. The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

In certain embodiments, the proteins or compounds disclosed herein are isotopically labeled. Isotopically-labeled proteins or compounds (e.g., an isotopologue) may have one or more atoms replaced by an atom having a different atomic mass or mass number. Non-limiting examples of isotopes that can be incorporated into the disclosed compounds include isotopes of hydrogen, carbon, nitrogen, oxygen, phosphorous, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Certain isotopically-labeled compounds, for example, those incorporating a stable isotope, are useful in mass spectrometry studies. For instance, a stable isotopic protein may be used as a reference standard in a mass spectrometry based assay. Certain isotopically-labeled compounds, for example, those incorporating a radioactive isotope, are useful in drug and/or substrate tissue distribution studies. The radioactive isotopes tritium ($^{3}H$) and carbon-14 ($^{14}C$) are particularly useful for this purpose in view of their ease of incorporation and ready means of detection. These radiolabeled compounds could be useful to help determine or measure the effectiveness of the compounds, by characterizing, for example, the site or mode of action, or binding affinity to a pharmacologically important site of action. Substitution with heavier isotopes such as deuterium ($^{2}H$) may afford certain therapeutic advantages resulting from greater metabolic stability, for example, increased in vivo half-life or reduced dosage requirements, and hence are preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds can generally be prepared by conventional techniques known to those skilled in the art or by processes analogous to those described herein using an appropriate isotopically-labeled reagent in place of the non-labeled reagent.

"Optional" and "optionally" mean that the subsequently described event of circumstances may or may not occur, and that the description includes instances where the event or circumstance occurs and instances in which it does not. For example, "optionally substituted aryl" means that the aryl group may or may not be substituted and that the description includes both substituted aryl groups and aryl groups having no substitution.

"Pharmaceutically acceptable carrier, diluent or excipient" includes without limitation any adjuvant, carrier, excipient, glidant, sweetening agent, diluent, preservative, dye, colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The compounds of the various embodiments disclosed herein, or their pharmaceutically acceptable salts may contain one or more asymmetric centers and may thus give rise to enantiomers, diastereomers, and other stereoisomeric forms that are defined, in terms of absolute stereochemistry, as (R)- or (S)- or, as (D)- or (L)- for amino acids. The present disclosure is meant to include all such possible isomers, as well as their racemic and optically pure forms. A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are nonsuperimposeable mirror images of one another. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers.

A "tautomer" refers to a proton shift from one atom of a molecule to another atom of the same molecule. The present disclosure includes tautomers of any the compounds and all tautomeric forms are also intended to be included.

As used herein, the term "electrophile", "electrophilic group", or "electrophilic moiety" refers to any moiety capable of reacting with a nucleophile (e.g., a moiety having a lone pair of electrons, a negative charge, a partial negative charge and/or an excess of electrons, for example a —SH group). Electrophiles typically are electron poor or comprise atoms which are electron poor. In certain embodiments, an electrophile contains a positive charge or partial positive charge, has a resonance structure which contains a positive charge or partial positive charge, or is a moiety in which delocalization or polarization of electrons results in one or more atoms which contain a positive charge or partial positive charge. In some embodiments, the electrophile comprises conjugated double bonds, for example an α,β-unsaturated carbonyl or α,β-unsaturated thiocarbonyl compound. In some embodiments, the electrophile is capable of covalent and/or irreversible binding to cysteine sulfhydryl groups. In some embodiments, the electrophile is capable of forming an irreversible covalent bond with a Ras protein, such as with a cysteine of a Ras protein.

A "ligand" as used herein refers to a small molecule, small molecule fragment, or biological polymer (e.g., polypeptide, nucleic acid, carbohydrate) that can selectively bind to a receptor. The binding can be covalent or noncovalent. The term "selectively" refers to a binding interaction that is detectable over nonspecific interactions via a quantitative assay.

"Acyl" refers to the group —C(=O)$R_a$, where $R_a$ is selected from the group consisting of alkyl, cycloalkyl, aryl, heteroaryl (bonded through a ring carbon), heteroalkyl, and heterocyclylalkyl. Unless stated otherwise specifically in the specification, an acyl group is optionally substituted.

"Alkyl" refers to a straight or branched hydrocarbon chain moiety consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Alkyl includes alkenyls (one or more carbon-carbon double bonds) and alkynyls (one or more carbon-carbon triple bonds). Unless stated otherwise specifically in the specification, an alkyl group is optionally substituted.

"Alkoxy" refers to a moiety of the formula —O$R_a$ where $R_a$ is an alkyl group as defined herein containing one to twelve carbon atoms. Unless stated otherwise specifically in the specification, an alkoxy group is optionally substituted.

"Alkylamino" refers to a moiety of the formula —NH$R_a$ or —N$R_a R_b$ where $R_a$ and $R_b$ are each independently an alkyl group as defined herein containing one to twelve carbon atoms. Unless stated otherwise specifically in the specification, an alkylamino group is optionally substituted.

"Aminoalkyl" refers to an alkyl moiety comprising at least one amino substituent. The amino substituent can be on a tertiary, secondary or primary carbon. Unless stated otherwise specifically in the specification, an aminoalkyl group is optionally substituted.

"Aryl" refers to a hydrocarbon ring system moiety comprising 6 to 18 carbon atoms and at least one aromatic ring. For purposes of this invention, the aryl moiety is a monocyclic, bicyclic, tricyclic, or tetracyclic ring system, which may include fused or bridged ring systems. Aryl moieties include, but are not limited to, aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl groups that are optionally substituted.

"Heterocycle" refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, and 6- to 12-membered bridged rings. Each ring of a bicyclic heterocycle may be selected from saturated, unsaturated, and aromatic rings. The heterocycle may be attached to the rest of the molecule through any atom of the heterocycle, valence permitting, such as a carbon or nitrogen atom of the heterocycle. In some embodiments, the heterocycle is a heteroaryl. In some embodiments, the heterocycle is a heterocycloalkyl. In an exemplary embodiment, a heterocycle, e.g., pyridyl, may be fused to a saturated or unsaturated ring, e.g., cyclohexane, cyclopentane, or cyclohexene. Exemplary heterocycles include pyrrolidinyl, pyrrolyl, imidazolyl, pyrazolyl, triazolyl, piperidinyl, pyridinyl, pyrimidinyl, pyridazinyl, pyrazinyl, thiophenyl, oxazolyl, thiazolyl, morpholinyl, indazolyl, indolyl, and quinolinyl. Unless stated otherwise specifically in the specification, a heterocycle is optionally substituted by one or more substituents such as those substituents described herein.

"Heteroaryl" refers to a 3- to 12-membered aromatic ring that comprises at least one heteroatom wherein each heteroatom may be independently selected from N, O, and S. As used herein, the heteroaryl ring may be selected from monocyclic or bicyclic and fused or bridged ring systems wherein at least one of the rings in the ring system is aromatic, i.e., it contains a cyclic, delocalized (4n+2) π-electron system in accordance with the Hückel theory. The heteroatom(s) in the heteroaryl may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, a heteroaryl is optionally substituted by one or more substituents such as those substituents described herein.

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen (e.g., F, Cl, Br, or I), a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, a carbocycle, a heterocycle, a cycloalkyl, a heterocycloalkyl, an aromatic and heteroaromatic moiety. In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2), and —R$^b$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, hydroxy, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); wherein each R$^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each R$^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^c$ is a straight or branched alkylene, alkenylene or alkynylene chain.

It will be understood by those skilled in the art that substituents can themselves be substituted, if appropriate. Unless specifically stated as "unsubstituted," references to chemical moieties herein are understood to include substituted variants. For example, reference to a "heteroaryl" group or moiety implicitly includes both substituted and unsubstituted variants.

A "competition binding assay" is a robust and high-throughput compatible assay strategy for screening against a specific binding site. Typically, competition binding assays use a high affinity reversible ligand and employ fluorescence (e.g., fluorescence polarization, FRET), immunochemical (e.g., ELISA), or other detection methods (e.g., SPR, bead based methods) to determine the extent of ligand binding in the presence of competing molecules from a screening library. Such methods generally employ a high affinity ligand for the target and target site of interest. For Ras proteins, high affinity reversible ligands exist for the GTP pocket, but this target site is widely considered to be undruggable due to high GTP affinity coupled with high intracellular GTP levels.

For Ras proteins, the Switch II pocket represents an attractive target site for inhibitor screening. Recently, covalent ligands have been increasingly used for competition binding assays, and this approach has been successfully used in multiple high-throughput screens (Lone, A. M. et al. *J. Am. Chem. Soc.* 2011, 133, 11665-74, which is entirely incorporated herein by reference; Dillon, M. B.; Bachovchin, D. A.; Brown, S. J.; Finn, M. G.; Rosen, H.; Cravatt, B. F.; Mowen, K. A. *ACS Chem. Biol.* 2012, 7, 1198-204, which is entirely incorporated herein by reference; Bachovchin, D. A.; Brown, S. J.; Rosen, H.; Cravatt, B. F. *Nat. Biotechnol.* 2009, 27, 387-94, which is entirely incorporated herein by reference; Adibekian, A. et al. *Probe Reports from the NIH Molecular Libraries Program* 2010, which is entirely incorporated herein by reference). In principle, covalent KRAS-G12C targeting compounds such as those described by Ostrem et al. (Ostrem, J. M.; Peters, U.; Sos, M. L.; Wells, J. A.; Shokat, K. M. *Nature* 2013, 503, 548-551, which is entirely incorporated herein by reference) may be used for competition binding assays. Alternative 12-position mutants, such as G12V, G12D, and G12S, are common in human cancers, and a preferred Ras screening strategy would allow for screening of multiple or all prominent Ras mutants. Ras antagonists binding in the Switch II pocket may extend near the site of the 12-position and interact with the 12-position residue, providing some degree of mutant binding selectivity. Since mutant selective inhibitors would be a desired outcome of a screen, the ability to specifically screen the mutant of interest is likewise desirable. Flexibility in the screened target (e.g., the specific Ras mutant to be screened) is a feature of a preferred Ras screening assay.

In one aspect, the present disclosure provides a method of selecting a Ras antagonist. An illustration of an exemplary embodiment is provided in FIG. 1. In some embodiments, the method comprises combining in a competition reaction a mutant Ras, a competition probe, and a test compound. In some embodiments, the method comprises detecting a decrease in binding between the mutant Ras and the competition probe as compared to binding of the mutant Ras in the absence of the test compound.

In some embodiments, the competition probe comprises a reactive moiety, such as a nucleophilic group or an electrophilic group such as any electrophilic group capable of covalent and/or irreversible binding to a cysteine thiol group. In some embodiments, the competition probe is a compound of formula

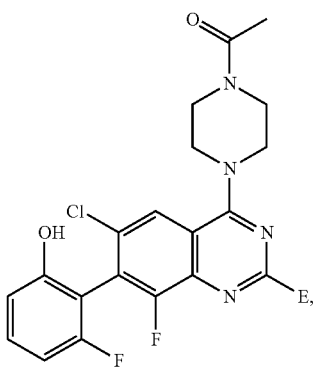

or a pharmaceutically acceptable salt thereof, wherein E comprises a reactive moiety, such as a nucleophilic group or an electrophilic group such as any electrophilic group capable of covalent and/or irreversible binding to a cysteine thiol group. Additional examples of competition probes are provided in Table 2 and Table 3. One or more competition probes may be used in a single reaction. For example, a competition reaction may comprise 1, 2, 3, 4, 5, or more competition probes. In some embodiments, the competition probe is selected from the group consisting of CP-001, CP-002, CP-003, CP-004, CP-005, CP-006, CP-007, CP-008, CP-009, CP-010, CP-011, CP-012, CP-013, CP-014, CP-015, CP-016, CP-017, CP-018, CP-019, CP-020, and any combination thereof.

In some embodiments, the competition probe binds to Ras with a $K_d$ of about or at least about 100 pM, 200 pM, 300 pM, 400 pM, 500 pM, 600 pM, 700 pM, 800 pM, 900 pM, 1 nM, 2 nM, 3 nM, 4 nM, 5 nM, 6 nM, 7 nM, 8 nM, 9 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 1 μM, 2 μM, 3 μM, 4 μM, 5 μM, 6 μM, 7 μM, 8 μM, 9 μM, 10 μM, 15 μM, 20 μM, 25 μM, 30 μM, 35 μM, 40 μM, 45 μM, 50 μM, 55 μM, 60 μM, 65 μM, 70 μM, 75 μM, 80 μM, 85 μM, 90 μM, 95 μM, 100 μM, 150 μM, 200 μM, 250 μM, 300 μM, 350 μM, 400 μM, 450 μM, 500 μM, or more than 500 μM. In some embodiments, the competition probe binds to Ras with a $K_d$ of up to about 100 pM, 200 pM, 300 pM, 400 pM, 500 pM, 600 pM, 700 pM, 800 pM, 900 pM, 1 nM, 2 nM, 3 nM, 4 nM, 5 nM, 6 nM, 7 nM, 8 nM, 9 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 1 μM, 2 μM, 3 μM, 4 μM, 5 μM, 6 μM, 7 μM, 8 μM, 9 μM, 10 μM, 15 μM, 20 μM, 25 μM, 30 μM, 35 μM, 40 μM, 45 μM, 50 μM, 55 μM, 60 μM, 65 μM, 70 μM, 75 μM, 80 μM, 85 μM, 90 μM, 95 μM, 100 μM, 150 μM, 200 μM, 250 μM, 300 μM, 350 μM, 400 μM, 450 μM, or 500 μM. In some embodiments, the competition probe binds Ras with a Kd of between 100 pM to 50 nm, or 500 pM to 1 nM.

In some embodiments, the competition probe covalently modifies a mutant Ras. Covalent modification can be expressed as a percentage of modified protein. The percentage of protein modified may be calibrated based on reaction conditions, such as the competition probe selected, the Ras mutant under study, the concentration of the competition probe, and the duration of the reaction. In some embodiments, the competition probe covalently modifies a percentage of mutant Ras proteins in a competition reaction, control reaction, or reaction mixture. In some embodiments, the competition probe covalently modifies about or at least about 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% of mutant Ras proteins in a competition reaction, control reaction, or reaction mixture. In some embodiments, the competition probe covalently modifies up to about 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% of mutant Ras proteins in a competition reaction, control reaction, or reaction mixture. A control reaction, such as a reaction comprising a competition probe and a mutant Ras in the absence of one or more test compounds, can form a baseline for comparing the effects of competition with one or more test compounds. In some embodiments, a competition probe is provided at a concentration of at least about 5 (e.g., 10 μM, 30 μM, 100 μM, or more), and achieves at least about 80% modification (e.g., 85%, 90%, 95%, or higher) in about or fewer than about 10 hours (e.g., 8, 7, 6, 5, 4, 3, 2, or fewer hours) in the absence of a test compound. In some embodiments, covalent modification in the presence of a test compound is expressed as a percentage relative to the degree of modification obtained in a control reaction lacking the test compound. For example, the presence of a test compound may reduce covalent modification of a mutant Ras by about or at least about 10%, 25%, 50%, 75%, 90%, or more relative to the control reaction.

In some embodiments, a test compound is selected from the group consisting of CP-023 (1-(4-(6-chloro-2-(3-(dimethylamino)propoxy)-8-fluoro-7-(3-hydroxynaphthalen-1-yl)quinazolin-4-yl)piperazin-1-yl)ethanone), CP-024 (4-(6-chloro-2-(3-(dimethylamino)propoxy)-8-fluoro-7-(3-hydroxynaphthalen-1-yl)quinazolin-4-yl)piperazine-1-carbaldehyde), and any combination thereof.

Ras mutants useful in the methods and compositions of the disclosure can comprise one or more mutations, such as any of the mutant Ras proteins described herein. Mutations may be naturally occurring mutations, or mutations that are artificially generated, such as by non-specific or targeted mutagenesis procedures. Examples of mutations that can be introduced include, but are not limited to, insertions, deletions, substitutions, and rearrangements. In some embodiments, the mutation is a substitution, such as in the substitution of an amino acid. The positions for substituted amino acid introduction may be chosen to be near enough to the Switch II pocket to allow for reaction with a Switch II binding competition probe, but outside of the pocket so as not to alter the binding properties of Switch II pocket binders (see e.g., FIG. 2). In addition, positions may be selected that show some degree of variation across small GTPase sequence space, as shown in FIG. 3 and FIG. 4. In contrast, many positions in the core small GTPase fold are invariant across the entire family. For example, a cysteine mutation may be a mutation relative to position 62, 92, or 95 of SEQ ID NO: 1 when optimally aligned.

Among the mutations useful in some embodiments of the present disclosure are cysteine mutations. In some embodiments, the cysteine mutation is not at position 12 or 13 relative to SEQ ID NO: 1 or SEQ ID NO: 2 when optimally aligned. In some embodiments, the cysteine mutation is at position 12 or 13 relative to SEQ ID NO: 1 or SEQ ID NO: 2 when optimally aligned. In some embodiments, the cysteine mutation is at position 12 or 13 relative to SEQ ID NO: 1 when optimally aligned, and the mutant Ras is selected from mutant MRAS, mutant ERAS, mutant RRAS2, mutant RALA, mutant RALB, mutant RIT1, and any combination thereof. In some embodiments, the cysteine mutation is at a non-conserved amino acid position. In general, a "conserved amino acid" refers to an amino acid that is either identical or functionally or structurally equivalent at analogous positions across homologous species or members of a protein family. Where an identical amino acid or functionally or structurally equivalent amino acid is found in at least 2, 3, 4, 5, or more members of a family, such amino acid can be considered as highly conserved. Examples of conserved amino acids are provided herein, and others are recognized in the art.

In some embodiments, the competition probe covalently modifies the mutant Ras by reacting with the cysteine residue of the cysteine mutation. Modification may be selective, such as by selectively binding the mutant Ras (e.g., in proximity to a cysteine residue to be modified). In some embodiments, the cysteine mutation is a mutation relative to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, or SEQ ID NO: 48 when optimally aligned. In some embodiments, the cysteine mutation is at position 62, 92, 95, or any combination thereof relative to SEQ ID NO: 1 or SEQ ID NO: 2 when optimally aligned. In some embodiments, the mutant Ras comprises one or more additional mutations. In some embodiments, the mutant Ras comprises 0, 1, 2, 3, 4, 5, 6, 7, 8, 9, 10, 11, 12, 13, 14, 15, 16, 17, 18, 19, 20, or more additional mutations. The additional mutations may comprise one or more cysteine mutations. In some embodiments, the additional mutations do not comprise cysteine mutations. Non-limiting examples of additional mutations include substitutions, deletions, and insertions. In some embodiments, a mutant Ras comprises a mutation at one or more of positions 12, 13, 14, 18, 19, 22, 59, 60, 61, 63, 117, and 146 relative to SEQ ID NO: 1 or SEQ ID NO: 2 when optimally aligned. In some embodiments, the mutant Ras comprises a mutation at one or more of positions 12, 13, 18, 61, 117, and 146 relative to SEQ ID NO: 1 or SEQ ID NO: 2 when optimally aligned. A mutant Ras may comprise a mutation at one or both of positions 12 and 13 relative to SEQ ID NO: 1 or SEQ ID NO: 2 when optimally aligned (e.g., an aspartic acid at position 12 and/or 13 relative to SEQ ID NO: 1 or SEQ ID NO: 2 when optimally aligned). In some embodiments, the subject method and/or reaction mixture utilizes a KRAS double mutant based on SEQ ID NO: 1, in which positions 12 and 92 are substituted as G12D and D92C. In some embodiments, the subject method utilizes a KRAS double mutant based on SEQ ID NO: 1, in which positions 12 and 95 are substituted as G12D and H95C. In some embodiments, the subject method utilizes a KRAS mutant having a sequence shown in SEQ ID NO: 17, SEQ ID NO: 19, SEQ ID NO: 21, SEQ ID NO: 36, SEQ ID NO: 37, or SEQ ID NO: 38. In some embodiments, the subject method utilizes a KRAS double mutant based on SEQ ID NO: 2, in which positions 12 and 92 are substituted as G12D and D92C. In some embodiments, the subject method utilizes a KRAS double mutant based on SEQ ID NO: 2, in which positions 12 and 95 are substituted as G12D and H95C. In some embodiments, the subject method utilizes a KRAS mutant having a sequence shown in SEQ ID NO: 30, SEQ ID NO: 31, SEQ ID NO: 32, SEQ ID NO: 42, SEQ ID NO: 43 or SEQ ID NO: 44.

Exemplary Ras and mutant Ras sequences are provided in Table 1.

TABLE 1

| SEQ ID NO: 1 | WT KRAS isoform a | MTEYKLVVVGAGGVGKSALTIQLIQNHFVD EYDPTIEDSYRKQVVIDGETCLLDILDTAG QEEYSAMRDQYMRTGEGFLCVFAINNTKSF EDIHHYREQIKRVKDSEDVPMVLVGNKCDL PSRTVDTKQAQDLARSYGIPFIETSAKTRQ RVEDAFYTLVREIRQYRLKKISKEEKTPGC VKIKKCIIM |

TABLE 1-continued

| SEQ ID NO: | Name | Sequence |
|---|---|---|
| SEQ ID NO: 2 | WT KRAS isoform b | MTEYKLVVVGAGGVGKSALTIQLIQNHFVD EYDPTIEDSYRKQVVIDGETCLLDILDTAG QEEYSAMRDQYMRTGEGFLCVFAINNTKSF EDIHHYREQIKRVKDSEDVPMVLVGNKCDL PSRTVDTKQAQDLARSYGIPFIETSAKTRQ GVDDAFYTLVREIRKHKEKMSKDGKKKKKK SKTKCVIM |
| SEQ ID NO: 3 | WT HRAS | MTEYKLVVVGAGGVGKSALTIQLIQNHFVD EYDPTIEDSYRKQVVIDGETCLLDILDTAG QEEYSAMRDQYMRTGEGFLCVFAINNTKSF EDIHQYREQIKRVKDSDDVPMVLVGNKCDL AARTVESRQAQDLARSYGIPYIETSAKTRQ GVEDAFYTLVREIRQHKLRKLNPPDESGPG CMSCKCVLS |
| SEQ ID NO: 4 | WT NRAS | MTEYKLVVVGAGGVGKSALTIQLIQNHFVD EYDPTIEDSYRKQVVIDGETCLLDILDTAG QEEYSAMRDQYMRTGEGFLCVFAINNSKSF ADINLYREQIKRVKDSDDVPMVLVGNKCDL PTRTVDTKQABELAKSYGIPFIETSAKTRQ GVEDAFYTLVREIRQYRMKKLNSSDDGTQG CMGLPCVVM |
| SEQ ID NO: 5 | WT MRAS | MATSAVPSDNLPTYKLVVVGDGGVGKSALT IQFFQKIFVPDYDPTIEDSYLKHTEIDNQW AILDVLDTAGQEEFSAMREQYMRTGDGFLI VYSVTDKASFEHVDRFHQLILRVKDRESFP MILVANKVDLMEILRKITREQGKEMATKHN IPYIETSAKDPPLNVDKAFHDLVRVIRQQI PEKSQKKKKKTKWRGDRATGTHKLQCVIL |
| SEQ ID NO: 6 | WT ERAS | MELPTKPGTFDLGLATWSPSFQGETHRAQA RRRDVGRQLPEYKAVVVGASGVGKSALTIQ LNHQCFVEDHDPTIQDSYWKELTLDSGDCI LNVLDTAGQAIHRALRDQCLAVCDGVLGVF ALDDPSSLIQLQQIWATWGPHPAQPLVLVG NKCDLVTTAGDAHAAAAALAHSWGAHFVET SAKTRQGVEEAFSLLVHEIQRVQEAMAKEP MARSCREKRTRHQKATCHCGCSVA |
| SEQ ID NO: 7 | WT RRAS2 isoform a | MAAAGWRDGSGQEKYRLVVVGGGGVGKSAL TIQFIQSYFVTDYDPTIEDSYTKQCVIDDR AARLDILDTAGQEEFGAMREQYMRTGEGFL LVFSVTDRGSFEEIYKFQRQILRVKDRDEF PMILIGNKADLDHQRQVTQEEGQQLARQLK VTYMEASAKIRMNVDQAFHELVRVIRKFQE QECPPSPEPTRKEKDKKGCHCVIF |
| SEQ ID NO: 8 | WT RALA | MAANKPKGQNSLALHKVIMVGSGGVGKSAL TLQFMYDEFVEDYEPTKADSYRKKVVLDGE EVQIDILDTAGQEDYAAIRDNYFRSGEGFL CVFSITEMESFAATADFREQILRVKEDENV PFLLVGNKSDLEDKRQVSVEEAKNRAEQWN VNYVETSAKTRANVDKVFFDLMREIRARKM EDSKEKNGKKKRKSLAKRIRERCCIL |
| SEQ ID NO: 9 | WT RALB | MAANKSKGQSSLALHKVIMVGSGGVGKSAL TLQFMYDEFVEDYEPTKADSYRKKVVLDGE EVQIDILDTAGQEDYAAIRDNYFRSGEGFL LVFSITEHESFTATAEFREQILRVKAEEDK IPLLVVGNKSDLEERRQVPVEEARSKAEEW GVQYVETSAKTRANVDKVFFDLMREIRTKK MSENKDKNGKKSSKNKKSFKERCCLL |
| SEQ ID NO: 10 | WT RIT1 isoform 2 | MDSGTRPVGSCCSSPAGLSREYKLVMLGAG GVGKSAMTMQFISHRFPEDHDPTIEDAYKI RIRIDDEPANLDILDTAGQAEFTAMRDQYM RAGEGFIICYSITDRRSFHEVREFKQLIYR VRRTDDTPVVLVGNKSDLKQLRQVTKEEGL ALAREFSCPFFETSAAYRYYIDDVFHALVR EIRRKEKEAVLAMEKKSKPKNSVWKRLKSP FRKKKDSVT |
| SEQ ID NO: 11 | KRAS isoform a E62C | MTEYKLVVVGAGGVGKSALTIQLIQNHFVD EYDPTIEDSYRKQVVIDGETCLLDILDTAG QCEYSAMRDQYMRTGEGFLCVFAINNTKSF EDIHHYREQIKRVKDSEDVPMVLVGNKCDL PSRTVDTKQAQDLARSYGIPFIETSAKTRQ RVEDAFYTLVREIRQYRLKKISKEEKTPGC VKIKKCIIM |
| SEQ ID NO: 12 | KRAS E62C | MTEYKLVVVGAGGVGKSALTIQLIQNHFVD EYDPTIEDSYRKQVVIDGETCLLDILDTAG QCEYSAMRDQYMRTGEGFLCVFAINNTKSF EDIHHYREQIKRVKDSEDVPMVLVGNKCDL PSRTVDTKQAQDLARSYGIPFIETSAKTRQ RVEDAFYTLVREIRKHKEKMSKDGKKKKKK SKTKCVIM |
| SEQ ID NO: 13 | KRAS isoform a D92C | MTEYKLVVVGAGGVGKSALTIQLIQNHFVD EYDPTIEDSYRKQVVIDGETCLLDILDTAG QEEYSAMRDQYMRTGEGFLCVFAINNTKSF ECIHHYREQIKRVKDSEDVPMVLVGNKCDL PSRTVDTKQAQDLARSYGIPFIETSAKTRQ RVEDAFYTLVREIRQYRLKKISKEEKTPGC VKIKKCIIM |
| SEQ ID NO: 14 | KRAS D92C | MTEYKLVVVGAGGVGKSALTIQLIQNHFVD EYDPTIEDSYRKQVVIDGETCLLDILDTAG QEEYSAMRDQYMRTGEGFLCVFAINNTKSF ECIHHYREQIKRVKDSEDVPMVLVGNKCDL PSRTVDTKQAQDLARSYGIPFIETSAKTRQ RVEDAFYTLVREIRKHKEKMSKDGKKKKKK SKTKCVIM |
| SEQ ID NO: 15 | KRAS isoform a H95C | MTEYKLVVVGAGGVGKSALTIQLIQNHFVD EYDPTIEDSYRKQVVIDGETCLLDILDTAG QEEYSAMRDQYMRTGEGFLCVFAINNTKSF EDIHCYREQIKRVKDSEDVPMVLVGNKCDL PSRTVDTKQAQDLARSYGIPFIETSAKTRQ RVEDAFYTLVREIRQYRLKKISKEEKTPGC VKIKKCIIM |
| SEQ ID NO: 16 | KRAS H95C | MTEYKLVVVGAGGVGKSALTIQLIQNHFVD EYDPTIEDSYRKQVVIDGETCLLDILDTAG QEEYSAMRDQYMRTGEGFLCVFAINNTKSF EDIHCYREQIKRVKDSEDVPMVLVGNKCDL PSRTVDTKQAQDLARSYGIPFIETSAKTRQ RVEDAFYTLVREIRKHKEKMSKDGKKKKKK SKTKCVIM |
| SEQ ID NO: 17 | KRAS isoform a G12D E62C | MTEYKLVVVGADGVGKSALTIQLIQNHFVD EYDPTIEDSYRKQVVIDGETCLLDILDTAG QCEYSAMRDQYMRTGEGFLCVFAINNTKSF EDIHHYREQIKRVKDSEDVPMVLVGNKCDL PSRTVDTKQAQDLARSYGIPFIETSAKTRQ RVEDAFYTLVREIRQYRLKKISKEEKTPGC VKIKKCIIM |
| SEQ ID NO: 18 | KRAS G12D E62C | MTEYKLVVVGADGVGKSALTIQLIQNHFVD EYDPTIEDSYRKQVVIDGETCLLDILDTAG QCEYSAMRDQYmRTGEGFLCVFAINNTKSF EDIHHYREQIKRVKDSEDVPMVLVGNKCDL PSRTVDTKQAQDLARSYGIPFIETSAKTRQ RVEDAFYTLVREIRKHKEKMSKDGKKKKKK SKTKCVIM |
| SEQ ID NO: 19 | KRAS isoform a G12D D92C | MTEYKLVVVGADGVGKSALTIQLIQNHFVD EYDPTIEDSYRKQVVIDGETCLLDILDTAG QEEYSAMRDQYMRTGEGFLCVFAINNTKSF ECIHHYREQIKRVKDSEDVPMVLVGNKCDL PSRTVDTKQAQDLARSYGIPFIETSAKTRQ RVEDAFYTLVREIRQYRLKKISKEEKTPGC VKIKKCIIM |
| SEQ ID NO: 20 | KRAS G12D D92C | MTEYKLVVVGADGVGKSALTIQLIQNHFVD EYDPTIEDSYRKQVVIDGETCLLDILDTAG QEEYSAMRDQYMRTGEGFLCVFAINNTKSF ECIHHYREQIKRVKDSEDVPMVLVGNKCDL PSRTVDTKQAQDLARSYGIPFIETSAKTRQ RVEDAFYTLVREIRKHKEKMSKDGKKKKKK SKTKCVIM |
| SEQ ID NO: 21 | KRAS isoform a G12D H95C | MTEYKLVVVGADGVGKSALTIQLIQNHFVD EYDPTIEDSYRKQVVIDGETCLLDILDTAG QEEYSAMRDQYMRTGEGFLCVFAINNTKSF EDIHCYREQIKRVKDSEDVPMVLVGNKCDL PSRTVDTKQAQDLARSYGIPFIETSAKTRQ |

TABLE 1-continued

| SEQ ID NO: | Name | Sequence |
|---|---|---|
| | | RVEDAFYTLVREIRQYRLKKISKEEKTPGCVKIKKCIIM |
| SEQ ID NO: 22 | KRAS G12D H95C | MTEYKLVVVGADGVGKSALTIQLIQNHFVDEYDPTIEDSYRKQVVIDGETCLLDILDTAGQEEYSAMRDQYMRTGEGFLCVFAINNTKSFEDIHCYREQIKRVKDSEDVPMVLVGNKCDLPSRTVDTKQAQDLARSYGIPFIETSAKTRQRVEDAFYTLVREIRKHKEKMSKDGKKKKKKSKTKCVIM |
| SEQ ID NO: 23 | RALA G23C | MAANKPGQNSLALHKVIMVGSCGVGKSALTLQFMYDEFVEDYEPTKADSYRKKVVLDGEEVQIDILDTAGQEDYAAIRDNYFRSGEGFLCVFSITEMESFAATADFREQILRVKEDENVPFLLVGNKSDLEDKRQVSVEEAKNRAEQWNVNYVETSAKTRANVDKVFFDLMREIRARKMEDSKEKNGKKKRKSLAKRIRERCCIL |
| SEQ ID NO: 24 | RALB G23C | MAANKSKGQSSLALHKVIMVGSCGVGKSALTLQFMYDEFVEDYEPTKADSYRKKVVLDGEEVQIDILDTAGQEDYAAIRDNYFRSGEGFLLVFSITEHESFTATAEFREQILRVKAEEDKIPLLVVGNKSDLEERRQVPVEEARSKAEEWGVQYVETSAKTRANVDKVFFDLMREIRTKKMSENKDKNGKKSSKNKKSFKERCCLL |
| SEQ ID NO: 25 | RALA 11-183 G23C | SLALHKVIMVGSCGVGKSALTLQFMYDEFVEDYEPTKADSYRKKVVLDGEEVQIDILDTAGQEDYAAIRDNYFRSGEGFLCVFSITEMESFAATADFREQILRVKEDENVPFLLVGNKSDLEDKRQVSVEEAKNRAEQWNVNYVETSAKTRANVDKVFFDLMREIRARKMEDS |
| SEQ ID NO: 26 | RALB 11-183 G23C | SLALHKVIMVGSCGVGKSALTLQFMYDEFVEDYEPTKADSYRKKVVLDGEEVQIDILDTAGQEDYAAIRDNYFRSGEGFLLVFSITEHESFTATAEFREQILRVKAEEDKIPLLVVGNKSDLEERRQVPVEEARSKAEEWGVQYVETSAKTRANVDKVFFDLMREIRTKKMSE |
| SEQ ID NO: 27 | KRAS isoform b E62C | MTEYKLVVVGAGGVGKSALTIQLIQNHFVDEYDPTIEDSYRKQVVIDGETCLLDILDTAGQCEYSAMRDQYMRTGEGFLCVFAINNTKSFEDIHHYREQIKRVKDSEDVPMVLVGNKCDLPSRTVDTKQAQDLARSYGIPFIETSAKTRQGVDDAFYTLVREIRKHKEKMSKDGKKKKKKSKTKCVIM |
| SEQ ID NO: 28 | KRAS isoform b D92C | MTEYKLVVVGAGGVGKSALTIQLIQNHFVDEYDPTIEDSYRKQVVIDGETCLLDILDTAGQEEYSAMRDQYMRTGEGFLCVFAINNTKSFECIHHYREQIKRVKDSEDVPMVLVGNKCDLPSRTVDTKQAQDLARSYGIPFIETSAKTRQGVDDAFYTLVREIRKHKEKMSKDGKKKKKKSKTKCVIM |
| SEQ ID NO: 29 | KRAS isoform b H95C | MTEYKLVVVGAGGVGKSALTIQLIQNHFVDEYDPTIEDSYRKQVVIDGETCLLDILDTAGQEEYSAMRDQYMRTGEGFLCVFAINNTKSFEDIHCYREQIKRVKDSEDVPMVLVGNKCDLPSRTVDTKQAQDLARSYGIPFIETSAKTRQGVDDAFYTLVREIRKHKEKMSKDGKKKKKKSKTKCVIM |
| SEQ ID NO: 30 | KRAS isoform b G12D E62C | MTEYKLVVVGADGVGKSALTIQLIQNHFVDEYDPTIEDSYRKQVVIDGETCLLDILDTAGQCEYSAMRDQYMRTGEGFLCVFAINNTKSFEDIHHYREQIKRVKDSEDVPMVLVGNKCDLPSRTVDTKQAQDLARSYGIPFIETSAKTRQGVDDAFYTLVREIRKHKEKMSKDGKKKKKKSKTKCVIM |
| SEQ ID NO: 31 | KRAS isoform b G12D D92C | MTEYKLVVVGADGVGKSALTIQLIQNHFVDEYDPTIEDSYRKQVVIDGETCLLDILDTAGQEEYSAMRDQYMRTGEGFLCVFAINNTKSFECIHHYREQIKRVKDSEDVPMVLVGNKCDLPSRTVDTKQAQDLARSYGIPFIETSAKTRQGVDDAFYTLVREIRKHKEKMSKDGKKKKKKSKTKCVIM |
| SEQ ID NO: 32 | KRAS isoform b G12D H95C | MTEYKLVVVGADGVGKSALTIQLIQNHFVDEYDPTIEDSYRKQVVIDGETCLLDILDTAGQEEYSAMRDQYMRTGEGFLCVFAINNTKSFEDIHCYREQIKRVKDSEDVPMVLVGNKCDLPSRTVDTKQAQDLARSYGIPFIETSAKTRQGVDDAFYTLVREIRKHKEKMSKDGKKKKKKSKTKCVIM |
| SEQ ID NO: 33 | KRAS isoform a 1-169 E62C | MTEYKLVVVGAGGVGKSALTIQLIQNHFVDEYDPTIEDSYRKQVVIDGETCLLDILDTAGQCEYSAMRDQYMRTGEGFLCVFAINNTKSFEDIHHYREQIKRVKDSEDVPMVLVGNKCDLPSRTVDTKQAQDLARSYGIPFIETSAKTRQRVEDAFYTLVREIRQYRLK |
| SEQ ID NO: 34 | KRAS isoform a 1-169 D92C | MTEYKLVVVGAGGVGKSALTIQLIQNHFVDEYDPTIEDSYRKQVVIDGETCLLDILDTAGQEEYSAMRDQYMRTGEGFLCVFAINNTKSFECIHHYREQIKRVKDSEDVPMVLVGNKCDLPSRTVDTKQAQDLARSYGIPFIETSAKTRQRVEDAFYTLVREIRQYRLK |
| SEQ ID NO: 35 | KRAS isoform a 1-169 H95C | MTEYKLVVVGAGGVGKSALTIQLIQNHFVDEYDPTIEDSYRKQVVIDGETCLLDILDTAGQEEYSAMRDQYMRTGEGFLCVFAINNTKSFEDIHCYREQIKRVKDSEDVPMVLVGNKCDLPSRTVDTKQAQDLARSYGIPFIETSAKTRQRVEDAFYTLVREIRQYRLK |
| SEQ ID NO: 36 | KRAS isoform a 1-169 G12D E62C | MTEYKLVVVGADGVGKSALTIQLIQNHFVDEYDPTIEDSYRKQVVIDGETCLLDILDTAGQCEYSAMRDQYMRTGEGFLCVFAINNTKSFEDIHHYREQIKRVKDSEDVPMVLVGNKCDLPSRTVDTKQAQDLARSYGIPFIETSAKTRQRVEDAFYTLVREIRQYRLK |
| SEQ ID NO: 37 | KRAS isoform a 1-169 G12D D92C | MTEYKLVVVGADGVGKSALTIQLIQNHFVDEYDPTIEDSYRKQVVIDGETCLLDILDTAGQEEYSAMRDQYMRTGEGFLCVFAINNTKSFECIHHYREQIKRVKDSEDVPMVLVGNKCDLPSRTVDTKQAQDLARSYGIPFIETSAKTRQRVEDAFYTLVREIRQYRLK |
| SEQ ID NO: 38 | KRAS isoform a 1-169 G12D H95C | MTEYKLVVVGADGVGKSALTIQLIQNHFVDEYDPTIEDSYRKQVVIDGETCLLDILDTAGQEEYSAMRDQYMRTGEGFLCVFAINNTKSFEDIHCYREQIKRVKDSEDVPMVLVGNKCDLPSRTVDTKQAQDLARSYGIPFIETSAKTRQRVEDAFYTLVREIRQYRLK |
| SEQ ID NO: 39 | KRAS isoform b 1-169 E62C | MTEYKLVVVGAGGVGKSALTIQLIQNHFVDEYDPTIEDSYRKQVVIDGETCLLDILDTAGQCEYSAMRDQYMRTGEGFLCVFAINNTKSFEDIHHYREQIKRVKDSEDVPMVLVGNKCDLPSRTVDTKQAQDLARSYGIPFIETSAKTRQGVDDAFYTLVREIRKHKEK |
| SEQ ID NO: 40 | KRAS isoform b 1-169 D92C | MTEYKLVVVGAGGVGKSALTIQLIQNHFVDEYDPTIEDSYRKQVVIDGETCLLDILDTAGQEEYSAMRDQYMRTGEGFLCVFAINNTKSFECIHHYREQIKRVKDSEDVPMVLVGNKCDLPSRTVDTKQAQDLARSYGIPFIETSAKTRQGVDDAFYTLVREIRKHKEK |
| SEQ ID NO: 41 | KRAS isoform b 1-169 H95C | MTEYKLVVVGAGGVGKSALTIQLIQNHFVDEYDPTIEDSYRKQVVIDGETCLLDILDTAGQEEYSAMRDQYMRTGEGFLCVFAINNTKSFEDIHCYREQIKRVKDSEDVPMVLVGNKCDLPSRTVDTKQAQDLARSYGIPFIETSAKTRQGVDDAFYTLVREIRKHKEK |
| SEQ ID NO: 42 | KRAS isoform b 1-169 G12D E62C | MTEYKLVVVGADGVGKSALTIQLIQNHFVDEYDPTIEDSYRKQVVIDGETCLLDILDTAGQCEYSAMRDQYMRTGEGFLCVFAINNTKSFEDIHHYREQIKRVKDSEDVPMVLVGNKCDLPSRTVDTKQAQDLARSYGIPFIETSAKTRQGVDDAFYTLVREIRKHKEK |

TABLE 1-continued

| SEQ ID NO: 43 | KRAS isoform b 1-169 G12D D92C | MTEYKLVVVGADGVGKSALTIQLIQNHFVD EYDPTIEDSYRKQVVIDGETCLLDILDTAG QEEYSAMRDQYMRTGEGFLCVFAINNTKSF ECIHHYREQIKRVKDSEDVPMVLVGNKCDL PSRTVDTKQAQDLARSYGIPFIETSAKTRQ GVDDAFYTLVREIRKHKEK |
|---|---|---|
| SEQ ID NO: 44 | KRAS isoform b 1-169 G12D H95C | MTEYKLVVVGADGVGKSALTIQLIQNHFVD EYDPTIEDSYRKQVVIDGETCLLDILDTAG QEEYSAMRDQYMRTGEGFLCVFAINNTKSF EDIHCYREQIKRVKDSEDVPMVLVGNKCDL PSRTVDTKQAQDLARSYGIPFIETSAKTRQ GVDDAFYTLVREIRKHKEK |
| SEQ ID NO: 45 | WT RRAS2 isoform b | MREQYMRTGEGFLLVFSVTDRGSFEEIYKF QRQILRVKDRDEFPMILIGNKADLDHQRQV TQEEGQQLARQLKVTYMEASAKIRMNVDQA FHELVRVIRKFQEQECPPSPEPTRKEKDKK GCHCVIF |
| SEQ ID NO: 46 | WT RRAS2 isoform c | MSYFVTDYDPTIEDSYTKQCVIDDRAARLD ILDTAGQEEFGAMREQYMRTGEGFLLVFSV TDRGSFEEIYKFQRQILRVKDRDEFPMILI GNKADLDHQRQVTQEEGQQLARQLKVTYME ASAKIRMNVDQAFHELVRVIRKFQEQECPP SPEPTRKEKDKKGCHCVIF |
| SEQ ID NO: 47 | WT RIT1 isoform 1 | MERWLFLGATEEGPKRTMDSGTRPVGSCCS SPAGLSREYKLVMLGAGGVGKSAMTMQFIS HRFPEDHDPTIEDAYKIRIRIDDEPANLDI LDTAGQAEFTAMRDQYMRAGEGFIICYSIT DRRSFHEVREFKQLIYRVRRTDDTPVVLVG NKSDLKQLRQVTKEEGLALAREFSCPFFET SAAYRYYIDDVFHALVREIRRKEKEAVLAM EKKSKPKNSVWKRLKSPFRKKKDSVT |
| SEQ ID NO: 48 | WT RIT1 isoform 3 | MTMQFISHRFPEDHDPTIEDAYKIRIRIDD EPANLDILDTAGQAEFTAMRDQYMRAGEGF IICYSITDRRSFHEVREFKQLIYRVRRTDD TPVVLVGNKSDLKQLRQVTKEEGLALAREF SCPFFETSAAYRYYIDDVFHALVREIRRKE KEAVLAMEKKSKPKNSVWKRLKSPFRKKKD SVT |

In some embodiments, a competition reaction comprises, in addition to a competition probe, one or more test compounds (e.g., 1, 2, 3, 4, 5, 10, 25, 50, or more test compounds). Test compounds may be drawn from a library of test compounds, such as a library of 100, 1000, 5000, 10000, 50000, 100000, or more compounds. In some embodiments, a test compound that competes for binding with the competition probe is identified as binding to the mutant Ras. The test compound may interact with Ras via a chemical bond selected from the group consisting of a hydrogen bond, van der Waals interaction, ionic bond, covalent bond, hydrophobic interaction, and any combination thereof. In some embodiments, the test compound interacts with the Switch II binding pocket of Ras. In general, the degree of competition with the competition probe is indicative of affinity of a test compound for the mutant Ras. In some embodiments, the test compound binds to Ras with a $K_d$ of about or at least about 100 pM, 200 pM, 300 pM, 400 pM, 500 pM, 600 pM, 700 pM, 800 pM, 900 pM, 1 nM, 2 nM, 3 nM, 4 nM, 5 nM, 6 nM, 7 nM, 8 nM, 9 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 1 µM, 2 µM, 3 µM, 4 µM, 5 µM, 6 µM, 7 µM, 8 µM, 9 µM, 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 150 µM, 200 µM, 250 µM, 300 µM, 350 µM, 400 µM, 450 µM, or 500 µM. In some embodiments, the test compound binds to Ras with a $K_d$ of up to about 100 pM, 200 pM, 300 pM, 400 pM, 500 pM, 600 pM, 700 pM, 800 pM, 900 pM, 1 nM, 2 nM, 3 nM, 4 nM, 5 nM, 6 nM, 7 nM, 8 nM, 9 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 1 µM, 2 µM, 3 µM, 4 µM, 5 µM, 6 µM, 7 µM, 8 µM, 9 µM, 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 150 µM, 200 µM, 250 µM, 300 µM, 350 µM, 400 µM, 450 µM, or 500 µM. In some embodiments, the competition probe binds Ras with a Kd of between 100 pM to 50 nm, or 500 pM to 1 nM.

In some embodiments, the test compound binds to a GDP-bound Ras protein with a $K_d$ of at most 100 µM, thereby antagonizing Ras activity. Antagonizing Ras activity can be measured in a variety of ways, with respect to one or more of Ras functions or downstream effects. Non-limiting examples of Ras activity that may be antagonized by a test compound include modulation of GTPase activity, nucleotide exchange, effector protein binding, effector protein activation, guanine exchange factor (GEF) binding, GEF-facilitated nucleotide exchange, phosphate release, nucleotide release, nucleotide binding, Ras subcellular localization, Ras post-translational processing, or Ras post-translational modification. In some embodiments, the test compound inhibits the binding or release of GDP or GTP to a Ras protein.

In some embodiments, a decrease in binding between the mutant Ras and the competition probe in the presence of one or more test compounds (e.g., as indicated by a decrease in modification of the mutant Ras by the competition probe) is indicative of Ras antagonist activity of the one or more test compounds. Accordingly, a test compound associated with such a decrease in competition probe binding may be selected as a Ras antagonist. In some embodiments, a test compound is selected as a Ras antagonist if competition probe binding is reduced by at least a specified threshold degree (e.g., expressed as a percentage). The decrease in binding may be measured with respect to a control reaction, such as a reaction comprising the same concentrations of competition probe and mutant Ras reacted for the same amount of time but lacking any test compound. In some embodiments, the decrease in binding between the mutant Ras and the competition probe is about or at least about 5, 10, 25, 50, 75, 80, 85, 90, 95, 96, 97, 98, 99, or 100%. In some embodiments, the decrease in binding between the mutant Ras and the competition probe is at least about 75%.

Degree of binding between a competition probe and a mutant Ras (and decreases thereof) can be measured by any suitable method. The method selected may depend on the nature of the modification to the mutant Ras (e.g., addition of a detectable label and/or formation of a complex between the mutant Ras and the competition probe). For convenient detection of competition probe-mutant Ras complexes formed during an assay, a Ras, mutant Ras, or competition probe can be conjugated to a detectable label. Suitable detectable labels can include any composition detectable by photochemical, biochemical, spectroscopic, immunochemical, electrical, optical, or chemical means. A wide variety of appropriate detectable labels are known in the art, which include fluorescent labels, chemiluminescent labels, radioactive isotope labels, stable isotope labels, enzymatic labels, and ligands.

Detectable labels can be added to competition probes or test compounds by any well-known chemical method that does not ablate compound binding. This can be ascertained by identifying positions on the compound scaffold that contact solvent in an appropriate x-ray crystal structure (such as FIG. 2), or by identifying positions on a molecule where the addition of lengthy substituents does not dramatically affect the ability of the compound to bind to Ras, and by conjugating the detectable label to the core directly or indirectly. In compounds based on the 4-(piperazinyl)quinazoline core such as CP-001, appropriate positions for conjugation include (but are not limited to) the 4-position nitrogen of the piperazinyl moiety occupied by R1 or the 2-position carbon of the quinazolyl moiety.

In some embodiments, a competition probe or test compound has a structure of Formula I:

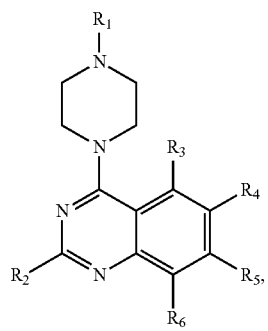

(Formula I)

or a pharmaceutically acceptable salt thereof, wherein:

$R_1$ is selected from the group consisting of H, alkyl, substituted alkyl, acyl, heterocycle, substituted heterocycle, aryl, substituted aryl, heteroaryl, substituted heteroaryl, and any combination thereof;

$R_2$ is selected from the group consisting of H, alkyl, substituted alkyl, heteroalkyl, substituted heteroalkyl, alkoxy, amino, aminoalkyl, alkylamino, heterocycle, substituted heterocycle, aryl, substituted aryl, heteroaryl, substituted heteroaryl, and any combination thereof;

each of $R_3$, $R_4$, $R_5$, and $R_6$ is independently selected from the group consisting of H, alkyl, substituted alkyl, halogen, hydroxyl, cyano, heterocycle, substituted heterocycle, aryl, substituted aryl, heteroaryl, substituted heteroaryl, and any combination thereof.

In some embodiments, the heterocycle, substituted heterocycle, aryl, substituted aryl, heteroaryl, or substituted heteroaryl of $R_1$, $R_2$, $R_3$, $R_4$, $R_5$, and/or $R_6$ is a 5- or 6-membered ring.

In some embodiments, the substituted heterocycle, substituted aryl, or substituted heteroaryl of $R_1$, $R_2$, $R_3$, $R_4$, $R_5$, and/or $R_6$ is substituted with one or more substituents selected from the group consisting of alkyl, substituted alkyl, halogen, hydroxyl, cyano, and any combination thereof.

In some embodiments, $R_1$ or $R_2$ is conjugated to a detectable label or comprises an electrophile. In some embodiments, the electrophile is selected from

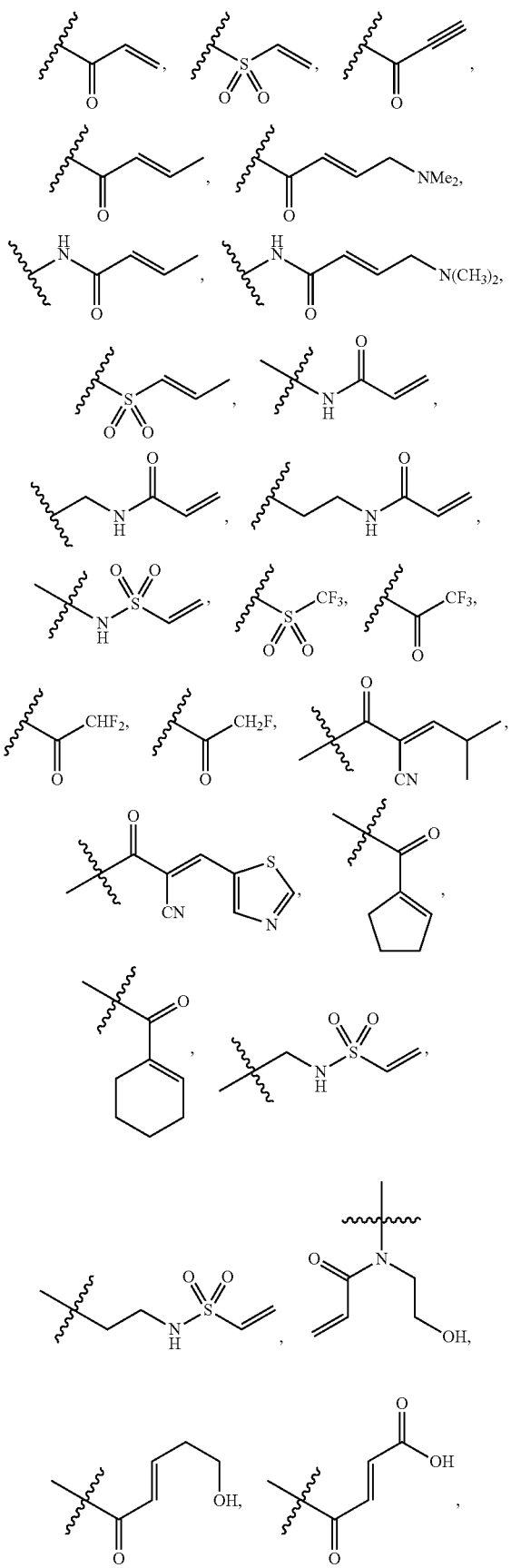

-continued

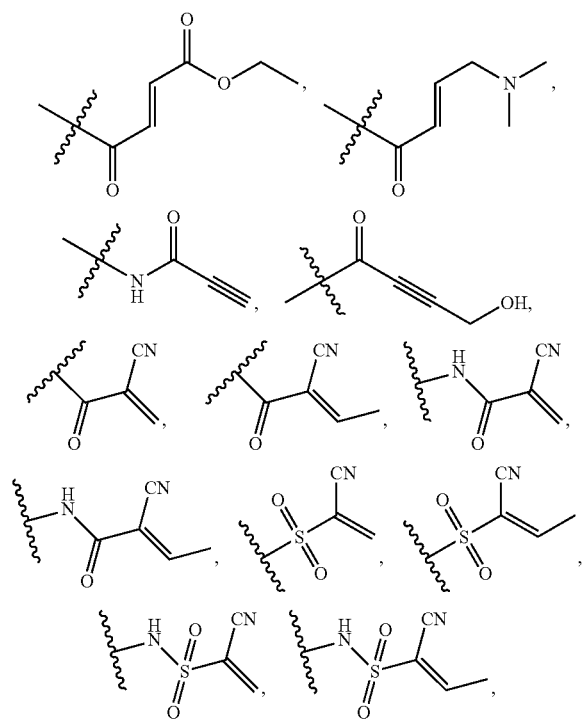

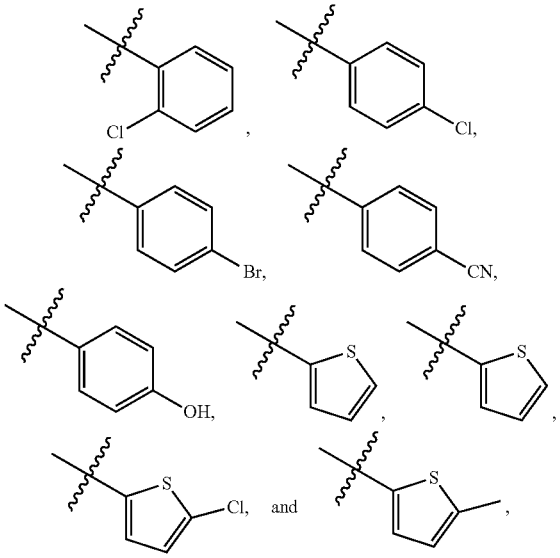

and any combination thereof.

In some embodiments, $R_5$ is selected from the group consisting of H, halogen (e.g., Cl), and

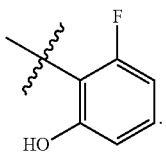 [SMILES: *c1c(O)cccc1F]

In some embodiments, $R_6$ is H or halogen (e.g., F).

In some embodiments, a compound of Formula I is represented by a structure of Formula II:

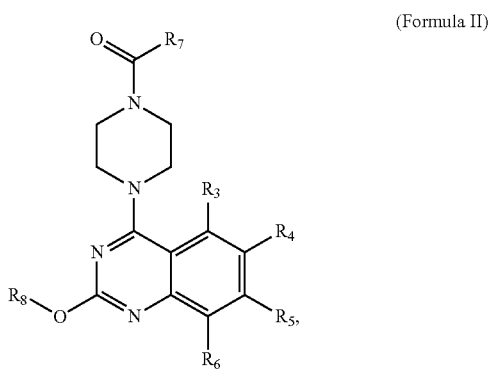

(Formula II)

or a pharmaceutically acceptable salt thereof, wherein:

$R_7$ is selected from the group consisting of H, alkyl, substituted alkyl, and any combination thereof; and $R_8$ is selected from the group consisting of H, alkyl, substituted alkyl, heterocycle, substituted heterocycle, aryl, substituted aryl, heteroaryl, substituted heteroaryl, and any combination thereof.

In some embodiments, a compound of Formula I is represented by a structure of Formula III:

and any combination thereof.

In some embodiments, $R_1$ is selected from the group consisting of H, alkyl, substituted alkyl, acyl, and any combination thereof. In some embodiments, $R_1$ is

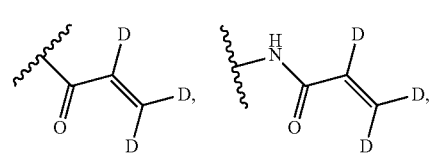

In some embodiments, $R_2$ is selected from the group consisting of H, heteroalkyl, substituted heteroalkyl, alkoxy, amino, aminoalkyl, alkylamino, heterocycle, substituted heterocycle, and any combination thereof.

In some embodiments, $R_3$ is selected from the group consisting of H, alkyl, substituted alkyl, halogen, hydroxyl, cyano, and any combination thereof. In some embodiments, $R_3$ is H.

In some embodiments, $R_4$ is selected from the group consisting of H, Cl,

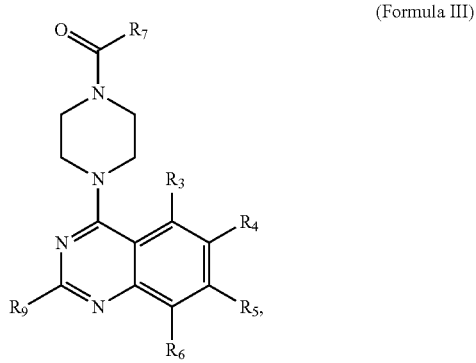

(Formula III)

or a pharmaceutically acceptable salt thereof, wherein:

$R_7$ is selected from the group consisting of H, alkyl, substituted alkyl, and any combination thereof; and $R_9$ is selected from the group consisting of H, alkyl, substituted alkyl, heteroalkyl, substituted heteroalkyl, alkoxy, amino, aminoalkyl, alkylamino, heterocycle, substituted heterocycle, aryl, substituted aryl, heteroaryl, substituted heteroaryl, and any combination thereof.

In some embodiments, $R_9$ is selected from the group consisting of H, heteroalkyl, substituted heteroalkyl, alkoxy, amino, aminoalkyl, alkylamino, heterocycle, substituted heterocycle, and any combination thereof.

In some embodiments, a compound of Formula I is represented by a structure of Formula IV:

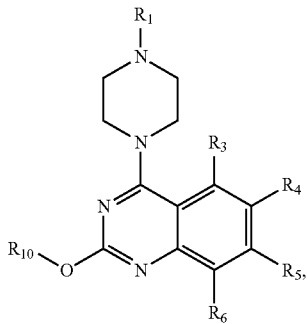

(Formula IV)

or a pharmaceutically acceptable salt thereof, wherein:

$R_{10}$ is selected from the group consisting of H, alkyl, substituted alkyl, heterocycle, substituted heterocycle, aryl, substituted aryl, heteroaryl, substituted heteroaryl, and any combination thereof.

In some embodiments, a compound of Formula I is represented by a structure of Formula V:

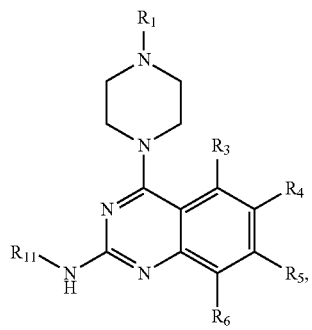

(Formula V)

or a pharmaceutically acceptable salt thereof, wherein:

$R_{11}$ is selected from the group consisting of H, alkyl, substituted alkyl, heterocycle, substituted heterocycle, aryl, substituted aryl, heteroaryl, substituted heteroaryl, and any combination thereof.

In some embodiments, a compound of Formula I is represented by a structure of Formula VI:

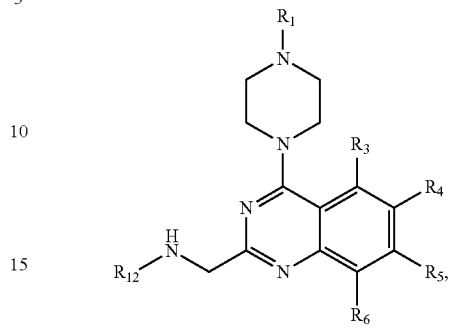

(Formula VI)

or a pharmaceutically acceptable salt thereof, wherein:

$R_{12}$ is selected from the group consisting of H, alkyl, substituted alkyl, heterocycle, substituted heterocycle, aryl, substituted aryl, heteroaryl, substituted heteroaryl, and any combination thereof.

In some embodiments, $R_1$, $R_2$, $R_7$, $R_8$, $R_9$, $R_{10}$, $R_{11}$, or $R_{12}$ is conjugated to a detectable label or comprises an electrophile.

In some embodiments, a compound of Formula I, II, III, IV, V, or VI is conjugated to a detectable label.

The chemical entities described herein can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes.

Although various steps are described and depicted in Schemes A-C, the steps in some cases may be performed in a different order than the order shown in Schemes A-C. Various modifications to these synthetic reaction schemes may be made and will be suggested to one skilled in the art having referred to the disclosure contained in this Application.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

In some embodiments, a competition probe or test compound of Formula III is accessed synthetically by scheme A:

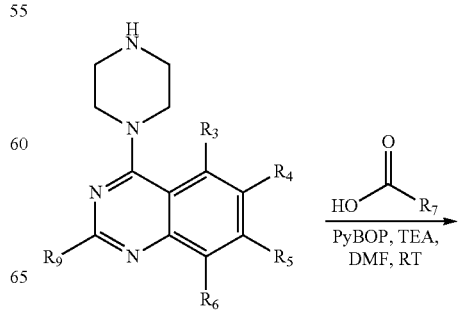

In some embodiments, a competition probe or test compound of formula V is accessed synthetically by scheme C:
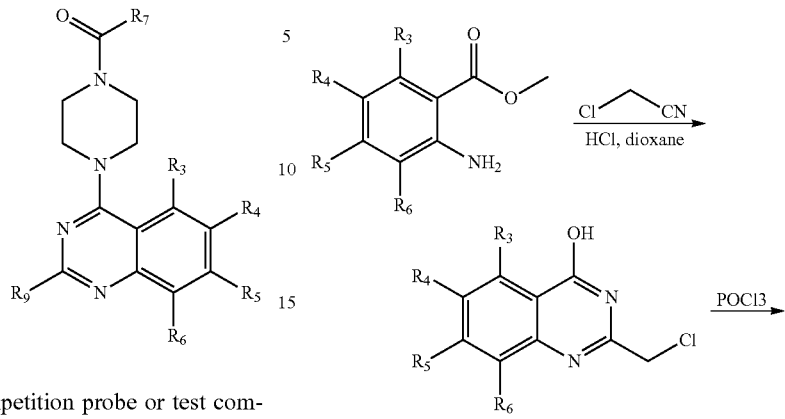
In some embodiments, a competition probe or test compound of Formula IV is accessed synthetically by scheme B:
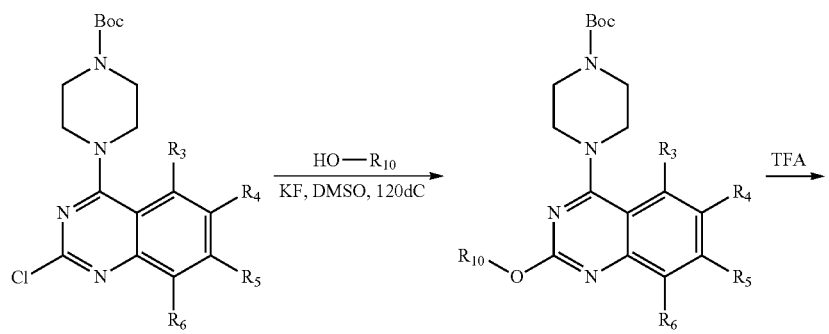
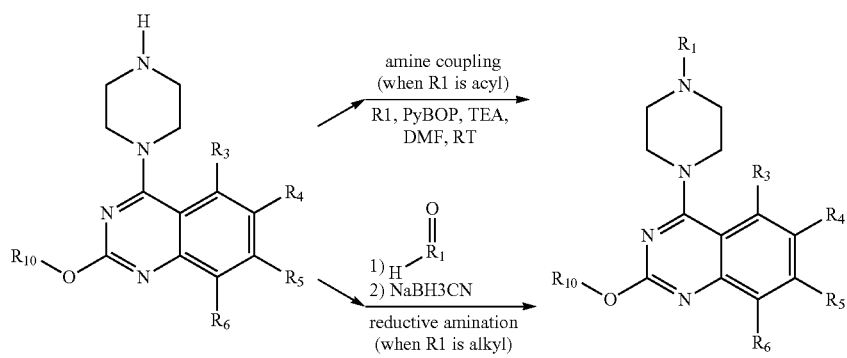

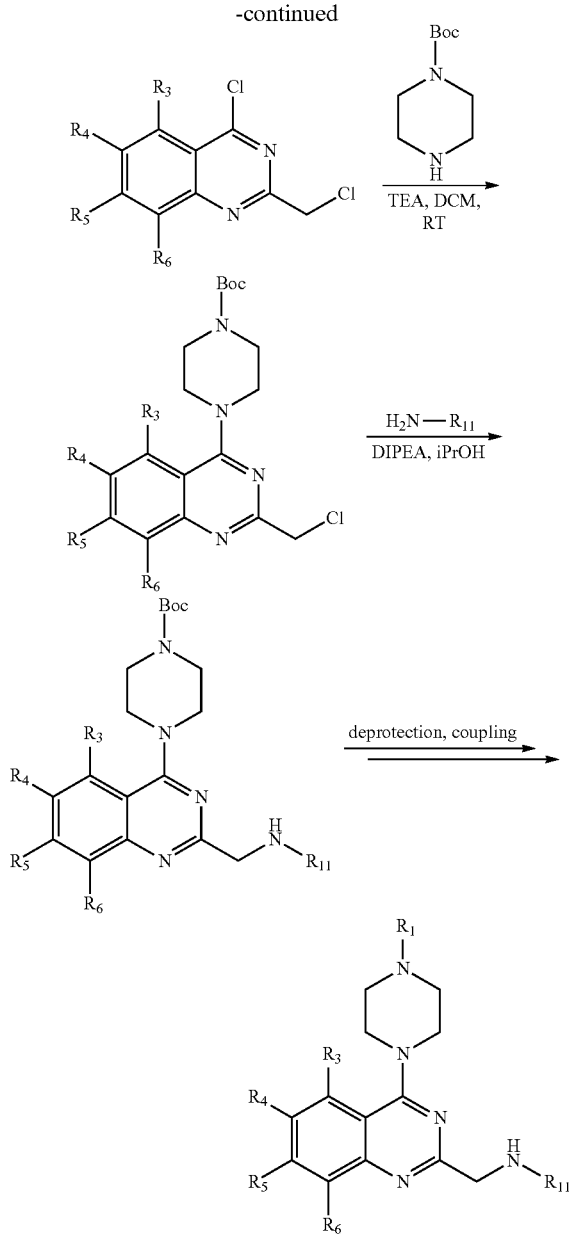

Detectable labels can be added to Ras mutants by any of a variety of chemical methods that do not disrupt protein folding/activity. In some embodiments, detectable labels are conjugated to cysteines on Ras via reaction with an appropriate maleimide-conjugated probe in the presence of tris (carboxyethyl)phosphine (TCEP) in a buffer solution at physiological pH. In some embodiments, detectable labels are conjugated to lysines on Ras via reaction with an appropriate N-hydroxysuccinimide (NHS)-conjugated probe in 0.1M sodium carbonate buffer solution. In some embodiments, detectable labels are conjugated to Ras by: a) first translating Ras in the presence of L-Azidohomoalanine or L-homopropargylglycine (both incorporated at the site of methionine residues) to produce a Ras incorporating unnatural amino acid residues, and b) reacting the unnatural amino acid residue bearing Ras with azide- or alkyne-derivatized detectable probes under suitable "click" chemistry reaction conditions.

Fluorescent labels include both protein and non-protein organic fluorophores, as well as organometallic fluorophores. Protein fluorophores known to those of skill in the art include green fluorescent proteins (GFPs, fluorescent proteins that fluoresce in the green region of the spectrum, generally emitting light having a wavelength from 500-550 nanometers), cyan-fluorescent proteins (CFPs, fluorescent proteins that fluoresce in the cyan region of the spectrum, generally emitting light having a wavelength from 450-500 nanometers), red fluorescent proteins (RFPs, fluorescent proteins that fluoresce in the red region of the spectrum, generally emitting light having a wavelength from 600-650 nanometers). Specific embodiments of protein fluorophores known to those in the art additionally include mutants and spectral variants of these proteins that retain their fluorescent properties, of which non-limiting examples are AcGFP, AcGFP1, AmCyan, AmCyan1, AQ143, AsRed2, Azami Green, Azurite, BFP, Cerulean, CFP, CGFP, Citrine, copGFP, CyPet, dKeima-Tandem, DsRed, dsRed-Express, DsRed-Monomer, DsRed2, dTomato, dTomato-Tandem, EBFP, EBFP2, ECFP, EGFP, Emerald, EosFP, EYFP, GFP, HcRed-Tandem, HcRed1, JRed, Katuska, Kusabira Orange, Kusabira Orange2, mApple, mBanana, mCerulean, mCFP, mCherry, mCitrine, mECFP, mEmerald, mGrape1, mGrape2, mHoneydew, Midori-Ishi Cyan, mKeima, mKO, mOrange, mOrange2, mPlum, mRaspberry, mRFP1, mRuby, mStrawberry, mTagBFP, mTangerine, mTeal, mTomato, mTurquoise, mWasabi, PhiYFP, ReAsH, Sapphire, Superfolder GFP, T-Sapphire, TagCFP, TagGFP, TagRFP, TagRFP-T, TagYFP, tdTomato, Topaz, TurboGFP, Venus, YFP, YPet, ZsGreen, and ZsYellow1. Specific embodiments of protein fluorophores also include phycobiliproteins and fragments of phycobiliproteins, of which non-limiting examples are A-phycoerythrin, B-phycoerythrin, C-phycocyanin, allophycocyanin, XL665, or d2. Non-protein organic fluorophores known to those of skill in the art include, but are not limited to, xanthene derivatives (of which common examples are fluorescein, rhodamine, Oregon green, eosin, and texas red), cyanine derivatives (of which common examples are cyanine, indocarbocyanine, oxacorbocyanine, thiacarbocyanine, and merocyanine), squaraine derivatives (of which common examples are Seta, SeTau, and Square dyes), naphthalene derivatives (of which common examples are dansyl and prodan), coumarin derivatives, oxadiazole derivatives (of which common examples are pyridyloxazole, nitrobenzoxadiazole, and benzoxadiazole), anthracene derivatives (of which common examples are anthraquinones such as DRAQ5, DRAQ7, and CyTRAK Orange), pyrene derivatives (of which a common examples is cascade blue), oxazine derivatives (of which common examples are Nile Red, Nile Blue, Cresyl Violet, and oxazine 170), acridine derivatives (of which common examples are proflavin, acridine orange, and acridine yellow), arylmethine derivatives (of which common examples are auramine, crystal violet, and malachite green), and tetrapyrrole derivatives (of which common examples are porphyrin, phthalocyanine, and bilirubin). Such organic fluorophores may be additionally derivatized with an amino, hydroxyl, or succinimide group to facilitate chemical attachment. Non-protein organic fluorophores also include the near-IR HTRF acceptor d2. Organometallic fluorophores include lanthanide ion chelates, nonlimiting examples of which include tris(dibenzoylmethane) mono(1,10-phenanthroline)europium(lll), tris(dibenzoylmethane) mono(5-amino-1,10-phenanthroline)europium (lll), and Lumi4-Tb cryptate.

Chemiluminescent labels include enzymes of the luciferase class, which produce light upon combination with suitable substrates and cofactors. There are variety of commercially used recombinant luciferases with different primary sequences and different cofactor requirements. Non-limiting examples include *Cypridina, Gaussia, Renilla*, and Firefly luciferases.

Enzymatic labels include horseradish peroxidase (HRP), alkaline phosphatase (AP), beta-galactosidase, glucose oxidase, and other well-known labels. The presence or binding of such labels can be detected by the application of detection reagents, which are compositions comprising a substrate which produces a detectable signal upon reaction with the enzyme in the detection zone. The detectable signal may be colorimetric or luminescent. As one example of an enzyme-detection reagent pair, HRP produces blue light when reacted with luminol in the presence of $H_2O_2$. As another example of an enzyme-detection reagent pair, AP produces a yellow reaction product when combined with p-nitrophenyl phosphate (pNPP). Enzymatic labels may be conjugated to amino or sulfhydryl groups of Ras by methods similar to those used to conjugate them to antibodies. Such methods include crosslinking using glutaraldehyde or 2-step crosslinking using heterobifunctional crosslinkers such as succinimidyl 4-(N-maleimidomethyl)cyclohexane-1-carboxylate (SMCC) or sulfosuccinimidyl 4-(N-maleimidomethyl) cyclohexane-1-carboxylate (sulfo-SMCC).

Radioactive isotope labels include, but are not limited to, $^3H$, $^{14}C$, $^{22}Na$, $^{32}P$, $^{33}P$ $^{35}S$, $^{42}K$, $^{45}Ca$, $^{59}Fe$, $^{125}I$, $^{203}Hg$, or the like. Such radioactive isotope labels can either be conjugated to a small molecule or protein of the invention or incorporated into the explicit structure of a protein or a small molecule of the invention. As an example of the former, amino groups on proteins or small molecules can be reacted with $^{14}C$-paraformaldehyde followed by sodium cyanoborohydride to add a detectable $^{14}C$-methyl group via reductive amination. As an example of the latter, a protein may be translated in the presence of $^{35}S$-methionine to produce a protein with a detectable $^{35}S$ atom at the site of methionine residues.

Stable isotope labels suitable for detection comprise chemical moieties incorporating specific heavy isotopes of elements present in biomolecules such as $^2H$, $^{13}C$, $^{15}N$, $^{18}O$, $^{33}S$, or $^{34}S$ which can either be conjugated to a small molecule or protein of the invention or incorporated into the explicit structure of a protein or a small molecule of the invention. As an example of the former, amino groups (either on proteins or small molecules) can be reacted with $^{13}C$-acetaldehyde or $^{13}C$-acetyl chloride to covalently add an acetyl moiety that can be detected. As an example of the latter, a protein can be translated in the presence of $^{13}C$-arginine (to produce a protein containing a detectable $^{13}C$ atom at the sites of arginine residues), or a small molecule synthetic step utilizing acetic anhydride can instead substitute $^{13}C$-acetic anhydride to produce a molecule having a detectable $^{13}C$ atom at the site of an existing acetyl group. Many general synthetic methods in commercial and research use for stable isotope labeling are also useful for radioactive isotope labeling, and vice versa.

Ligands suitable for detection are those for which a well-characterized receptor partner is available, and the ligand-receptor interaction serves to detect or isolate the ligand. The ligand/receptor pair can be either natural or non-natural. Non-limiting examples of natural ligand-receptor pairs include maltose/maltose binding protein (MBP), glutathione/glutathione-S-transferase (GST), calmodulin/calmodulin binding protein, IgG/protein G, IgG/protein A, and biotin/streptavidin. Non-limiting examples of non-natural ligand/receptor pairs include polyhistidine/Ni-nitriloacetic acid (NTA), FLAG peptide/anti-FLAG antibody. The ligand/receptor pair can also comprise two small molecule fragments, as in the case of "click" reaction pairs such as azide/alkyne (Huisgen cycloaddition), azide/cyclooctyne (Huisgen cycloaddition), or azide with phosphine or phosphite (Staudinger ligation).

The detection methods used to detect or quantify the label will typically depend upon the label selected. For example, radiolabels (e.g., radioactive isotope labels) may be detected using photographic film or a phosphoimager. Stable isotope labels (e.g., $^{13}C$-acetyl) can be detected by nuclear magnetic resonance (NMR) or mass spectrometry (MS). Fluorescent labels (e.g., fluorescent dyes, fluorescent proteins) may be detected and quantified using a photodetector to detect emitted light. In some embodiments, each of a plurality of probes in a single reaction is conjugated to a different detectable label (e.g., fluorescent dyes with different emission spectra), such that the signal corresponding to different targets can be differentiated. In some embodiments, fluorescent dyes used as detectable labels have overlapping emission and absorption spectra such that binding or proximity of elements conjugated to the fluorescent dyes can be detected by Förster resonance energy transfer (FRET). A number of suitable methods for detecting FRET are known by those of skill in the art, of which sensitized emission (SE), acceptor bleaching (AB), donor quenching, and fluorescence lifetime spectroscopy are non-limiting examples. Enzymatic labels are typically detected by providing the enzyme with a substrate and measuring the reaction product produced by the action of the enzyme on the substrate. Colorimetric labels are typically detected by visualizing the colored label or are quantified using a spectrophotometer. In some embodiments, binding to or modification by a competition probe is measured by mass spectrometry.

Competition probes may carry a label to facilitate their detection. In a particular embodiment, the label is a fluorescent label. However, the detectable label need not be a fluorescent label. Any label can be used which allows the detection of the binding of the competition probe to a mutant Ras or the covalent modification of a mutant Ras by a competition probe. One method for detecting a fluorescently labeled competition probe comprises using laser light of a wavelength specific for the labeled competition probe, or the use of other suitable sources of illumination. Fluorescence from the label on a competition probe may be detected by a CCD camera or other suitable detection means.

The mutant Ras proteins and competition probes described herein can be used for competition binding assays to screen for reversible binders to the Switch II pocket of Ras. An exemplary illustration in accordance with an embodiment is shown in FIG. 1. In some embodiments, mass spectrometry based assays are performed by evaluating the protein-ligand complex or by monitoring the depletion of the competition probe in the presence of excess protein. For both of these assays, automated high throughput solid phase extraction-mass spectrometry platforms (e.g., Agilent RapidFire) may be used to enable screening of large libraries of test compounds (e.g libraries of more than 100,000 compounds). By modifying the competition probes described herein to introduce fluorescent tags, additional assay formats such as fluorescence polarization or FRET may be used. Modification of the competition probes with an affinity tag (e.g., biotin) may enable additional assay formats such as ELISA or AlphaScreen.

In one aspect, the disclosure provides a method of producing a Ras antagonist. In some embodiments, the method comprises selecting the Ras antagonist according to any of the methods described herein, and synthesizing the compound. Compounds can be synthesized according to any suitable process. Compounds identified as Ras antagonists according to a method disclosed herein may be further tested to assess effects on one or more Ras activities, examples of which are described above. Compounds may also be prepared for use in treating a mutant-Ras-mediated condition of an individual.

In one aspect, the disclosure provides a pharmaceutical composition comprising a Ras antagonist or pharmaceutically acceptable salt thereof selected according to any of the methods described herein. The compositions and methods of the present disclosure may be utilized to treat an individual in need thereof. In certain embodiments, the individual is a mammal such as a human, or a non-human mammal. When administered to an animal, such as a human, the composition or the compound is preferably administered as, or formulated for administration as, a pharmaceutical composition comprising, for example, a Ras antagonist or pharmaceutically acceptable salt thereof selected according to any of the methods, kits, systems, or computer-readable medium described herein and a pharmaceutically acceptable carrier.

A Ras antagonist according to the present disclosure may be administered to an individual by any suitable route of administration, which route may depend on the nature of the formulation. Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections. In some embodiments, the pharmaceutical composition is formulated for oral administration. In other embodiments, the pharmaceutical composition is formulated for injection. In still more embodiments, the pharmaceutical compositions comprise a compound as disclosed herein and an additional therapeutic agent (e.g., anticancer agent). Non-limiting examples of such therapeutic agents are described herein below.

In some embodiments, a pharmaceutical composition is a mixture of a Ras antagonist or pharmaceutically acceptable salt thereof selected according to any of the methods, kits, systems, or computer-readable medium described herein and a pharmaceutically acceptable carrier with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of a Ras antagonist or pharmaceutically acceptable salt thereof selected according to any of the methods, kits, systems, or computer-readable medium described herein are administered in a pharmaceutical composition to a mammal having a disease, disorder or medical condition to be treated. In specific embodiments, the mammal is a human. In certain embodiments, therapeutically effective amounts vary depending on one or more of a variety of factors, including but not limited to, the severity of the disease, the age and relative health of the subject, the potency of the compound used and other factors. A Ras antagonist or pharmaceutically acceptable salt thereof selected according to any of the methods, kits, systems, or computer-readable medium described herein and a pharmaceutically acceptable carrier may be used singly or in combination with one or more therapeutic agents as components of mixtures.

In one aspect, the disclosure provides a reaction mixture comprising one or more mutant Ras, one or more competition probe that is capable of binding the mutant Ras, and one or more test compounds. The mutant Ras can be any mutant Ras described herein. The one or more competition probe can be any competition probe described herein, including combinations of two or more competition probes (e.g., about 1, 2, 3, 4, 5, 10, 15, 25, 50, or more competition probes). The one or more test compound can be any of a variety of test compounds, including one or more test compounds from a library of compounds (e.g., about 1, 2, 3, 4, 5, 10, 15, 25, 50, or more test compounds from a library of 1000, 10000, 50000, 100000, or more compounds). In some embodiments, the mutant Ras comprises a cysteine mutation; the competition probe is capable of covalently modifying the mutant Ras at the cysteine mutation; and the test compound inhibits covalent modification of the mutant Ras by the competition probe. Reaction mixtures can comprise one or more elements disclosed herein in relation to any of the various aspects, in any combination.

In some embodiments, the competition probe competes for binding in the Switch II pocket of the mutant Ras. In some embodiments, the cysteine mutation is not at position 12 or 13 relative to SEQ ID NO: 1 or SEQ ID NO: 2 when optimally aligned. In some embodiments, the cysteine mutation is a mutation relative to position 12 or 13 of SEQ ID NO: 1 or SEQ ID NO: 2 when optimally aligned. In some embodiments, the cysteine mutation is at position 12 or 13 relative to SEQ ID NO: 1 when optimally aligned, and the mutant Ras is selected from mutant MRAS, mutant ERAS, mutant RRAS2, mutant RALA, mutant RALB, mutant RIT1, and any combination thereof. In some embodiments, the cysteine mutation is at a non-conserved amino acid position. In some embodiments, the cysteine mutation is a mutation relative to position 62, 92, or 95 of SEQ ID NO: 1 or SEQ ID NO: 2 when optimally aligned. In some embodiments, the mutant Ras comprises one or more additional mutations. In some embodiments, the test compound interacts with Ras via a chemical bond selected from the group consisting of a hydrogen bond, van der Waals interaction, ionic bond, covalent bond, hydrophobic interaction, and any combination thereof. In some embodiments, the test compound interacts with the Switch II binding pocket of Ras. In some embodiments, the subject reaction mixture comprises a KRAS double mutant based on SEQ ID NO: 1, in which positions 12 and 92 are substituted as G12D and D92C. In some embodiments, the subject method utilizes a KRAS double mutant based on SEQ ID NO: 1, in which positions 12 and 95 are substituted as G12D and H95C. In some embodiments, the subject reaction mixture utilizes a KRAS mutant having a sequence shown in SEQ ID NO: 17, SEQ ID NO: 19, SEQ ID NO: 21, SEQ ID NO: 36, SEQ ID NO: 37, or SEQ ID NO: 38. In some embodiments, the subject method utilizes a KRAS double mutant based on SEQ ID NO: 2, in which positions 12 and 92 are substituted as G12D and D92C. In some embodiments, the subject reaction mixture utilizes a KRAS double mutant based on SEQ ID NO: 2, in which positions 12 and 95 are substituted as G12D and H95C. In some embodiments, the subject reaction mixture utilizes a KRAS mutant having a sequence shown in SEQ ID NO: 30, SEQ ID NO: 31, SEQ ID NO: 32, SEQ ID NO: 42, SEQ ID NO: 43 or SEQ ID NO: 44.

One or more reaction parameters in a competition reaction, control reaction, or reaction mixture such as order of addition, temperature, reaction duration or time, quantity or identity of reaction components (e.g., mutant Ras, competition probe, test compound), concentration (e.g., concentration of mutant Ras, concentration of competition probe, concentration of test compound), stoichiometry (e.g., ratio of competition probe to mutant Ras, ratio of test compound to mutant Ras, ratio of test compound to competition probe), buffer composition, pH, and reaction site can be adjusted. One or more reaction parameters may be adjusted to affect the extent of reaction (e.g., binding or covalent modification).

A mutant Ras, competition probe, and test compound can be added simultaneously or sequentially in any order to a competition reaction or reaction mixture. A mutant Ras and competition probe can be added simultaneously or sequentially in any order to a competition reaction, control reaction, or reaction mixture. A competition reaction, control reaction, or reaction mixture may include multiple steps, including but not limited to binding, reaction, covalent modification, mixing, heating, cooling, denaturation, and regeneration. Steps in a competition reaction, control reaction, or reaction mixture can comprise any temperature or gradient of temperatures, suitable for achieving the purpose of the given step. Suitable temperatures may include, but are not limited to, room temperature; about 10, 15, 20, 21, 22, 23, 24, 25, 26, 27, 28, 29, 30, 31, 32, 33, 34, 35, 36, 37, 38, 39, and 40° C.; and higher. Steps in a competition reaction, control reaction, or reaction mixture may be of any duration, suitable for achieving the purpose of the given step. Suitable durations may include, but are not limited to, about 1, 5, 10, 15, 20, 25, 30, 35, 40, 45, 50, and 55 seconds; 1, 2, 3, 4, 5, 6, 7, 8, 9, 10, 15, 20, 25, 30, 35, 40, 45, 50, and 55 minutes; and 1, 2, 3, 4, 5, 6, 7, 8, 9, 10, 11, 12, 13, 14, 15, 16, 17, 18, 19, 20, 24, and more hours, including indefinitely until manually interrupted.

In some embodiments, the competition probe is selected in accordance with one or more parameters disclosed herein. In some embodiments, a competition probe may be selected such that in the absence of test compound about or at least about 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% of mutant Ras is bound or covalently modified (e.g., at a substituted amino acid such as a cysteine mutation). In some embodiments, a competition probe may be selected such that in the absence of test compound up to about 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% of mutant Ras is bound or covalently modified (e.g., at a substituted amino acid such as a cysteine mutation). A control reaction, such as a reaction comprising a competition probe and a mutant Ras in the absence of one or more test compounds, can form a baseline for comparing the effects of competition with one or more test compounds. In some embodiments, a competition probe is provided at a concentration of at least about 5 $\mu$M (e.g., 10 $\mu$M, 30 $\mu$M, 100 $\mu$M, or more), and achieves at least about 80% modification (e.g., 85%, 90%, 95%, or higher) in about or fewer than about 10 hours (e.g., 8, 7, 6, 5, 4, 3, 2, or fewer hours) in the absence of a test compound.

In some embodiments, a competition reaction, control reaction, or reaction mixture may comprise one or more mutant Ras proteins. In some embodiments, a competition reaction, control reaction, or reaction mixture may comprise about 1, 2, 3, 4, 5, 10, 15, 25, 50, or more mutant Ras proteins. In some embodiments, a competition reaction, control reaction, or reaction mixture may comprise all Ras mutants with a proteinogenic amino acid mutation at one or more positions, for example, by site saturation mutagenesis. In some embodiments, site saturation mutagenesis is performed at one or more positions selected from position 12, 13, 14, 18, 19, 22, 59, 60, 61, 63, 117, 146, and any combination thereof relative to SEQ ID NO: 1 when optimally aligned, such as from position 12, 13, 18, 61, 146, and any combination thereof. Assays for assessing binding with a plurality of different Ras mutants may be performed in parallel, with each Ras mutant in a separate reaction mixture.

The concentrations of various components of a reaction mixture can be selected for suitability under a given set of conditions. For example, the concentration of a mutant Ras in a competition reaction, control reaction, or reaction mixture can be about or more than about 5 $\mu$M, 10 $\mu$M, 30 $\mu$M, 100 $\mu$M, 200 $\mu$M, 500 $\mu$M, 1 mM or more. The concentration of the mutant Ras may be selected based on the concentration of the competition probe, or vice versa. For example, the mutant Ras may be present at a 1-fold, 2-fold, 3-fold, 4-fold, 5-fold, 10-fold, 25-fold, or more excess relative to the concentration of the competition probe. In some embodiments, the concentration of a competition probe in a competition reaction, control reaction, or reaction mixture is about or more than about 5 $\mu$M, 10 $\mu$M, 30 $\mu$M, 100 $\mu$M, or 200 $\mu$M. In some embodiments, the concentration of a competition probe in a competition reaction, control reaction, or reaction mixture is less than about 5 $\mu$M, 10 $\mu$M, 30 $\mu$M, 100 $\mu$M, or 200 $\mu$M. In some embodiments, the concentration of a test compound in a competition reaction or reaction mixture is about or more than about 5 $\mu$M, 10 $\mu$M, 30 $\mu$M, 100 $\mu$M, or 200 $\mu$M. In some embodiments, the concentration of a test compound in a competition reaction, control reaction, or reaction mixture is less than about 5 $\mu$M, 10 $\mu$M, 30 $\mu$M, 100 $\mu$M, or 200 $\mu$M.

In some embodiments, the competition probe, test compound, or both may be provided in excess quantities relative to the mutant Ras in a competition reaction, control reaction, or reaction mixture. In some embodiments, the mutant Ras may be provided in excess quantities relative to the competition probe, test compound, or both in a competition reaction, control reaction, or reaction mixture. In some embodiments, the ratio of competition probe and/or test compound to mutant Ras in a competition reaction, control reaction, or reaction mixture may be saturating. In some embodiments, the ratio of competition probe and/or test compound to mutant Ras in a competition reaction, control reaction, or reaction mixture may be non-saturating. The ratio can be calculated in terms of concentration, moles, or mass. In some embodiments, the ratio of competition probe and/or test compound to mutant Ras in a competition reaction, control reaction, or reaction mixture may be about or at least about 0.001; 0.002; 0.003; 0.004; 0.005; 0.006; 0.007; 0.008; 0.009; 0.01; 0.02; 0.03; 0.04; 0.05; 0.06; 0.07; 0.08; 0.09; 0.1; 0.2; 0.3; 0.4; 0.5; 0.6; 0.7; 0.8; 0.9; 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; or 1,000. In some embodiments, the ratio of competition probe and/or test compound to mutant Ras in a competition reaction, control reaction, or reaction mixture may be up to about 0.001; 0.002; 0.003; 0.004; 0.005; 0.006; 0.007; 0.008; 0.009; 0.01; 0.02; 0.03; 0.04; 0.05; 0.06; 0.07; 0.08; 0.09; 0.1; 0.2; 0.3; 0.4; 0.5; 0.6; 0.7; 0.8; 0.9; 1.0; 1.1;

1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; or 1,000. In some embodiments, the ratio is between 0.001 to 1000, 0.01 to 100, 0.1 to 50, or 1 to 10.

In some embodiments, the test compound may be provided in excess quantities relative to the competition probe in a competition reaction or reaction mixture, or vice versa. In some embodiments, the ratio of test compound to competition probe in a competition reaction or reaction mixture may be saturating. In some embodiments, the ratio of test compound to competition probe in a competition reaction or reaction mixture may be non-saturating. The ratio may be calculated in terms of concentration, moles, or mass. In some embodiments, the ratio of test compound to competition probe in a competition reaction or reaction mixture may be about or more than about 0.001; 0.002; 0.003; 0.004; 0.005; 0.006; 0.007; 0.008; 0.009; 0.01; 0.02; 0.03; 0.04; 0.05; 0.06; 0.07; 0.08; 0.09; 0.1; 0.2; 0.3; 0.4; 0.5; 0.6; 0.7; 0.8; 0.9; 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; or 1,000. In some embodiments, the ratio of test compound to competition probe in a competition reaction or reaction mixture may be up to about 0.001; 0.002; 0.003; 0.004; 0.005; 0.006; 0.007; 0.008; 0.009; 0.01; 0.02; 0.03; 0.04; 0.05; 0.06; 0.07; 0.08; 0.09; 0.1; 0.2; 0.3; 0.4; 0.5; 0.6; 0.7; 0.8; 0.9; 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; or 1,000. In some embodiments, the ratio is between 0.001 to 1000, 0.01 to 100, 0.1 to 50, or 1 to 10.

A competition reaction, control reaction, or reaction mixture may comprise one or more buffers, non-limiting examples of which include sodium carbonate buffer, sodium bicarbonate buffer, borate buffer, phosphate buffer, Tris buffer, MOPS buffer, HEPES buffer, and any combination thereof. A buffer may optionally comprise sodium chloride, potassium chloride, one or more other salts, and any combination thereof. A competition reaction, control reaction, or reaction mixture may be contained in any suitable reaction site. The reaction site may be a container, such as a well of a multi-well plate, a plate, a tube, a chamber, a flow cell, a chamber or channel of a micro-fluidic device, or a chip. The reaction site may be a partition within a solution, such as a droplet (e.g., within an emersion mixture).

The disclosed assay can be performed in an iterative manner. For example, an initial test compound with a desired binding property to any of the Ras proteins disclosed herein can be used as a competition probe in a subsequent round of screening assay. Where desired, the test compound can be first modified to incorporate a reactive moiety such that it covalently binds to a Ras mutant disclosed herein. Such test compound can serve as a competition probe for screening for other candidates test compounds with, e.g., higher binding affinity to the Ras mutant protein as compared to the initial test compound. This iterative process can allow successive screening for test compounds having improved proved properties including without limitation, higher binding affinity, higher selectivity against a particular Ras protein, or higher on or off rate of binding.

In one aspect, the disclosure provides a mutant Ras comprising a substituted amino acid. Examples of amino acid substitutions in a mutant Ras are provided above. In some embodiments, (a) the substituted amino acid is a reactive amino acid that permits covalent conjugation between the mutant Ras and a competition probe exhibiting the ability to react with the reactive amino acid; and (b) the substituted amino acid is not a cysteine or an aspartic acid at position 12 or 13 relative to SEQ ID NO: 1 or SEQ ID NO: 2 when optimally aligned. In some embodiments, the reactive amino acid is cysteine, lysine, tyrosine, aspartic acid, glutamic acid, or a non-natural amino acid. In some embodiments, the reactive amino acid is cysteine. In some embodiments, the non-natural amino acid comprises a reactive moiety. In some embodiments, the competition probe competes for binding in the Switch II pocket of the mutant Ras. In some embodiments, the substituted amino acid is at a non-conserved position in Ras. In some embodiments, the substituted amino acid is at a position selected from position 62, 64, 65, 69, 74, 76, 79, 80, 81, 82, 83, 84, 85, 86, 87, 88, 91, 92, 93, 94, 95, 96, 97, 98, 99, 100, 101, 106, and any combination thereof relative to SEQ ID NO: 1 or SEQ ID NO: 2 when optimally aligned, such as from position 62, 92, 95, and any combination thereof relative to SEQ ID NO: 1 or SEQ ID NO: 2 when optimally aligned. In some embodiments, the substituted amino acid is a cysteine at position 62, 92, or 95 relative to SEQ ID NO: 1 or SEQ ID NO: 2 when optimally aligned. In some embodiments, the substituted amino acid is a proteinogenic, natural, standard, non-standard, non-canonical, essential, non-essential, or non-natural amino acid. In some embodiments, the substituted amino acid has a positively charged side chain, a negatively charged side chain, a polar uncharged side chain, a non-polar side chain, a hydrophobic side chain, a hydrophilic side chain, an aliphatic side chain, an aromatic side chain, a cyclic side chain, an acyclic side chain, a basic side chain, or an acidic side chain. In some embodiments, the substituted amino acid has a nucleophilic or electrophilic side chain.

In some embodiments, (a) the substituted amino acid is a reactive amino acid that permits covalent conjugation between the mutant Ras and a competition probe exhibiting the ability to react with the reactive amino acid; (b) the substituted amino acid is a cysteine or an aspartic acid at position 12 or 13 relative to SEQ ID NO: 1 when optimally aligned; and (c) the mutant Ras is selected from the group consisting of mutant MRAS, mutant ERAS, mutant RRAS2, mutant RALA, mutant RALB, mutant RIT1, and any combination thereof. In some embodiments, the reactive amino acid is cysteine. In some embodiments, the competition probe is capable of binding the mutant Ras. In some embodiments, the competition probe competes for binding in the Switch II pocket of the mutant Ras. In some embodiments, the mutant Ras is selected from the group consisting of RALA, RALB, and any combination thereof.

In some embodiments, a mutant Ras may comprise one or more additional mutations, including any one or more of the Ras mutations described herein. In some embodiments, one or more additional mutations in a mutant Ras may be at a position selected from position 12, 13, 14, 18, 19, 22, 59, 60, 61, 63, 117, 146, and any combination thereof relative to SEQ ID NO: 1 or SEQ ID NO: 2 when optimally aligned, such as from position 12, 13, 18, 61, 146, and any combination thereof relative to SEQ ID NO: 1 or SEQ ID NO: 2 when optimally aligned. In some embodiments, one or more additional mutations in a mutant Ras may be selected from G12A, G12C, G12D, G12F, G12L, G12R, G12S, G12V, G13A, G13C, G13D, G13R, G13S, G13V, V14G, V14I, A18D, A18T, L19F, Q22K, A59T, G60E, Q61E, Q61H, Q61K, Q61L, Q61P, Q61R, E63K, K117N, A146P, A146T, A146V, and any combination thereof, such as from G12A, G12C, G12D, G12R, G12S, G12V, G13C, G13D, G13R, G13S, G13V, A18D, Q61H, Q61K, Q61L, Q61R, K117N, A146T, and any combination thereof relative to SEQ ID NO: 1 or SEQ ID NO: 2 when optimally aligned. In some embodiments, a mutant RAS is selected from a mutant KRAS, mutant HRAS, mutant NRAS, mutant RALA, mutant RALB, and any combination thereof.

In some embodiments, a mutant RAS is a mutant KRAS. In some embodiments, one or more additional mutations in a mutant KRAS may be selected from G12D, G12V, G13D, G12C, G12A, G12S, G12R, G13C, Q61H, A146T, Q61H, Q61L, Q61R, Q61H, G13S, G12G13R, G12F, Q61K, G13D, A146V, G13A, G13V, G12D, A146T, G13D, A59T, V14I, Q22K, G12F, K117N, Q61P, L19F, K117N, G12C, L19F, Q61E, G12L, G12V, G13G, Q61K, V14G, Q61L, A18D, G12G, E63K, A146P, A146V, G13G, G10_A11insG, G12V, L19F, G13V, G121, G60G, G12N, D173D, G12A, T58I, G12_G13insG, A59E, A59G, K5E, G12G, G60D, L23R, Q22Q, G12Y, A11V, G12 W, G15S, G13_V14insG, A11_G12insGA, G10R, A66_M67insEEYSA, G13G, G13C, G12E, Q22R, D33E, V8V, P34L, V9I, G12S, G13E, S17G, D57I, M72V, G60G, Y64N, I24N, E31K, G13E, G13F, T35A, G13N, G10E, A11P, A18V, D92Y, A59T, G15D, Q61R, D69G, G12D, Y64H, T20T, G10G, K5R, K147N, L23L, R164Q, T20M, D154delD, G10G, G10_A11insG, S136N, M72T, G13N, T20T, E3fs*3, G12G, S17N, K88N, P140S, G12L, R161*, E31Q, Q61D, K117E, G12fs*3, R102fs*2, V7E, G60R, Q70P, H27N, T20S, C185S, E62K, G138R, G60A, I24V, V14L, E62D, R164R, S65I, Q61K, P34S, K5N, G13Y, H95L, I21R, N86K, G12 W, D92G, D69fs*4, M72I, V14A, G15G, E63K, G15G, A18T, Q22*, T74T, G13R, M67L, G138E, C185R, P121H, L19_T20>FA, G12 G13insG, I36M, E63E, R68G, K117R, E63del, T35T, T20A, G12C, L6F, A59A, C80S, H27L, G77A, M72_R73ins15, Q61R, P121S, C118S, G13M, F156L, I36L, E49*, D30E, T58T, G12V, D33E, A134T, G13R, C51C, T58_A59insVA, D33E, G12E, K117N, K88*, R164R, G12V9F, R97I, G13P, G13C, A146A, E62_S65>D, A59A, K16_S17insW, A11T, A11A, Q61E, V9 G10insV, K5N, R68S, V8A, G60V, G15G, F28S, A146G, R73M, T127I, M188L, E98*, S65_A66ins15, A59del, T74P, T183_K184delTK, T74T, D153V, G13E, V7M, G12L, Y64D, E91K, G60V, G13 V14>DI, H27H, I24F, C80Y, K16R, H27N, G60fs*27, E37K, D153N, E62G, E49K, P110S, Y71C, L52F, V45V, V14_G15insG, G12N, G12_G13insAG, A59S, G12R, T58I, G13V, R68M, G12T, K117R, V9V, L23I, R135T, T20R, A130V, R68S, G13I, G12_G13insA, R164L, E49K, and any combination thereof relative to SEQ ID NO: 1 or SEQ ID NO: 2 when optimally aligned; such as from G12D, G12V, G13D, G12C, G12A, G12S, G12R, G13C, Q61H, A146T, Q61L, Q61R, G13S, G13R, G12F, Q61K, G13A, A146V, G13V, A59T, V14I, Q22K, Q61P, L19F, K117N, G12L, Q61E, V14G, A146P, E63K, A18D, and any combination thereof; such as from G12A, G12C, G12D, G12R, G12S, G12V, G13C, G13D, G13R, G13S, A18D, Q61H, Q61L, Q61R, A146T, K117N, and any combination thereof. In some embodiments, the mutant KRAS is a mutant KRAS isoform a or a mutant KRAS isoform b.

In some embodiments, the disclosure provides a KRAS double mutant based on SEQ ID NO: 1, in which positions 12 and 92 are substituted as G12D and D92C. In some embodiments, the subject method utilizes a KRAS double mutant based on SEQ ID NO: 1, in which positions 12 and 95 are substituted as G12D and H95C. In some embodiments, the disclosure provides a KRAS mutant having a sequence shown in SEQ ID NO: 17, SEQ ID NO: 19, SEQ ID NO: 21, SEQ ID NO: 36, SEQ ID NO: 37, or SEQ ID NO: 38. In some embodiments, the disclosure provides a KRAS double mutant based on SEQ ID NO: 2, in which positions 12 and 92 are substituted as G12D and D92C. In some embodiments, the disclosure provides a KRAS double mutant based on SEQ ID NO: 2, in which positions 12 and 95 are substituted as G12D and H95C. In some embodiments, the disclosure provides a KRAS mutant having a sequence shown in SEQ ID NO: 30, SEQ ID NO: 31, SEQ ID NO: 32, SEQ ID NO: 42, SEQ ID NO: 43 or SEQ ID NO: 44.

In some embodiments, a mutant RAS is a mutant HRAS. In some embodiments, one or more additional mutations in a mutant HRAS may be selected from G13R, G12V, Q61R, Q61L, Q61K, G12S, G12D, H27H, G12C, G13V, G13D, Q61G13S, Q61H, G12R, Q61R, G12A, G13C, Q61H, Y4H, E62G, Q61K, Y4fs*2, A59T, Q61P, Q61H, Q61L, V81M, K117N, K117N, A11S, A11A, G13I, A18V, Q61R, Q61R, M72I, R123H, P179L, E3fs*17, G10_A11insG, G12N, G12_G13insAG, G12G12T, G13G, V14G, V14V, G15S, G15D, S17G, A18T, A18A, T20I, Q22*, Q25L, Y32*, Y32Y, G48R, T58I, A59A, G60S, Q61E, Q61R, Q61L, Q61Q, A66T, M72I, T74T, F78F, A83D, A83V, E91K, D92N, R102L, D108Y, P110P, K117E, D119N, D119H, D119D, L120V, R128L, A130T, L133R, A134S, R135*, R135Q, I139I, E143K, R149fs*23, L188F, and any combination thereof relative to SEQ ID NO: 3 when optimally aligned; such as from G13R, G12V, Q61R, Q61L, Q61K, G12S, G12D, G12C, G13V, G13S, Q61H, G13D, G12R, G12A, G13C, and any combination thereof.

In some embodiments, a mutant RAS is a mutant NRAS. In some embodiments, one or more additional mutations in a mutant NRAS is selected from Q61R, Q61K, G12D, G13D, Q61L, G12S, Q61R, G12C, G13R, Q61K, G12V, Q61H, G12A, G13V, Q61H, Q61H, Q61L, G13C, G12R, Q61P, G13A, G13S, A18T, Q61E, G60E, Q61Q, A59T, R68T, G12D, A146T, Q61R, G13G, E62Q, A59D, G13D, A11T, G10E, Q61L, Q61L, D92N, G12C, G75G, 565C, G12V, E62fs*6, T58T, Q61K, Q22K, D154G, G12N, Y64N, A146T, A59A, T58I, P185S, G12S, E132K, T50I, G10G, Q61R, G12G, G12G, G12P, H131R, Y4C, T20I, L19L, Q43*, K16N, S87C, P140P, T58I, S87fs*17, V112L, S65R, R97G, Q61K, T58A, G138R, T74S, Q61S, G60E, G15R, A59fs*4, M72I, G12E, 565G, D175N, I100T, A18A, E162*, A130D, G15E, D33E, G13V, G13N, G12T, VBA, A146P, G12Y, E49K, Y40*, K16Q, T20T, Y71C, G13Y, S87N, V45A, E153A, R167*, A66T, Q61T, G60V, C51Y, R68R, A59G, R164C, E49E, 565S, A146V, L79F, Y64D, G13V, A91V, E63K, E62K, I55fs*17, I84T, E63*, Q61_E62>HK, G10*, L79I, P185A, A59T, L79_C80insQYMTGEGF, V29V, T148S, R68G, D33H, A18A, P34L, M72I, P34L, E49*, Q61P, G60R, 5106L, L171L, T20T, Q61E, I24L, Y32*, S17N, D57A, Q61*, D54G, C80Y, and any combination thereof relative to SEQ ID NO: 4 when optimally aligned; such as from Q61R, Q61K, G12D, Q61L, G13D, G12S, G12C, G13R, G12V, Q61H, G13V, G12A, G13C, G12R, Q61P, G13A, A18T, G13S, Q61E, G60E, and any combination thereof.

In some embodiments, a mutant RAS is a mutant MRAS. In some embodiments, one or more additional mutations in a mutant MRAS is selected from E154*, V94I, P120P, P151L, E47G, M1_A2>IS, V113I, L133F, V6I, T137S, 1901, L16L, R138K, D165N, E143Q, A28T, R138S, I90M, Q140K, D129N, R173T, P120L, I136S, T54M, N149S, A145A, L171L, R112C, L29F, R138M, D195D, D129G, R78Q, A2V, R105H, D64D, G141R, D9N, S99S, V164V, and any combination thereof relative to SEQ ID NO: 5 when optimally aligned.

In some embodiments, a mutant RAS is a mutant ERAS. In some embodiments, one or more additional mutations in a mutant ERAS is selected from F177F, R185 W, A97T, G174R, S193S, G48S, D71N, P140S, G139V, L194L, V149M, V119I, S181L, V52M, C226*, F120L, V188M, A97V, R103R, R31C, R32H, D69N, L117L, K6T, A165A, L61V, H70H, D69D, E24*, R103I, H171L, R27R, E24K, 1129I, E41D, H227Q, A165S, I59S, and any combination thereof relative to SEQ ID NO: 6 when optimally aligned.

In some embodiments, a mutant RAS is a mutant RRAS2. In some embodiments, one or more additional mutations in a mutant RRAS2 is selected from A70T, Q72L, V202A, V202V, Q72H, A167T, Q134Q, G24D, R147Q, S186fs*>16, D8N, Y82*, F204L, G24G, A29A, A158V, R117C, R63Q, Q72H, G24V, A158T, R63R, A167A, D44E, K53M, K177T, D49Y, K159Q, and any combination thereof relative to SEQ ID NO: 7 when optimally aligned. In some embodiments, the mutant RRAS2 is a mutant RRAS2 isoform a, a mutant RRAS2 isoform b, or a mutant RRAS2 isoform c.

In some embodiments, a mutant RAS is a mutant RALA. In some embodiments, one or more additional mutations in a mutant RALA is selected from R176*, V20A, G23D, A158S, G23S, N81S, D42N, G59 W, V25E, G88 W, I18I, F168C, N10K, E174*, R84*, E116D, K193*, R108M, D49G, Q63*, Q63H, L14F, Q63R, S11Y, G21A, R176R, R198I, Q110H, K7E, Y82C, L112V, E141K, A177A, V154M, L32Q, 164I, Q63Q, E147*, G59R, R84Q, K134E, and any combination thereof relative to SEQ ID NO: 8 when optimally aligned.

In some embodiments, a mutant RAS is a mutant RALB. In some embodiments, one or more additional mutations in a mutant RALB is selected from E106K, G23V, R144S, M19K, V125V, K129N, K194K, S85R, E141K, T69T, S94L, G24C, P122S, I18T, Q110H, S22S, K196N, L112I, R79*, K197R, E60*, T31T, R84 W, K200I, I111T, P45P, K180K, G71R, E175K, M19T, R135Q, S100S, F169L, R79Q, M19I, V125F, R52G, L124L, G23R, R136S, N188S, G23E, T161T, I111N, E106E, R162 W, G23A, and any combination thereof relative to SEQ ID NO: 9 when optimally aligned.

In some embodiments, a mutant RAS is a mutant RIT1. In some embodiments, one or more additional mutations in a mutant RIT1 is selected from M90I, F211L, A57G, D51V, R168H, D173N, R122*, R112C, M90I, A153V, R122L, R183H, K34T, F161fs*47, Q40L, A192T, G133E, V174V, L138L, L71V, R122Q, R45Q, A166delA, S19L, I73S, D216Y, E81Q, M90I, L74M, D56Y, K196fs*12, S10delS, R86 W, F82C, T38A, A77P, F41F, R63R, K23E, F108L, D172N, R120*, R212R, T124T, A77S, F82L, D87N, D172E, K34N, P199P, and any combination thereof relative to SEQ ID NO: 10 when optimally aligned. In some embodiments, the mutant RIT1 is a mutant RIT1 isoform 1, a mutant RIT1 isoform 2, or a mutant RIT1 isoform 3.

In one aspect, the disclosure provides a polynucleotide encoding any mutant Ras described herein. In some embodiments, the polynucleotide comprises DNA or RNA. In some embodiments, the polynucleotide encodes a mutant Ras selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, and any combination thereof. A polynucleotide described herein can be obtained using chemical synthesis, molecular cloning or recombinant methods, DNA or gene assembly methods, artificial gene synthesis, PCR, or any combination thereof. Methods of chemical polynucleotide synthesis are well known in the art and need not be described in detail herein. One of skill in the art can use the sequences provided herein and a commercial DNA synthesizer to produce a desired DNA sequence. For preparing polynucleotides using recombinant methods, a polynucleotide comprising a desired sequence can be inserted into a suitable cloning or expression vector, and the cloning or expression vector in turn can be introduced into a suitable host cell for replication and amplification, as further discussed herein. Polynucleotides may be inserted into host cells by any means known in the art. Cells may be transformed by introducing an exogenous polynucleotide, for example, by direct uptake, endocytosis, transfection, F-mating, chemical transformation, or electroporation. Once introduced, the exogenous polynucleotide can be maintained within the cell as a non-integrated expression vector (such as a plasmid) or integrated into the host cell genome. The polynucleotide so amplified can be isolated from the host cell by methods well known within the art. Alternatively, nucleic acid amplification methods (e.g., PCR) allow reproduction of DNA sequences.

RNA can be obtained by using the isolated DNA in an appropriate expression vector and inserting it into a suitable host cell. When the cell replicates and the DNA is transcribed into RNA, the RNA can then be isolated using methods well known to those of skill in the art. Alternatively, RNA can be obtained by transcribing the isolated DNA, for example, by an in vitro transcription reaction using an RNA polymerase. Alternatively, RNA can be obtained using chemical synthesis.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the expression vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

In one aspect, the disclosure provides an expression vector comprising any of the polynucleotides described herein. A polynucleotide may be located in an expression vector. An expression vector may be a construct, which is capable of delivering, and preferably expressing, one or more gene(s) or sequence(s) of interest in a host cell. Examples of expression vectors include, but are not limited to, viral vectors (e.g., adenoviruses, adeno-associated viruses, and retroviruses), naked DNA or RNA expression vectors, plasmids, cosmids, phage vectors, DNA or RNA expression vectors associated with cationic condensing agents, DNA or RNA expression vectors encapsulated in liposomes, and certain eukaryotic cells, such as producer cells. An expression vector may allow easy and efficient replication, cloning, and/or selection. Accordingly, an expression vector may additionally include nucleic acid sequences that permit it to replicate in the host cell, such as an origin of replication, one or more therapeutic genes and/or selectable marker genes and other genetic elements known in the art such as regulatory elements directing transcription, translation and/or secretion of the encoded protein. Expression vector components may generally include, but are not limited to, one or more of the following: a signal sequence; an origin of replication; one or more marker genes; and suitable transcriptional controlling elements (such as promoters, enhancers and terminator). For expression (e.g., translation), one or more translational controlling elements are also usually required, such as ribosome binding sites, translation initiation sites, internal ribosome entry site, and stop codons. The expression vector may be used to transduce, transform or infect a cell, thereby causing the cell to express nucleic acids and/or proteins other than those native to the cell. The expression vector optionally includes materials to aid in achieving entry of the nucleic acid into the cell, such as a viral particle, liposome, protein coating or the like. Numerous types of appropriate expression vectors are known in the art for protein expression, by standard molecular biology techniques. Such expression vectors are selected from among conventional vector types including insects, e.g., baculovirus expression, or yeast, fungal, bacterial or viral expression systems. Other appropriate expression vectors, of which numerous types are known in the art, can also be used for this purpose. Methods for obtaining cloning and expression vectors are well-known (see, e.g., Green and Sambrook, Molecular Cloning: A Laboratory Manual, 4th edition, Cold Spring Harbor Laboratory Press, New York (2012)).

In one aspect, the disclosure provides a host cell comprising any of the polynucleotides described herein. In one aspect, the disclosure provides a host cell comprising any of the expression vectors described herein. Any host cell capable of expressing heterologous DNA can be used for the purpose of isolating a Ras or mutant Ras protein or the polynucleotides encoding a Ras or mutant Ras protein. Suitable host cells include, but are not limited to, mammalian (e.g., human, such as HEK or HeLa; mouse, such as a 3T3 or cells derived from Swiss, BALB/c or NIH mice; hamster, such as CHO; monkey, such as COS), bacterial (e.g., *Escherichia coli*, *Bacillus subtilis*, *Pseudomonas*, *Streptomyces*), fungal (e.g., *Saccharomyces cerevisiae*, *Schizosaccharomyces pombe*, *Kluyveromyces lactis*), or insect (e.g., *Drosophila melanogaster*, High Five, *Spodoptera frugipedera* Sf9) host cells. The expression vectors containing the polynucleotides of interest can be introduced into a host cell by any of a number of appropriate means, including electroporation, chemical transformation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell. The transfected or transformed host cell may then be cultured under conditions that allow expression of the protein. In some embodiments, a mutant Ras is purified from a host cell.

In some embodiments, a mutant Ras is produced using in vitro or cell-free protein synthesis, for example using a cell-free translation system comprising a cell extract such as *Escherichia coli* cell extract, rabbit reticulocyte cell extract, wheat germ cell extract, or insect cell extract. The expressed protein may be recovered, isolated, and/or optionally purified from the cell, cell extract, or from the culture medium, by appropriate means known to one of skill in the art. For example, the proteins are isolated in soluble form following cell lysis, or extracted using known techniques, e.g., in guanidine chloride. The proteins may be further purified using any of a variety of conventional methods including, but not limited to: liquid chromatography such as normal or reversed phase, using HPLC, FPLC and the like; affinity chromatography such as with inorganic ligands or monoclonal antibodies; size exclusion chromatography; immobilized metal chelate chromatography; gel electrophoresis; and the like. One of skill in the art may select the most appropriate isolation and purification techniques. Still other suitable host cells, as well as methods for transfection, culture, amplification, screening, production, and purification are known in the art.

In one aspect, the disclosure provides a kit for performing any of the methods described herein. In some embodiments, the kit is for selecting a Ras antagonist. In some embodiments, the kit comprises a mutant Ras. In some embodiments, the mutant Ras is any of the mutant Ras proteins described herein. In some embodiments, the mutant Ras has a cysteine mutation at a position other than position 12 or 13 relative to SEQ ID NO: 1 or SEQ ID NO: 2 when optimally aligned. In some embodiments, the kit comprises a KRAS double mutant based on SEQ ID NO: 1, in which positions 12 and 92 are substituted as G12D and D92C. In some embodiments, the kit comprises a KRAS double mutant based on SEQ ID NO: 1, in which positions 12 and 95 are substituted as G12D and H95C. In some embodiments, the kit comprises a KRAS mutant having a sequence shown in SEQ ID NO: 17, SEQ ID NO: 19, SEQ ID NO: 21, SEQ ID NO: 36, SEQ ID NO: 37, or SEQ ID NO: 38. In some embodiments, the kit comprises a KRAS double mutant based on SEQ ID NO: 2, in which positions 12 and 92 are substituted as G12D and D92C. In some embodiments, the kit comprises a KRAS double mutant based on SEQ ID NO: 2, in which positions 12 and 95 are substituted as G12D and H95C. In some embodiments, the kit comprises a KRAS mutant having a sequence shown in SEQ ID NO: 30, SEQ ID NO: 31, SEQ ID NO: 32, SEQ ID NO: 42, SEQ ID NO: 43 or SEQ ID NO: 44.

In some embodiments, the kit comprises instructions for using the mutant Ras in a competition reaction between a competition probe and a test compound. In some embodiments, the kit further comprises the competition probe. In some embodiments, the kit further comprises one or more test compounds. Kits can comprise one or more elements disclosed herein in relation to any of the various aspects, in any combination. Reagents and other materials in a kit may be contained in any suitable container, and may be in an immediately usable form or require combination with other reagents in the kit or reagents supplied by a user (e.g., dilution of a concentrated composition or reconstitution of a lyophilized composition). A kit may provide one or more buffers, non-limiting examples of which include sodium carbonate buffer, sodium bicarbonate buffer, borate buffer, phosphate buffer, Tris buffer, MOPS buffer, HEPES buffer, and any combination thereof. A kit may comprise a control sample, e.g., for use as a positive control, negative control, or quantification standard. In some embodiments, the kit comprises instructions for use of the kit in accordance with one or more methods disclosed herein. In some embodiments, a method for using the kit comprises combining in a reaction mixture or a competition reaction a mutant Ras, a competition probe, and a test compound and detecting a decrease in binding between the mutant Ras and the competition probe as compared to binding of the mutant Ras in the absence of the test compound.

In one aspect, the disclosure provides a substrate having attached thereto a complex comprising a mutant Ras and a competition probe. The mutant Ras can be any of the mutant Ras proteins described herein. In some embodiments, the mutant Ras comprises a substituted amino acid that is a reactive amino acid that permits covalent conjugation between the mutant Ras and the competition probe. In some embodiments, the substituted amino acid is not a cysteine or an aspartic acid at position 12 or 13 relative to SEQ ID NO: 1 or SEQ ID NO: 2 when optimally aligned. In some embodiments, the competition probe is covalently bound to the mutant Ras at the reactive amino acid. In some embodiments, the reactive amino acid comprises a reactive moiety. In some embodiments, the competition probe binds in the Switch II pocket of the mutant Ras. In some embodiments, the substituted amino acid is at a non-conserved position in Ras. In some embodiments, the substituted amino acid is at position 62, 92, or 95 relative to SEQ ID NO: 1 or SEQ ID NO: 2 when optimally aligned. In some embodiments, the substituted amino acid is a cysteine at position 62, 92, or 95 relative to SEQ ID NO: 1 or SEQ ID NO: 2 when optimally aligned. In some embodiments, the mutant Ras may comprise one or more additional mutations. In some embodiments, the substrate comprises a KRAS double mutant based on SEQ ID NO: 1, in which positions 12 and 92 are substituted as G12D and D92C. In some embodiments, the substrate comprises a KRAS double mutant based on SEQ ID NO: 1, in which positions 12 and 95 are substituted as G12D and H95C. In some embodiments, the substrate comprises a KRAS mutant having a sequence shown in SEQ ID NO: 17, SEQ ID NO: 19, SEQ ID NO: 21, SEQ ID NO: 36, SEQ ID NO: 37, or SEQ ID NO: 38. In some embodiments, the substrate comprises a KRAS double mutant based on SEQ ID NO: 2, in which positions 12 and 92 are substituted as G12D and D92C. In some embodiments, the substrate comprises a KRAS double mutant based on SEQ ID NO: 2, in which positions 12 and 95 are substituted as G12D and H95C. In some embodiments, the substrate comprises a KRAS mutant having a sequence shown in SEQ ID NO: 30, SEQ ID NO: 31, SEQ ID NO: 32, SEQ ID NO: 42, SEQ ID NO: 43 or SEQ ID NO: 44

The substrate can take any of a variety of forms. In some embodiments, the substrate is in a form selected from the group consisting of beads, microparticles, nanoparticles, nanocrystals, fibers, microfibers, nanofibers, nanowires, nanotubes, mats, planar sheets, planar wafers or slides, multi-well plates, optical slides, flow cells, channels, and any combination thereof. A substrate may further include one or more additional structures, capillaries, wells, flow cells, channels (e.g., microfluidic channels), and the like. A variety of suitable substrate materials are available. Examples of substrate materials include, but are not limited to, inorganic materials such as silica based substrates (e.g., glass, quartz, fused silica, silicon, or the like), metals (e.g., gold), ceramics, or titanium dioxide; semiconductor materials; composite materials; organic materials such as polymer or plastic materials (e.g., poly(methyl methacrylate), polyethylene, polypropylene, polystyrene, cellulose, agarose, dextran, polyvinyl chloride, nylons, polyesters, polycarbonates, cyclic olefin polymers, natural polymer, synthetic polymer, or any of a variety of organic substrate materials conventionally used as supports for reactive media); and any combinations thereof. In some embodiments, the substrate comprises a material selected from the group consisting of glass, quartz, fused silica, silicon, metal, polymers, plastics, ceramics, composite materials, and any combination thereof.

When referring to immobilization or attachment of molecules (e.g., competition probe, a mutant Ras) to a substrate, the terms "immobilized" and "attached" are used interchangeably herein, and both terms are intended to encompass direct, indirect, covalent, or non-covalent attachment, unless indicated otherwise. In some embodiments, covalent attachment may be preferred. In general, the molecules (e.g., competition probe, a mutant Ras) remain immobilized or attached to the substrate under the conditions in which it is intended to use the substrate, for example in applications for detecting binding between a competition probe and a mutant Ras.

In some embodiments, a substrate material comprises a material that is reactive, such that under specified conditions, a molecule (e.g., competition probe, a mutant Ras) can be attached directly to the surface of the substrate. In some embodiments, a substrate material comprises an inert substrate or matrix (e.g., glass slides, gold surface, polymer beads, or other substrate material) that has been "functionalized", for example by application of a layer or coating of an intermediate material comprising a reactive moiety which permit attachment (e.g., covalent attachment) to molecules, such as proteins or small molecules. Examples of such substrates include, but are not limited to, carboxymethylated dextran supported on an inert substrate such as gold. In such embodiments, the molecules (e.g., competition probe, a mutant Ras) may be directly covalently attached to the intermediate material (e.g., the dextran) but the intermediate material may itself be non-covalently attached to the substrate or matrix (e.g., the gold substrate).

In some embodiments, the complex is attached to the substrate by the mutant Ras. In some embodiments, the complex is attached to the substrate by the competition probe. Attachment may be effected by means of a reactive moiety. In some embodiments, a molecule (e.g., competition probe, a mutant Ras) to be attached to the substrate comprises a reactive moiety. In some embodiments, a substrate to which molecules are attached comprises a reactive moiety.

In one aspect, the disclosure provides systems for performing any of the methods described herein. In some embodiments, the disclosure provides a system for selecting a Ras antagonist. In some embodiments, the system comprises a computer configured to receive a user request to perform a competition reaction. In some embodiments, the system comprises a reaction module that prepares the competition reaction, the competition reaction comprising a mutant Ras, a competition probe that is capable of binding the mutant Ras, and a test compound. In some embodiments, the system comprises a detection module that detects a decrease in binding between the mutant Ras and the competition probe as compared to binding of the mutant Ras in the absence of the test compound. In some embodiments, the mutant Ras is any of the mutant Ras proteins described herein. In some embodiments, the mutant Ras comprises a cysteine mutation that is not at position 12 or 13 relative to SEQ ID NO: 1 or SEQ ID NO: 2 when optimally aligned. In some embodiments, the competition probe is capable of covalently modifying the mutant Ras at the cysteine mutation. In some embodiments, the test compound inhibits covalent modification of the mutant Ras by the competition probe.

In some embodiments, one or more steps in sample processing, preparing the competition reaction, performing the competition reaction, detecting binding, and/or analysis are automated by the system. In some embodiments, automation may comprise the use of one or more liquid handlers and associated software. Several commercially available liquid handling systems can be utilized to run the automation of such processes (see, for example, liquid handlers from PerkinElmer, Caliper Life Sciences, Tecan, Eppendorf, Apricot Design, and Agilent Automation Solutions). In some embodiments, detecting comprises a real-time detection instrument.

The various steps may be implemented as various blocks, operations, tools, modules or techniques which, in turn, may be implemented in hardware, firmware, software, or any combination thereof. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc. In some embodiments, the computer is configured to receive a user request to perform a competition reaction on a test compound. The computer may receive the user request directly (e.g., by way of an input device such as a keyboard, mouse, or touch screen operated by the user) or indirectly (e.g., through a wired or wireless connection, including over the internet). Non-limiting examples of users include an individual, medical personnel, clinicians, laboratory personnel, insurance company personnel, a health care provider, a health care manager, others in the health care industry, or electronic system (e.g., one or more computers, and/or one or more servers).

A computer can comprise one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other storage medium. Likewise, this software may be delivered to a computing device via any known delivery method including, for example, over a communication channel such as a telephone line, the internet, a wireless connection, etc., or via a transportable medium, such as a computer readable disk, flash drive, etc.

The computer system may be understood as a logical apparatus that can read instructions from media (e.g., software) and/or network port (e.g., from the internet), which can optionally be connected to a server having fixed media. A computer system may comprise one or more of a CPU, disk drives, input devices such as keyboard and/or mouse, and a display (e.g., a monitor). Data communication, such as transmission of instructions or reports, can be achieved through a communication medium to a server at a local or a remote location. The communication medium can include any means of transmitting and/or receiving data. For example, the communication medium can be a network connection, a wireless connection, or an internet connection. Such a connection can provide for communication over the World Wide Web.

A system can comprise one or more detection modules for performing one or more of mass spectrometry, enzyme-linked immunosorbent assay (ELISA), surface plasmon resonance, solid phase extraction, liquid chromatography, or any combination thereof. In some embodiments, the detection module may detect binding, covalent modification, mass-to-charge ratio, gas-phase ions, absorbance, fluorescence, luminescence, color, an electrochemical signal, current, or any combination thereof.

In some embodiments, the system comprises a report generator that sends a report to a recipient. In some embodiments, the report contains results from the detection module. In some embodiments, the report generator identifies one or more test compounds as an inhibitor of Ras. In some embodiments, the report generator identifies one or more test compounds as not an inhibitor of Ras. The report generator may send a report automatically in response to production of data (e.g., binding, fragmentation, or fluorescence intensity) by the system, such as in the form of data analysis performed by mass spectrometry or surface plasmon resonance analysis software. Alternatively, the report generator may send a report in response to instructions from a user.

Results of methods described herein will typically be assembled in a report. A report may contain raw signal intensity data, processed signal intensity data (e.g., graphical displays, calculation of binding affinity), a conclusion that one or more test compounds is a Ras antagonist, a conclusion that one or more test compounds is not a Ras antagonist, and/or quantification of a concentration, binding affinity, or degree of covalent modification. In some embodiments, the report comprises test compounds identified as antagonists of Ras and excludes test compounds not identified as antagonists of Ras. In some embodiments, the report comprises test compounds identified as antagonists of Ras and test compounds not identified as antagonists of Ras.

The software routines used to generate the report can be run on a computer. The report can be generated automatically upon receiving data. The report can be generated in response to a user request. The report may also be stored in any suitable medium, such as in RAM, ROM, flash memory, a magnetic disk, a laser disk, or other storage medium. The report may be delivered to a computing device via any known delivery method including, for example, over a communication channel such as a telephone line, the internet, a wireless connection, etc., or via a transportable medium, such as a computer readable disk, flash drive, etc. The report may be transmitted to a recipient at a local or remote location using any suitable communication medium. For example, the communication medium can be a network connection, a wireless connection, or an internet connection. A report can be transmitted over such networks or connections (or any other suitable means for transmitting information, including but not limited to mailing a physical report, such as a print-out) for reception and/or for review by a recipient. The recipient can be, but is not limited to, the user, an individual, medical personnel, clinicians, laboratory personnel, insurance company personnel, a health care provider, a health care manager, others in the health care industry, or electronic system (e.g., one or more computers, and/or one or more servers). In some embodiments, the report generator sends the report to a recipient's device, such as a personal computer, phone, tablet, or other device. The report may be viewed online, saved on the recipient's device, or printed.

In one aspect, the disclosure provides a computer readable medium comprising codes that, upon execution by one or more processors, implements a method according to any of the methods disclosed herein. In some embodiments, execution of the computer readable medium implements a method of selecting a Ras antagonist. In one embodiment, execution of the computer readable medium implements a method of selecting a Ras antagonist, the method comprising: responsive to a user request to perform a competition reaction on a test compound, performing a competition reaction on the test compound in response to the user request, wherein the competition reaction comprises a mutant Ras, a competition probe that is capable of binding the mutant Ras, and a test compound; detecting a decrease in binding between the mutant Ras and the competition probe as compared to binding of the mutant Ras in the absence of the test compound; and generating a report that contains results for detection of a decrease in binding. Examples of competition probes, mutant Ras, and parameters for performing competition reactions are provided above. In some embodiments, the report generator identifies the test compound as an inhibitor of Ras.

Computer readable medium may take many forms, including but not limited to, a tangible storage medium, a carrier wave medium, or physical transmission medium. Non-volatile storage media include, for example, optical or magnetic disks, such as any of the storage devices in any computer(s) or the like, such as may be used to implement the calculation steps, processing steps, etc. Volatile storage media include dynamic memory, such as main memory of a computer. Tangible transmission media include coaxial cables; copper wire and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

EXAMPLES

Example 1: Recombinant Protein Expression of RalA WT and RalA G23C

Hexahistidine-tagged recombinant human RalA ("hexahistidine" disclosed as SEQ ID NO: 49) (residues 11-183, either WT or G23C) was transformed into *Escherichia coli* (BL21 (DE)). After the bacterial grew to an OD(600) of 0.4-0.6 in Terrific Broth containing 30 mg/L kanamycin at 37° C., induction was carried out at 18° C. using 0.5 mM IPTG and growth was continued at 18° C. for about 18 h. The bacteria were harvested by centrifugation and the obtained pellet was either stored at −80° C. or used freshly for the subsequent steps.

The pellet was resuspended in bacterial protein extraction reagent (B-Per, Fisher Scientific) containing protease inhibitor cocktail (Pierce Protease Inhibitor tablets, EDTA free). The lysis reaction was clarified by ultracentrifugation, and additional lysis buffer (500 mM NaCl, 20 mM TRIS pH=8, 5 mM imidazole) was added along with 2 mM BME (final). The supernatant was incubated for 1 h with Co-affinity beads (Pierce HisPur resin, ~2 mL bed volume per 1 L initial culture) at 4° C. The loaded beads were then washed with lysis buffer containing 2 mM BME, and the protein was eluted with buffer containing 250 mM imidazole.

The crude protein was dialyzed against a buffer containing 300 mM NaCl, 20 mM TRIS pH=8, 1 mM DTT, 1 mM EDTA with a three-fold excess of GDP. After concentrating the protein to about 30 mg/mL (Amicon-15, 10000 molecular weight cut-off) and addition of 10 mM $MgCl_2$ (final), it was purified by gel-filtration using a Superdex 75 column (GE, Hiload 16/60) with the following buffer: 20 mM HEPES pH=7.5, 150 mM NaCl, 1 mM DTT and 1 mM $MgCl_2$. The freshly prepared and purified protein was then concentrated to ~20 mg/mL and flash frozen in liquid nitrogen for later use in assays.

For X-ray crystallography, the crude protein obtained from Co-bead elution was cleaved using hexahistidine-tagged TEV-protease ("hexahistidine" disclosed as SEQ ID NO: 49) (1 mg recombinant TEV per 25 mg crude RalA G23C, 1 mg GDP added per 20 mg crude RalA) while dialyzing against a buffer containing 300 mM NaCl, 20 mM TRIS pH=8, 1 mM DTT, 1 mM EDTA, and a three-fold excess of GDP. The cleaved protein was then diluted 5-fold with low salt buffer (50 mM NaCl, 20 mM TRIS pH=8), incubated with Ni-agarose beads (Qiagen) to remove uncleaved protein and protease, and 5 mM $MgCl_2$ and GDP was added to fully load the metal and nucleotide site of RalA. The protein was then further purified by ion exchange chromatography (HiTrap Q HP column, salt gradient from 50 to 500 mM NaCl) to give the partially purified protein, commonly in the following buffer (~230 mM NaCl, 20 mM TRIS pH=8, small amounts of GDP). The partially purified protein was either fully labeled with the desired compound (incubation overnight with an excess of compound at room temperature and several hours at 37° C. (if necessary), labeling checked by mass-spectrometry analysis), frozen down and stored at −80° C., or used for further purification.

The last purification step for the labeled or unlabeled protein was gel-filtration using a Superdex 75 column (GE, 10/300 GL) with the following buffer: 20 mM HEPES pH=7.5, 150 mM NaCl. The freshly prepared and purified protein was then concentrated to 5-20 mg/mL and used for the X-ray crystallography trays.

The described assays can be carried out with either the cleaved or uncleaved form of the protein.

Sequences for both RalA constructs were codon-optimized and synthesized by DNA2.0 using the pJexpress411 vector.

Purification protocols for preparation of mutant K-Ras were similar, substituting the corresponding K-Ras construct with mutations based on the optimally-aligned sequence.

Example 2: Covalent Modification of Ras Mutants by Competition Probes

KRAS mutant proteins were produced with one substituted amino acid selected from E62C, D92C, and H95C and with either glycine at the 12 position (WT) or an additional mutation to aspartic acid at the 12 position (G12D) relative to SEQ ID NO: 1 when optimally aligned. These mutations are depicted on an X-ray crystal structure in FIG. 2. These mutants were tested for reactivity (e.g., covalent modification of the KRAS mutant) with a panel of competition probes that bind the Switch II binding pocket and covalently modify the substituted amino acid with appropriately placed electrophiles based on modeling/docking studies. Screening was carried out by time-of-flight (TOF) mass spectrometry on an Agilent RapidFire system. Significant reaction (>25% at 6 hours) was observed for at least one competition probe for five of the six mutants (Table 2). Competition probe reactivity with the G12D mutant or other 12 position mutants may be optimized by iterative structural modification and testing.

TABLE 2

Covalent modification of Ras mutants by competition probes

| ID | Structure | Conc. (μM) | % Covalent Modification with Indicated Protein at 6 hr | | | | | |
|---|---|---|---|---|---|---|---|---|
| | | | E62C/ WT | E62C/ G12D | D92C/ WT | D92C/ G12D | H95C/ WT | H95C/ G12D |
| CP-001 | 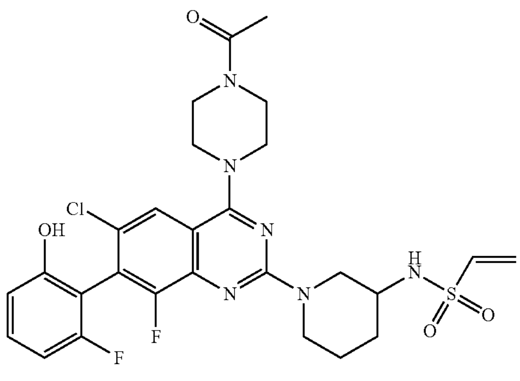 [SMILES: C=CS(=O)(=O)NC1CCCN(c2nc(N3CCN(C(C)=O)CC3)c3cc(Cl)c(-c4c(O)cccc4F)c(F)c3n2)C1] | 30 | 72 | 4 | 97 | 12 | | 60 |
| CP-002 | 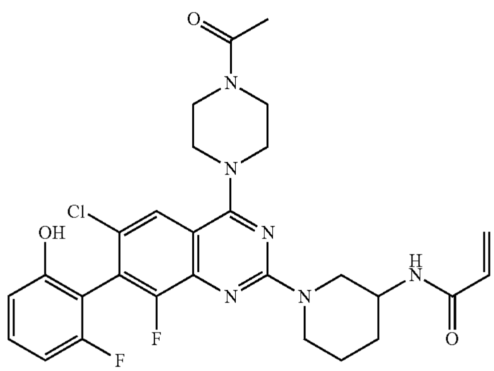 [SMILES: C=CC(=O)NC1CCCN(c2nc(N3CCN(C(C)=O)CC3)c3cc(Cl)c(-c4c(O)cccc4F)c(F)c3n2)C1] | 100 | 6 | 1 | 2 | | | 5 |
| CP-003 | 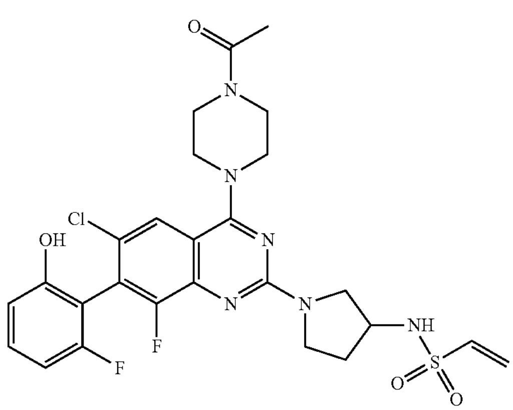 [SMILES: C=CS(=O)(=O)NC1CCN(c2nc(N3CCN(C(C)=O)CC3)c3cc(Cl)c(-c4c(O)cccc4F)c(F)c3n2)C1] | 30 | 86 | 11 | 89 | 8 | | 12 |

TABLE 2-continued

Covalent modification of Ras mutants by competition probes

| ID | Structure | Conc. (μM) | E62C/ WT | E62C/ G12D | D92C/ WT | D92C/ G12D | H95C/ WT | H95C/ G12D |
|---|---|---|---|---|---|---|---|---|
| CP-004 | 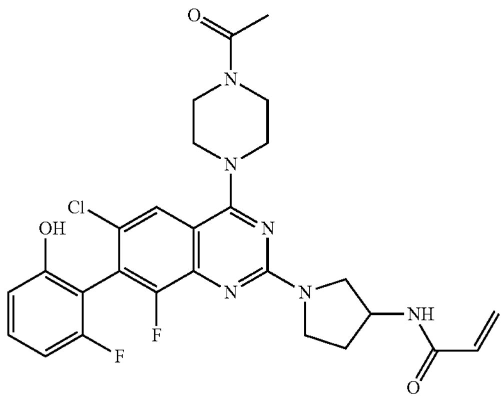 [SMILES: C=CC(=O)NC1CCN(c2nc(N3CCN(C(C)=O)CC3)c3cc(Cl)c(-c4c(O)cccc4F)c(F)c3n2)C1] | 100 | 3 | 1 | 4 | | | 2 |
| CP-005 | 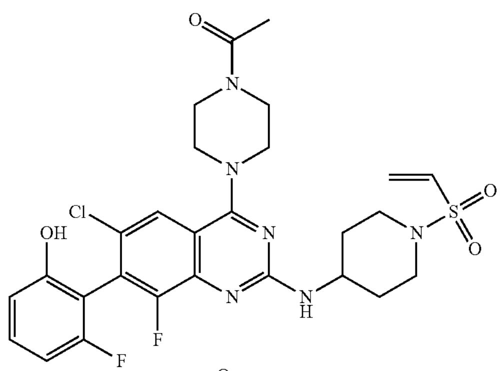 | 30 | 82 | 6 | 28 | 11 | 21 | 12 |
| CP-006 | 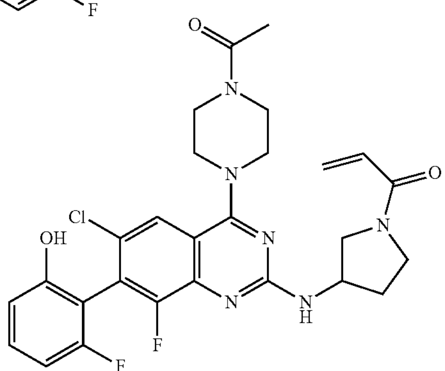 | 30 | 14 | 2 | 93 | 5 | 19 | 4 |
| CP-007 | 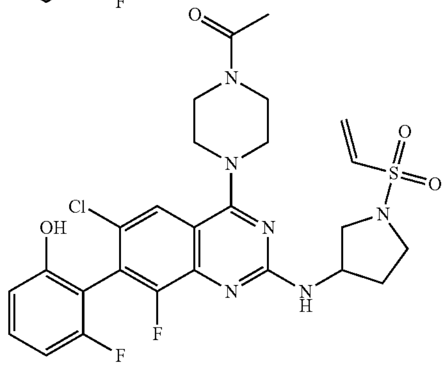 | 10 | 96 | 19 | 99 | 29 | 43 | 17 |

Example 3: Covalent Modification of Ras and RAL Mutants by Competition Probes

RALA mutant proteins were produced with one mutation to cysteine at the 23 position (G23C) relative to SEQ ID NO: 8 when optimally aligned. KRAS mutant proteins were produced with one mutation to cysteine at the 12 position (G12C) relative to SEQ ID NO: 1 when optimally aligned. The RALA and KRAS mutants were tested for reactivity (e.g., covalent modification of the mutant) with a panel of competition probes that bind the Switch II binding pocket and covalently modify the substituted amino acid with appropriately placed electrophiles based on modeling/docking studies. One such inhibitor covalently bound to RAS (via G12) is depicted in FIG. 2. Screening was carried out by mass spectrometry on an Agilent RapidFire or ThermoScientific Q Exactive system.

TABLE 3

Covalent modification of Ras mutants by competition probes

| ID | Structure | Rate Constant ($M^{-1}s^{-1}$) for Reaction with Indicated Protein | |
| --- | --- | --- | --- |
| | | RALA G23C | KRAS G12C |
| CP-008 | 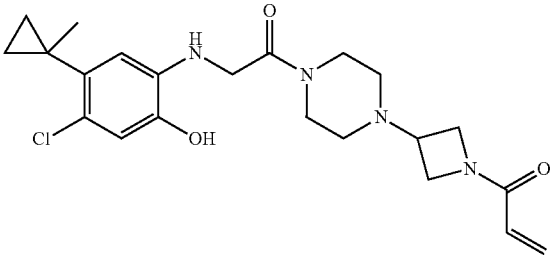 [SMILES: C=CC(=O)N1CC(N2CCN(C(=O)CNc3cc(C4(C)CC4)c(Cl)cc3O)CC2)C1] | <0.2 | 76 |
| CP-009 | 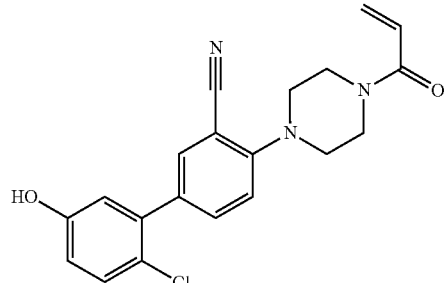 | <0.2 | 5.8 |
| CP-010 | 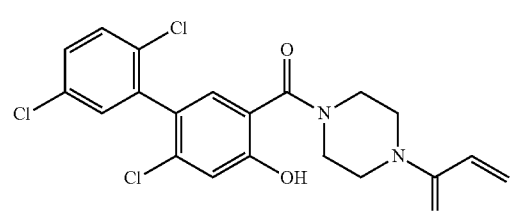 | 2.9 | 2.3 |
| CP-011 | 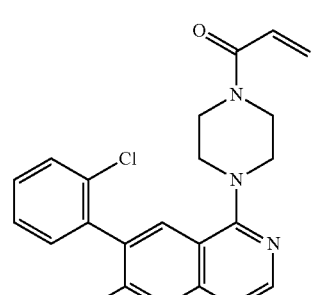 | 5.0 | 1.1 |

TABLE 3-continued
Covalent modification of Ras mutants by competition probes
| ID | Structure | Rate Constant ($M^{-1}s^{-1}$) for Reaction with Indicated Protein | |
| --- | --- | --- | --- |
| | | RALA G23C | KRAS G12C |
| CP-012 | 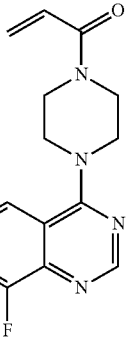 | <1 | 310 |
| CP-013 | 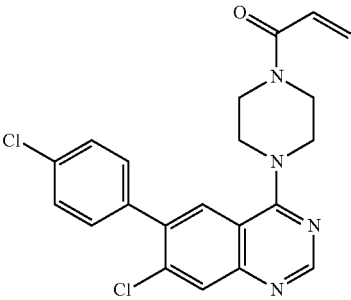 [SMILES: C=CC(=O)N1CCN(c2ncnc3cc(Cl)c(-c4ccc(Cl)cc4)cc23)CC1] | | 10.2 |
| CP-014 | 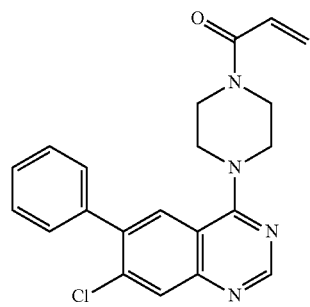 [SMILES: C=CC(=O)N1CCN(c2ncnc3cc(Cl)c(-c4ccccc4)cc23)CC1] | | 4.0 |
| CP-015 | 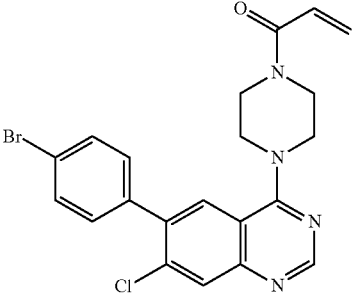 | | 9.0 |

TABLE 3-continued
Covalent modification of Ras mutants by competition probes
| | | Rate Constant ($M^{-1}s^{-1}$) for Reaction with Indicated Protein | |
|---|---|---|---|
| ID | Structure | RALA G23C | KRAS G12C |
| CP-016 | 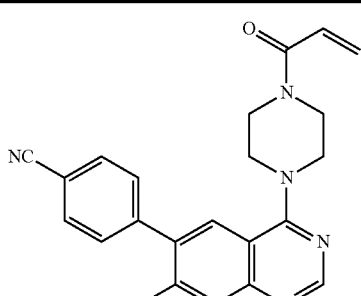 | 2.6 | |
| CP-017 | 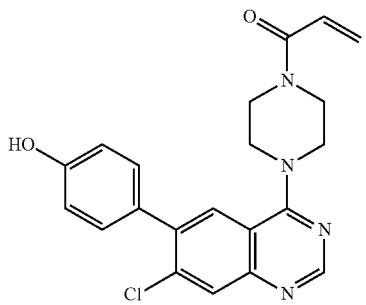 [SMILES: C=CC(=O)N1CCN(c2ncnc3cc(Cl)c(-c4ccc(C#N)cc4)cc23)CC1] | 6.0 | |
| CP-018 | 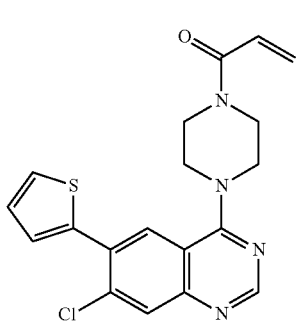 [SMILES: C=CC(=O)N1CCN(c2ncnc3cc(Cl)c(-c4cccs4)cc23)CC1] | 17 | |
| CP-019 | 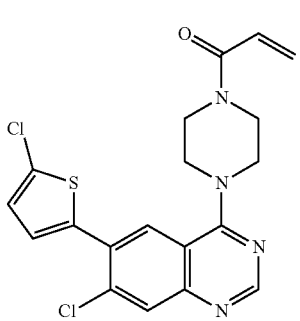 [SMILES: C=CC(=O)N1CCN(c2ncnc3cc(Cl)c(-c4ccc(Cl)s4)cc23)CC1] | 6.3 | |

TABLE 3-continued

Covalent modification of Ras mutants by competition probes

| ID | Structure | Rate Constant ($M^{-1}s^{-1}$) for Reaction with Indicated Protein | |
|---|---|---|---|
| | | RALA G23C | KRAS G12C |
| CP-020 | [structure] | | 19 |

Example 4: Intact Protein Screening for Inhibitors of Mutant Ras Under Conditions where the Competition Probe is Limiting ([Mutant Ras]>>[Competition Probe])

Mutant Ras is incubated with competition probe under conditions suitable for binding. The concentrations of free mutant Ras and competition probe-bound mutant Ras are detected and quantified using mass spectrometry. The binding interaction between an affinity-tagged competition probe and mutant Ras is measured, for example, by using an ELISA assay. Depletion of the free competition probe by binding to the mutant Ras is monitored by mass spectrometry.

Example 5: Intact Protein Screening for Inhibitors of Mutant Ras Under Conditions where the Mutant Ras Protein is Limiting ([Competition Probe]>>[Mutant Ras])

Mutant Ras is incubated with competition probe under conditions suitable for binding. The concentration of free competition probe is detected and quantified using mass spectrometry. The fluorescence polarization of a fluorescently-labeled competition probe is monitored upon binding to mutant Ras.

Example 6: Proteolytic Digest

Mutant Ras is incubated with competition probe under conditions suitable for binding. The Ras mutant is proteolytically digested. The competition probe-induced decrease in unmodified mutant Ras is monitored by mass spectrometry.

Example 7: Triple-Quadrupole (QQQ) Mass Spectrometry Protocol for K-Ras D92C Binding Using Competition Probe CP-008

The GDP-loaded K-Ras D92C protein (which also contains a histidine tag) was diluted in a HEPES containing assay buffer shortly before use in the QQQ-assay.

To start the assay an internal nonreactive control compound and competition probe compound (CP-008) were added to the protein solution to form a master mix. The master mix was quickly dispersed in a 96-well plate followed by addition a DMSO stock of the compound of interest. The reaction plate was sealed, mixed, briefly centrifuged, and then incubated for about 5 hours at room temperature while shaking (~300 rpm).

To quench the reaction, the reaction mix was transferred to 2% of formic acid in water (0.2% final in the quenched reaction) in a second plate. After sealing the second plate and quick centrifugation the samples were frozen at −80° C.

The frozen samples were sent on dry ice to Pure Honey Technologies for QQQ-quantitation to determine probe and internal control compound amount in each well. For analysis of the obtained data, the ratio of probe to internal control compound was calculated for each well. The assay window was determined by a negative control (DMSO only, no inhibition) and a positive control (100 µM final of CP-008 at a time point where the probe is fully reacted with protein; assigned 100% inhibition) and allowed the calculation of inhibition of probe depletion by the compound of interest. FIG. 6 demonstrates this QQQ assay using test compounds CP-023 or CP-024 over a range of concentrations to produce an inhibition curve for K-Ras. As increasing amounts of CP-023 or CP-024 are titrated into the reaction containing K-Ras and CP-008, less CP-008 is bound to K-Ras and the curve progresses away from the 0% inhibition value on the y-axis (100% K-Ras bound to CP-008, illustrated in FIG. 1 top panel) toward 100% inhibition value on the y-axis (no CP-008 bound to K-Ras, illustrated in FIG. 1 bottom panel).

Example 8: Fluorescence Polarization Assay for Ras Binding Using Competition Probe A Ras competition probe is conjugated to a fluorophore at a suitable position that does not interfere with the probe's binding to Ras to produce a fluorescent competition probe (FL-CP). A suitable fluorophore may comprise any of the various fluorescent probes disclosed herein. GDP-loaded Ras is diluted in a suitable assay buffer.

A series of calibration fluorescence measurements are performed to determine: a) the background fluorescence intensity of the assay buffer; b) the fluorescence polarization of the FL-CP at assay concentration alone in the assay buffer; and c) the fluorescence polarization of the FL-CP at assay concentration added to the GDP-loaded Ras at assay concentration in assay buffer under conditions of maximal binding between the CP and Ras. For the purposes of analysis, (a) represents background fluorescence, (b) represents 100% binding of a test compound, and (c) represents 0% binding of a test compound.

To measure the binding of test compounds, test compounds are incubated in assay buffer along with Ras and FL-CP such that the FL-CP is limiting ([FL-CP]<[Ras]), the fluorescence polarization value is measured, and this value is compared to the fluorescence calibration values previously determined.

Example 9: FRET Quenching Assay for Ras Binding Using Competition Probe

A Ras competition probe is conjugated to a FRET donor fluorophore at a suitable position that does not interfere with the probe's binding to Ras to produce a fluorescent competition probe (FL-CP). Suitable fluorophores include any of the various fluorescent probes disclosed herein. Ras protein is conjugated to an appropriate FRET acceptor fluorophore at a location within the FRET radius of the switch II binding pocket to create a fluorescent Ras-acceptor, loaded with GDP, and diluted in a suitable assay buffer.

A series of calibration fluorescence measurements are performed at approximately the wavelength of emission of the FL-CP fluorophore to determine: (a) the background fluorescence intensity of the assay buffer; (b) the fluorescence intensity of FL-CP at assay concentration alone in the assay buffer (unquenched); and (c) the fluorescence polarization of the FL-CP at assay concentration added to the GDP-loaded Ras-acceptor at assay concentration in assay buffer under conditions of maximal binding between the FL-CP and Ras-acceptor, in which case the association of the donor fluorophore and the acceptor fluorophore quenches the donor fluorescence. For the purposes of analysis, fluorescence measurement of (a) above represents background fluorescence, fluorescence measurement of (b) represents 100% binding of a test compound, and fluorescence measurement of (c) represents 0% binding of a test compound. To measure the binding of test compounds, test compounds are incubated in assay buffer in the presence of Ras-acceptor and FL-CP, the donor fluorescence is measured, and this value is compared to the fluorescence calibration values previously determined.

An alternative design utilizes a FRET pair to conduct the competition assay in which a competition probe conjugated to a FRET quencher (i.e., an acceptor in this alternative design) is brought to contact with a fluorescent Ras protein that is conjugated to an appropriate FRET donor. A series of calibration fluorescence measurements are performed at approximately the wavelength of emission of the Ras-donor to determine: (i) the background fluorescence intensity of the assay buffer; (ii) the fluorescence intensity of Ras-donor at assay concentration alone in the assay buffer (unquenched); and (iii) the fluorescence of the Ras-acceptor when FL-CP at assay concentration is added to the GDP-loaded Ras-donor at assay concentration in assay buffer under conditions of maximal binding between the FL-CP and Ras-acceptor, in which case the association of the FL-CP acceptor and Ras-donor quenches the donor fluorescence. For the purposes of analysis, fluorescence measurement of (i) above represents background fluorescence, fluorescence measurement of (ii) represents 100% binding of a test compound, and fluorescence measurement of (iii) represents 0% binding of a test compound. To measure the binding of test compounds, test compounds are incubated in assay buffer in the presence of Ras-donor and FL-CP acceptor, the donor fluorescence is measured, and this value is compared to the fluorescence calibration values previously determined.

Example 10: ELISA Assay for Ras Binding Using Competition Probe

A Ras competition probe is conjugated to a detectable ligand at a suitable position that does not interfere with the probe's binding to Ras to produce a ligand-conjugated competition probe (L-CP). Suitable detectable ligands include any of those disclosed herein. Hexahistidine-tagged Ras protein ("hexahistidine" disclosed as SEQ ID NO: 49) is loaded with GDP and diluted in a suitable assay buffer.

To start the assay, a test compound, hexahistidine-tagged Ras ("hexahistidine" disclosed as SEQ ID NO: 49), and L-CP are added to the assay buffer. To terminate the assay, the hexahistidine-tagged Ras ("hexahistidine" disclosed as SEQ ID NO: 49) is immobilized on a Ni-NTA coated substrate and washed with assay buffer to remove unbound compound. To detect the level of competition probe bound to Ras, an anti-ligand-HRP conjugate antibody is added to the hexahistidine-tagged Ras ("hexahistidine" disclosed as SEQ ID NO: 49), the substrate is washed with assay buffer, TMB substrate is added, and absorbance of the solution is read at 650 nm. The assay window is determined by a positive control (Hexahistidine-tagged Ras ("hexahistidine" disclosed as SEQ ID NO: 49), no L-CP, assigned 100% inhibition) and a negative control (Hexahistidine-tagged Ras ("hexahistidine" disclosed as SEQ ID NO: 49) and L-CP at a time point where the covalent labeling has gone to completion, assigned 0% inhibition).

Alternatively, the assay can be performed to detect Ras rather than the competition probe. The assay is started similarly by adding a test compound, hexahistidine-tagged Ras ("hexahistidine" disclosed as SEQ ID NO: 49), and L-CP to the assay buffer. However, in this format the reaction is quenched by immobilizing the L-CP-Ras complex on a substrate coated with a receptor complementary to the ligand (in one embodiment, the ligand is biotin and the substrate is streptavidin-coated), and washing. To detect Ras immobilized on the substrate via covalent modification by the L-CP, an anti-Ras or anti-polyhistidine HRP conjugate antibody is added, and an appropriate HRP substrate (e.g., TMB) is added followed by spectrophotometry at 650 nm. The assay window is determined by a negative control (L-CP alone, no Ras, assigned 0% inhibition) and a positive control (L-CP and Ras at a time point when the covalent labeling has gone to completion, assigned 100% inhibition)

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of selecting a Ras antagonist, the method comprising:
   (a) combining in a reaction mixture a mutant Ras, a competition probe, and a test compound; and
   (b) detecting a decrease in binding between the mutant Ras and the competition probe as compared to binding of the competition probe to the mutant Ras in an absence of the test compound; wherein:
   i. the mutant Ras comprises a truncated or full-length sequence according to SEQ ID NO: 1, SEQ ID NO: 2, SEQ ID NO: 3, or SEQ ID NO: 4, that is mutated to have up to 20 mutations including mutation of SEQ ID NO: 1, SEQ ID NO: 2, SEQ ID NO: 3, or SEQ ID NO: 4 at amino acid residue 62, 92, or 95 to cysteine;
   ii. the competition probe is capable of binding and covalently modifying the mutant Ras; and
   iii. the decrease in binding between the mutant Ras and the competition probe is indicative of Ras antagonist activity of the test compound.

2. The method of claim 1, wherein the competition probe competes for binding in a Switch II pocket of the mutant Ras.

3. The method of claim 1, wherein the competition probe is capable of covalently modifying the mutant Ras by reacting with a cysteine residue of the cysteine mutation.

4. The method of claim 1, wherein cysteine mutation is not at position 12 or 13 relative to SEQ ID NO: 1.

5. The method of claim 1, wherein cysteine mutation is at position 12 or 13 relative to SEQ ID NO: 1.

6. The method of claim 1, wherein the mutant Ras comprises the amino acid sequence of SEQ ID NO: 27, SEQ ID NO: 28, or SEQ ID NO: 29.

7. The method of claim 1, wherein the mutant Ras is (1) a mutant KRAS comprising mutations of G12D and D92C, or (2) a mutant KRAS comprising mutations of G12D and H95C.

8. The method of claim 1, wherein the mutant Ras comprises the amino acid sequence of SEQ ID NO: 33, SEQ ID NO: 34, or SEQ ID NO: 35.

9. The method of claim 1, wherein the mutant Ras comprises the truncated or full-length sequence according to SEQ ID NO: 1, SEQ ID NO: 2, SEQ ID NO: 3, or SEQ ID NO: 4, in which position 62 is C (cysteine) and position 12 is D (aspartic acid).

10. The method of claim 1, wherein the mutant Ras comprises the truncated or full-length sequence according to SEQ ID NO: 1, SEQ ID NO: 2, SEQ ID NO: 3, or SEQ ID NO: 4, in which position 92 is C (cysteine) and position 12 is D (aspartic acid).

11. The method of claim 1, wherein the mutant Ras comprises the truncated or full-length sequence according to SEQ ID NO: 1, SEQ ID NO: 2, SEQ ID NO: 3, or SEQ ID NO: 4, in which position 95 is C (cysteine) and position 12 is D (aspartic acid).

12. The method of claim 1, wherein the mutant Ras comprises the truncated or full-length sequence according to SEQ ID NO: 1, SEQ ID NO: 2, SEQ ID NO: 3, or SEQ ID NO: 4, in which position 92 is C (cysteine) and position 12 is C (cysteine).

13. The method of claim 1, wherein the mutant Ras comprises the truncated or full-length sequence according to SEQ ID NO:1, SEQ ID NO: 2, SEQ ID NO:3, or SEQ ID NO: 4, in which position 62 is C (cysteine) and position 12 is C (cysteine).

14. The method of claim 1, wherein the mutant Ras has the sequence shown in SEQ ID No: 17, SEQ ID NO: 19, SEQ ID NO: 21, SEQ ID NO: 36, SEQ ID NO: 37, or SEQ ID NO: 38.

15. The method of claim 1, wherein the mutant Ras has the sequence shown in SEQ ID NO: 30, SEQ ID NO: 31, SEQ ID NO: 32, SEQ ID NO: 42, SEQ ID NO: 43, or SEQ ID NO: 44.

16. The method of claim 1, wherein detecting the decrease in binding comprises measuring the fraction of Ras covalently modified by the competition probe as determined by mass spectrometry.

17. A mutant Ras comprising a truncated or full-length sequence according to SEQ ID NO: 1, SEQ ID NO: 2, SEQ ID NO: 3, or SEQ ID NO: 4, that is mutated to have up to 20 mutations including mutation of SEQ ID NO: 1, SEQ ID NO: 2, SEQ ID NO: 3, or SEQ ID NO: 4 at amino acid residue 62, 92, or 95 to cysteine, wherein said mutant Ras exhibits the ability to react with a competition probe capable of binding and covalently modifying said mutant Ras.

18. The mutant Ras of claim 17, wherein the mutant Ras is (1) a mutant KRAS comprising G12D (aspartic acid) at position 12 and C (cysteine) at position 92, or (2) a mutant KRAS comprising (aspartic acid) at position 12 and C (cysteine) at position 95, or (3) a mutant KRAS comprising D (aspartic acid) at position 12 and C (cysteine) at position 62.

19. The mutant Ras of claim 17, wherein the mutant Ras is (1) a mutant HRAS comprising D (aspartic acid) at position 12 and C (cysteine) at position 92, or (2) a mutant HRAS comprising D (aspartic acid) at position 12 and C (cysteine) at position 95, or (3) a mutant HRAS comprising D (aspartic acid) at position 12 and C (cysteine) at position 62.

20. The mutant Ras of claim 17, wherein the mutant Ras is (1) a mutant NRAS comprising D (aspartic acid) at position 12 and C (cysteine) at position 92, or (2) a mutant NRAS comprising D (aspartic acid) at position 12 and C (cysteine) at position 95, or (3) a mutant NRAS comprising D (aspartic acid) at position 12 and C (cysteine) at position 62.

21. The mutant Ras of claim 17, wherein the mutant Ras comprises an amino acid sequence selected from the group consisting of: SEQ ID NO: 17, SEQ ID NO: 19, SEQ ID NO: 21, SEQ ID NO: 27, SEQ ID NO: 28, SEQ ID NO: 29, SEQ ID NO: 36, SEQ ID NO: 37, SEQ ID NO: 38, SEQ ID NO: 30, SEQ ID NO: 31, SEQ ID NO: 32, SEQ ID NO: 33, SEQ ID NO: 34, SEQ ID NO: 35, SEQ ID NO: 42, SEQ ID NO: 43, and SEQ ID NO: 44.

22. The mutant Ras of claim 17, wherein the mutant Ras comprises the truncated or full-length sequence of SEQ ID NO: 1 or SEQ ID NO: 2, in which the amino acid residue 62, 92, or 95 is mutated to cysteine.

23. The mutant Ras of claim 17, wherein the mutant Ras comprises the sequence shown in SEQ ID No: 17, SEQ ID NO: 19, SEQ ID NO: 21, SEQ ID NO: 36, SEQ ID NO: 37, or SEQ ID NO: 38.

24. The mutant Ras of claim 17, wherein the mutant Ras comprises SEQ ID NO: 30, SEQ ID NO: 31, SEQ ID NO: 32, SEQ ID NO: 42, SEQ ID NO: 43, or SEQ ID NO: 44.

25. The mutant Ras of claim 17, wherein a competition probe competes for binding in a Switch II pocket of the mutant Ras.

26. The mutant Ras of claim 17, wherein the mutant Ras is selected from the group consisting of mutant KRAS, mutant HRAS, mutant NRAS, and any combination thereof.

27. A polynucleotide encoding the mutant Ras of claim 17.

28. An expression vector comprising the polynucleotide of claim 27.

29. A host cell comprising the expression vector of claim 28.

30. The method of claim 1, wherein the mutant Ras comprises the amino acid sequence selected from the group consisting of: SEQ ID NO: 17, SEQ ID NO: 19, SEQ ID NO: 21, SEQ ID NO: 27, SEQ ID NO: 28, SEQ ID NO: 36, SEQ ID NO: 37, SEQ ID NO: 38, SEQ ID NO: 30, SEQ ID NO: 31, SEQ ID NO: 32, SEQ ID NO: 42, SEQ ID NO: 43, and SEQ ID NO: 44.

* * * * *

UNITED STATES PATENT AND TRADEMARK OFFICE
CERTIFICATE OF CORRECTION

PATENT NO. : 9,810,690 B2  
APPLICATION NO. : 15/342100  
DATED : November 7, 2017  
INVENTOR(S) : Matthew P. Patricelli et al.

It is certified that error appears in the above-identified patent and that said Letters Patent is hereby corrected as shown below:

In the Claims

Claim 18, Column 139, Line 45, delete "G12D" and insert -- D --.

Claim 18, Column 139, Line 47, delete "comprising (aspartic acid)" and insert -- comprising D (aspartic acid) --.

Signed and Sealed this
Tenth Day of July, 2018

Andrei Iancu
*Director of the United States Patent and Trademark Office*